(12) United States Patent
Henderson et al.

(10) Patent No.: US 12,697,393 B2
(45) Date of Patent: Aug. 4, 2026

(54) ORAL BIODELIVERY PLATFORM

(71) Applicant: BioDrive, Inc., New York, NY (US)

(72) Inventors: Cory Henderson, Oakland, CA (US); Kwangchul Kwon, Oakland, CA (US)

(73) Assignee: BioDrive, Inc., New York, NY (US)

( * ) Notice: Subject to any disclaimer, the term of this patent is extended or adjusted under 35 U.S.C. 154(b) by 0 days.

(21) Appl. No.: 19/554,962

(22) Filed: Mar. 3, 2026

(65) Prior Publication Data

US 2026/0174883 A1 Jun. 25, 2026

Related U.S. Application Data

(63) Continuation of application No. PCT/US2025/049519, filed on Oct. 3, 2025.

(60) Provisional application No. 63/860,426, filed on Aug. 8, 2025, provisional application No. 63/722,039, filed on Nov. 18, 2024, provisional application No. 63/722,040, filed on Nov. 18, 2024, provisional application No. 63/703,206, filed on Oct. 4, 2024, provisional application No. 63/703,207, filed on Oct. 4, 2024.

(51) Int. Cl.
| | |
|---|---|
| *A61K 47/00* | (2006.01) |
| *A61K 9/00* | (2006.01) |
| *A61K 31/198* | (2006.01) |
| *A61K 47/64* | (2017.01) |

(52) U.S. Cl.
CPC ............ *A61K 47/64* (2017.08); *A61K 9/0019* (2013.01); *A61K 31/198* (2013.01); *A61K 2300/00* (2013.01)

(58) Field of Classification Search
CPC .... A61K 47/64; A61K 9/0019; A61K 31/198; A61K 2300/00
See application file for complete search history.

(56) References Cited

U.S. PATENT DOCUMENTS

| | | | |
|---|---|---|---|
| 4,399,216 A | 8/1983 | Axel et al. |
| 5,015,580 A | 5/1991 | Christou et al. |
| 5,204,253 A | 4/1993 | Sanford et al. |
| 5,302,523 A | 4/1994 | Coffee et al. |
| 5,510,253 A | 4/1996 | Mitsky et al. |
| 5,559,223 A | 9/1996 | Falco et al. |
| 5,563,055 A | 10/1996 | Townsend et al. |
| 5,591,616 A | 1/1997 | Hiei et al. |
| 5,633,436 A | 5/1997 | Wandelt |
| 5,693,512 A | 12/1997 | Finer et al. |
| 5,731,179 A | 3/1998 | Komari et al. |
| 5,850,016 A | 12/1998 | Jung et al. |
| 5,885,801 A | 3/1999 | Rao |
| 5,885,802 A | 3/1999 | Rao |
| 5,912,414 A | 6/1999 | Falco et al. |
| 5,959,185 A | 9/1999 | Streit et al. |
| 5,973,234 A | 10/1999 | Mueller et al. |
| 5,977,445 A | 11/1999 | Soper et al. |
| 6,051,757 A | 4/2000 | Barton et al. |
| 6,080,913 A | 6/2000 | Tarczynski et al. |
| 6,127,600 A | 10/2000 | Beach et al. |
| 6,346,403 B1 | 2/2002 | Rafalski et al. |
| 6,441,274 B1 | 8/2002 | Cahoon et al. |
| 6,459,019 B1 | 10/2002 | Falco et al. |
| 6,506,559 B1 | 1/2003 | Fire et al. |
| 6,664,445 B1 | 12/2003 | Falco et al. |
| 6,787,618 B1 | 9/2004 | Winter et al. |
| 7,154,029 B2 | 12/2006 | Cahoon et al. |
| 7,547,821 B2 | 6/2009 | Moloney et al. |
| 7,947,876 B2 | 5/2011 | Sugita et al. |
| 8,586,363 B2 | 11/2013 | Voytas et al. |
| 8,697,359 B1 | 4/2014 | Zhang |
| 8,771,945 B1 | 7/2014 | Zhang |
| 8,795,965 B2 | 8/2014 | Zhang |
| 8,865,406 B2 | 10/2014 | Zhang et al. |
| 8,871,445 B2 | 10/2014 | Cong et al. |
| 8,889,356 B2 | 11/2014 | Zhang |
| 8,895,308 B1 | 11/2014 | Zhang et al. |
| 8,906,616 B2 | 12/2014 | Zhang et al. |
| 8,932,814 B2 | 1/2015 | Cong et al. |
| 8,945,839 B2 | 2/2015 | Zhang |
| 8,993,233 B2 | 3/2015 | Zhang et al. |
| 8,999,641 B2 | 4/2015 | Zhang et al. |
| 9,145,565 B2 | 9/2015 | Carroll et al. |
| 9,181,535 B2 | 11/2015 | Liu et al. |
| 9,474,780 B2 | 10/2016 | Bokvist et al. |
| 10,100,097 B2 | 10/2018 | Just et al. |
| 10,981,967 B2 | 4/2021 | Oh et al. |
| 11,084,861 B2 | 8/2021 | Abraham et al. |
| 11,542,313 B2 | 1/2023 | Alsina-Fernandez et al. |
| 2004/0197909 A1 | 10/2004 | McKnight et al. |
| 2006/0128607 A1 | 6/2006 | Bosserhoff et al. |

(Continued)

FOREIGN PATENT DOCUMENTS

| | | |
|---|---|---|
| CN | 115975040 A | 4/2023 |
| EP | 0265556 A1 | 5/1988 |

(Continued)

OTHER PUBLICATIONS

CapsCanada—Delay Release Explained; Jun. 10, 2024, https://blog.capscanada.com/delayed-release-capsules-explained.*
Carson—KCaps—Vegan Certification, 2021; https://www.kcaps.com/blogs/news/k-caps%C2%AE-vegan-certification.*
Atanassvoa et al., "A 126 bp fragment of a plant histone gene promoter confers preferential expression in meristems of transgenic *Arabidopsis*," The Plant Journal, May 1992, 2(3):291-300.
Bahijiri et al., "The effects of inorganic chromium and brewer's yeast supplementation on glucose tolerance, serum lipids and drug dosage in individuals with type 2 diabetes". Saudi Med J. Sep. 2000;21(9):831-7.
Bevan et al., "The Structure and Transcription Start Site of a Major Potato Tuber Protein Gene," Nucleic Acids Research, Jun. 1986, 14(11), pp. 4625-4636.
Botstein et al., "Yeast: an experimental organism for 21st century biology". Genetics. Nov. 1, 2011;189(3):695-704.

(Continued)

*Primary Examiner* — Jeanette M Lieb
(74) *Attorney, Agent, or Firm* — COOLEY LLP

(57) ABSTRACT

The present disclosure provides a biodelivery platform for the oral administration of molecular cargo.

19 Claims, 28 Drawing Sheets

Specification includes a Sequence Listing.

(56) References Cited

U.S. PATENT DOCUMENTS

| | | | |
|---|---|---|---|
| 2009/0098049 | A1 | 4/2009 | Dowdy et al. |
| 2015/0030575 | A1 | 1/2015 | Daniell |
| 2020/0362325 | A1 | 11/2020 | Collier, Jr. et al. |
| 2022/0229066 | A1 | 7/2022 | Agnew et al. |
| 2023/0084762 | A1 | 3/2023 | Gasiunas et al. |

FOREIGN PATENT DOCUMENTS

| | | | | |
|---|---|---|---|---|
| EP | | 0270822 | A1 | 6/1988 |
| EP | | 0604662 | A1 | 7/1994 |
| EP | | 0672752 | A1 | 9/1995 |
| EP | | 0904362 | B1 | 2/1997 |
| WO | WO-1983003259 | A1 | 9/1983 |
| WO | WO-1985004899 | A1 | 11/1985 |
| WO | WO-1986003516 | A1 | 6/1986 |
| WO | WO-1986003776 | A1 | 7/1986 |
| WO | WO-1992009696 | A1 | 6/1992 |
| WO | WO-1994019930 | A1 | 9/1994 |
| WO | WO-1995015392 | A1 | 6/1995 |
| WO | WO-1995016031 | A1 | 6/1995 |
| WO | WO-1996030530 | A1 | 10/1996 |
| WO | WO-1998020133 | A2 | 5/1998 |
| WO | WO-1998042831 | A2 | 10/1998 |
| WO | WO-1998045458 | A1 | 10/1998 |
| WO | WO-1998056935 | A2 | 12/1998 |
| WO | WO-1999029882 | A2 | 6/1999 |
| WO | WO-1999040209 | A1 | 8/1999 |
| WO | WO-1999067357 | A2 | 12/1999 |
| WO | WO-2000068393 | A1 | 11/2000 |
| WO | WO-2003082899 | A2 | 10/2003 |
| WO | WO-2011095545 | A1 | 8/2011 |
| WO | WO-2012175740 | A1 * | 12/2012 | .............. A61P 37/08 |
| WO | WO-2015067716 | A1 | 5/2015 |
| WO | WO-2021003456 | A1 | 1/2021 |
| WO | WO-2023030444 | A1 | 3/2023 |

OTHER PUBLICATIONS

Briskey et al., "Effect of Yeast Protein on Muscle Mass and Performance in an Adult Population—a Double Blind, Randomised Controlled Trial". Journal of Food and Nutrition Research. 2024; 12(5):292-300.

Center for Disease Control and Prevention, "Adult Obesity Facts," [website], CDC.gov, Center for Disease Control and Prevention, May 14, 2024; last updated date unknown. [Accessed Mar. 27, 2026, publicly available at URL: https://www.cdc.gov/obesity/adult-obesity-facts/], 3 pages.

Chalfie et al., "Green fluorescent protein as a marker for gene expression". Science. Feb. 11, 1994;263(5148):802-5.

Charest et al., "In vitro study of transgenic tobacco expressing *Arabidopsis* wild type and mutant acetohydroxyacid synthase genes". Plant Cell Reports. Apr. 1990;8(11):643-6.

Christensen et al., "Sequence analysis and transcriptional regulation by heat shock of polyubiquitin transcripts from maize". Plant molecular biology. Jun. 1989;12(6):619-32.

Christensen et al., "Maize polyubiquitin genes: structure, thermal perturbation of expression and transcript splicing, and promoter activity following transfer to protoplasts by electroporation," Plant Molecular Biology, Feb. 1992, 18:675-689.

Comai et al., "Expression in plants of a mutant aroA gene from *Salmonella typhimurium* confers tolerance to glyphosate". Nature. Oct. 24, 1985;317(6039):741-4.

Corbin et al., "Differential regulation of a hydroxyproline-rich glycoprotein gene family in wounded and infected plants". Mol Cell Biol. Dec. 1987;7(12):4337-44.

Cornejo et al., "Activity of a maize ubiquitin promoter in transgenic rice", Plant molecular biology. Nov. 1993;23(3):567-81.

Curtis et al., "Genotype-independent transformation of lettuce using Agrobacterium tumefaciens". Journal of Experimental Botany. Oct. 1, 1994;45(10):1441-9.

Davies et al., "Plasmid-determined resistance to antimicrobial agents". Annual Reviews in Microbiology. Oct. 1978;32(1):469-508.

DeBlock et al., "Expression of foreign genes in regenerated plants and in their progeny". EMBO J. Aug. 1984;3(8):1681-9.

EFSA on Biological Hazards (Biohaz) "Scientific Opinion on the maintenance of the list of QPS biological agents intentionally added to food and feed (2010 update)". EFSA Journal. Dec. 2010;8(12): 56 pages.

Eichholtz et al., "Expression of mouse dihydrofolate reductase gene confers methotrexate resistance in transgenic petunia plants". Somatic cell and molecular genetics. Jan. 1987;13(1):67-76.

Food and Agriculture Organization of the United Nations, "Guideline for the Conduct of Food Safety Assessment of Foods Derived From Recombinant-DNA Plants", Articles III, IV [website], fao.org, Food and Agriculture Organization of the United Nations, Articles adopted Jul. 2003, [Accessed Mar. 27, 2026, publicly available at URL: https://www.fao.org/fileadmin/user_upload/gmfp/docs/CAC. GL_45_2003.pdf], 18 pages.

Food and Drug Administration, "New Dietary Ingredient: NDI 1071—Ankascin 568-R," [website], regulations.gov, Apr. 27, 2018; [Accessed Date of Retrieval, publicly available at URL: https://www.regulations.gov/document/FDA-2018-S-0023-0078], 129 pages.

Food and Drug Administration, "New Dietary Ingredient: NDI 1241—Deglusterol powder from Caregen Co., Ltd.," [website], regulations.gov, Jan. 7, 2022; [Accessed Apr. 2, 2026, publicly available at URL: https://www.regulations.gov/document/FDA-2022-S-0023-0015], 27 pages.

Food and Drug Administration, "New Dietary Ingredient:NDI 1303—Inulinase Enzyme Preparation—Original NDI Notification," [website], regulations.gov, Jul. 28, 2026; [Accessed Apr. 2, 2026, publicly available at URL: https://www.regulations.gov/document/FDA-2023-S-0023-0081], 35 pages.

Fraley et al., "Expression of bacterial genes in plant cells". Proceedings of the National Academy of Sciences. Aug. 1983;80(15):4803-7.

Fromm et al., "Stable transformation of maize after gene transfer by electroporation". Nature. Feb. 27, 1986;319(6056):791-3.

Gao et al., "DNA-guided genome editing using the Natronobacterium gregoryi Argonaute". Nature biotechnology. Jul. 2016;34(7):768-73.

Gatz et al., "Regulation of a modified CaMV 35S promoter by the Tn10-encoded Tet repressor in transgenic tobacco". Mol Gen Genet. Jun. 1991;227(2):229-37.

Goffeau et al., "Life with 6000 genes," Science. Oct. 25, 1996;274(5287):546, 563-7.

Gordon-Kamm et al., "Transformation of maize cells and regeneration of fertile transgenic plants". The Plant Cell. Jul. 1, 1990;2(7):603-18.

Gray et al., "Evolution of antibiotic resistance genes: the DNA sequence of a kanamycin resistance gene from *Staphylococcus aureus*". Molecular biology and evolution. Dec. 1, 1983;1(1):57-66.

Guerrero et al., "Promoter sequences from a maize pollen-specific gene direct tissue-specific transcription in tobacco". Mol Gen Genet. Nov. 1990;224(2):161-8.

Hayford et al., "Development of a plant transformation selection system based on expression of genes encoding gentamicin acetyltransferases". Plant physiology. Apr. 1, 1988;86(4):1216-22.

Hershey et al., "Isolation and characterization of cDNA clones for RNA species induced by substituted benzenesulfonamides in corn". Plant molecular biology. Oct. 1991;17(4):679-90.

Hileman et al., "Bioinformatic methods for allergenicity assessment using a comprehensive allergen database". International archives of allergy and immunology. Sep. 6, 2002;128(4):280-91.

Horsch et al., "A Simple and General Method for Transferring Genes into Plants," Science, Mar. 1985, 227:1229-1231.

Ituriaga et al., "Endoplasmic reticulum targeting and glycosylation of hybrid proteins in transgenic tobacco". Plant Cell. Mar. 1989;1(3):381-90.

Jach et al., "Yeast protein as an easily accessible food source". Metabolites. Jan. 11, 2022;12(1): 27 pages.

Jefferson "Assaying chimeric genes in plants: the GUS gene fusion system. Plant molecular biology reporter". Dec. 1987;5(4):387-405.

(56)                References Cited

OTHER PUBLICATIONS

Jester et al., "Development of spirulina for the manufacture and oral delivery of protein therapeutics". Nature Biotechnology. Jun. 2022;40(6):956-64.

Jimenez et al., "Expression of a transposable antibiotic resistance element in *Saccharomyces*". Nature. Oct. 30, 1980;287(5785):869-71.

Jin et al., "Pathophysiology of obesity and its associated diseases". Acta Pharmaceutica Sinica B. Jun. 1, 2023;13(6):2403-24.

Jones et al., "A dominant nuclear streptomycin resistance marker for plant cell transformation". Molecular and General Genetics MGG. Nov. 1987;210(1):86-91.

Jung et al., "Low dose yeast hydrolysate in treatment of obesity and weight loss". Preventive nutrition and food science. Mar. 31, 2017;22(1): 5 pages.

Jung et al., "Yeast hydrolysate can reduce body weight and abdominal fat accumulation in obese adults". Nutrition. Jan. 1, 2014;30(1):25-32.

Kado et al., "Molecular mechanisms of crown gall tumorigenesis". Critical Reviews in Plant Sciences. Jan. 1, 1991;10(1):1-32.

Kjeldsen et al., "Expression of insulin in yeast: the importance of molecular adaptation for secretion and conversion". Biotechnology and genetic engineering reviews. Jul. 1, 2001;18(1):89-121.

Knerr et al., "Next generation GLP-1/GIP/glucagon triple agonists normalize body weight in obese mice". Molecular Metabolism. Sep. 1, 2022;63: 12 pages.

Koncz et al., "Expression and assembly of functional bacterial luciferase in plants". Proceedings of the National Academy of Sciences. Jan. 1987;84(1):131-5.

Last et al., "pEmu: an improved promoter for gene expression in cereal cells". Theoretical and applied genetics. May 1991;81(5):581-8.

Lepetit et al., "A plant histone gene promoter can direct both replication-dependent and-independent gene expression in transgenic plants". Molecular and General Genetics MGG. Jan. 1992;231(2):276-85.

Liu et al., "The impact of diabetes on vascular disease: progress from the perspective of epidemics and treatments". Journal of diabetes research. 2022;2022(1): 17 pages.

Lopez et al., "Biochemistry, essential amino acids". InStatPearls Apr. 30, 2024. In: StatPearls [Internet]. Treasure Island (FL): StatPearls Publishing; Jan. 2026—[Retrieved Mar. 27, 2026: https://www.ncbi.nlm.nih.gov/sites/books/NBK557845/], 6 pages.

Mcelroy et al., "Isolation of an Efficient Actin Promoter for Use in Rice Transformation," The Plant Cell, Feb. 1990, 2(2):163-171.

Mett et al., "Copper-controllable gene expression system for whole plants". Proceedings of the National Academy of Sciences. May 15, 1993;90(10):4567-71.

Michelmore et al., "Identification of markers linked to disease-resistance genes by bulked segregant analysis: a rapid method to detect markers in specific genomic regions by using segregating populations". Proceedings of the national academy of sciences. Nov. 1, 1991;88(21):9828-32.

Moloney et al., "High efficiency transformation of Brassica napus using Agrobacterium vectors". Plant Cell Reports. Apr. 1989;8(4):238-42.

Murai et al., "Phaseolin gene from bean is expressed after transfer to sunflower via tumor-inducing plasmid vectors". Science. Nov. 4, 1983;222(4623):476-82.

Nagata et al., "Evaluation of glyphosate resistance in transgenic lettuce". Journal of the American Society for Horticultural Science. Nov. 1, 2000;125(6):669-72.

Naleway et al., "Detection of GUS Gene Expression in Transformed Plant Cells With New Lipophilic, Fluorogenic β-Glucuronidase Substrate". J. Cell Biol. 1991;115(3): 4 pages.

National Research Council "Guide for the Care and Use of Laboratory Animals", [website], grants.nih.gov, National Academy of Sciences, 2011, [Retrieved Mar. 27, 2026: https://grants.nih.gov/grants/olaw/guide-for-the-care-and-use-of-laboratory-animals.pdf], 246 pages.

Negrouk et al., "Highly efficient transient expression of functional recombinant antibodies in lettuce". Plant Science. Aug. 1, 2005;169(2):433-8.

Odell et al., "Identification of DNA sequences required for activity of the cauliflower mosaic virus 35S promoter". Nature. Feb. 28-Mar. 6, 1985;313(6005):810-2.

Parapouli et al., "*Saccharomyces cerevisiae* and its industrial applications". AIMS microbiology. Feb. 11, 2020;6(1): 31 pages.

PCT Application No. PCT/US2025/049519, International Search Report and Written Opinion mailed Jan. 22, 2026, Applicant Biodrive, Inc. et al.; 15 pages.

PCT Application No. PCT/US2025/049519, Invitation to Pay Additional Fees mailed Nov. 26, 2025; Applicant Biodrive, Inc.; 3 pages.

Quarrie et al., "Bulk segregant analysis with molecular markers and its use for improving drought resistance in maize". Journal of experimental botany. Aug. 1, 1999;50(337):1299-306.

Racek et al., "Influence of chromium-enriched yeast on blood glucose and insulin variables, blood lipids, and markers of oxidative stress in subjects with type 2 diabetes mellitus". Biological trace element research. Mar. 2006;109(3):215-30.

Rasmussen et al., "Nucleotide sequence of a cDNA coding for the barley seed protein CMa: an inhibitor of insect alpha-amylase". Plant Mol Biol. Jan. 1992;18(2):423-7.

Roder et al., "Efficiency of the tetracycline-dependent gene expression system: complete suppression and efficient induction of the rolB phenotype in transgenic plants". Mol Gen Genet. Apr. 1994;243(1):32-8.

Rogers JC. Two barley alpha-amylase gene families are regulated differently in aleurone cells. Journal of Biological Chemistry. Mar. 25, 1985;260(6):3731-8.

Sauer et al., "Functional expression of the cre-lox site-specific recombination system in the yeast *Saccharomyces cerevisiae*". Molecular and cellular biology. Jun. 1, 1987;7(6):2087-96.

Schena et al., "A steroid-inducible gene expression system for plant cells". Proc Natl Acad Sci U S A. Dec. 1, 1991;88(23):10421-5.

Sengupta-Gopalan et al., "Developmentally regulated expression of the bean β-phaseolin gene in tobacco seed". Proceedings of the National Academy of Sciences. May 1985;82(10):3320-4.

Seymour et al., "Rapid creation of *Arabidopsis* doubled haploid lines for quantitative trait locus mapping". Proceedings of the National Academy of Sciences. Mar. 13, 2012;109(11):4227-32.

Sfera et al., "The other obesity epidemic—of drugs and bugs". Frontiers in Endocrinology. Jul. 31, 2020;11: 16 pages.

Shah et al., "Engineering herbicide tolerance in transgenic plants". Science. Jul. 25, 1986;233(4762):478-81.

Sijmons et al., "Production of correctly processed human serum albumin in transgenic plants". Bio/technology. Mar. 1, 1990;8(3):217-21.

Simpson et al., "Light-inducible and tissue-specific expression of a chimaeric gene under control of the 5'-flanking sequence of a pea chlorophyll a/b-binding protein gene". The EMBO Journal. Nov. 1, 1985;4(11):2723-9.

Stalker et al., "Herbicide resistance in transgenic plants expressing a bacterial detoxification gene". Science. Oct. 21, 1988;242(4877):419-23.

Tambo et al., "The microbial hypothesis: contributions of adenovirus infection and metabolic endotoxaemia to the pathogenesis of obesity". International Journal of Chronic Diseases. 2016;2016(1): 11 pages.

Teeri al., "Gene fusions to lacZ reveal new expression patterns of chimeric genes in transgenic plants". The EMBO Journal. Feb. 1, 1989;8(2):343-50.

Teng et al., "Rapid regeneration of lettuce from suspension culture". HortScience. Sep. 1, 1992;27(9):1030-2.

Teng et al., "Regenerating lettuce from suspension culture in a 2-liter bioreactor". HortScience. Jun. 1, 1993;28(6):669-71.

Timko et al., "Light regulation of plant gene expression by an upstream enhancer-like element". Nature. Dec. 12, 1985;318(6046):579-82.

Twell et al., "Activation and developmental regulation of an *Arabidopsis anther*-specific promoter in microspores and pollen of Nicotiana tabacum". Sexual Plant Reproduction. Oct. 1993;6(4):217-24.

(56)　　　　　References Cited

OTHER PUBLICATIONS

Twell et al., "Isolation and expression of an anther-specific gene from tomato". Molecular and general genetics Mgg. Jun. 1989;217(2):240-5.

U.S. Environmental Protection Agency, "Final risk assessment of *Saccharomyces cerevisiae*", [website], epa.gov, U.S. Environment Protection Agency, Jul. 1997 [Accessed Mar. 27, 2026, publicly available at URL: https://www.epa.gov/sites/default/files/2015-09/documents/fra002.pdf], 13 pages.

U.S. Food & Drug Administration "GRAS Determination for *Saccharomyces cerevisiae* strain OYR-243", GRAS Notice (GRN) No. 1096, [website], fda.gov, U.S. Food & Drug Administration, Jun. 24, 2022, [Accessed Mar. 27, 2026, publicly available at URL: https://www.fda.gov/media/170676/download], 57 pages.

U.S. Food & Drug Administration "Microorganisms & Microbial-Derived Ingredients Used in Food (Partial List)", [website], fda.gov, U.S. Food & Drug Administration, Jan. 4, 2018, [Accessed Mar. 27, 2026, publicly available at URL: https://www.fda.gov/food/generally-recognized-safe-gras/microorganisms-microbial-derived-ingredients-used-food-partial-list], 6 pages.

Van Den et al., A chimaeric hygromycin resistance gene as a selectable marker in plant cells. Plant Molecular Biology. Sep. 1985;5(5):299-302.

Velten et al., "Isolation of a dual plant promoter fragment from the Ti plasmid of *Agrobacterium tumefaciens*". The EMBO Journal. Dec. 1, 1984;3(12):2723-30.

Ward et al., "Chemical regulation of transgene expression in plants". Plant Mol Biol. May 1993;22(2):361-6.

Watts et al., "Socioeconomic differences in overweight and weight-related behaviors across adolescence and young adulthood: 10-year longitudinal findings from Project EAT". Preventive medicine. Jun. 1, 2016;87:194-9.

Webb et al., "Plant regeneration from mesophyll protoplasts of *Lactuca perennis*". Plant cell, tissue and organ culture. Jul. 1994;38(1):77-9.

Welsh et al., "Obesity and cardiovascular health". European journal of preventive cardiology. Jun. 2024;31(8):1026-35.

World Health Organization "valuation of food additives: some enzymes, modified starches, and certain other substances: toxicological evaluations and specifications and a review of the technological efficacy of some antioxidants: fifteenth report of the JECFA", who.int, World Health Organization, Jun. 16-24, 1971, [Accessed Mar. 27, 2026, publicly available at URL: https://www.who.int/publications/i/item/9241204885], 42 pages.

Wu et al., "Endocrine, genetic, and microbiome nexus of obesity and potential role of postbiotics: a narrative review". Eating and Weight Disorders—Studies on Anorexia, Bulimia and Obesity. Oct. 20, 2023;28(1): 17 pages.

Xiao et al., "Low cost delivery of proteins bioencapsulated in plant cells to human non-immune or immune modulatory cells". Biomaterials. Feb. 1, 2016;80:68-79.

Yan et al., "Gene fusions of signal sequences with a modified β-glucuronidase gene results in retention of the β-glucuronidase protein in the secretory pathway/plasma membrane". Plant physiology. Nov. 1, 1997;115(3):915-24.

Yang, H., et al., "Production of kanamycin resistant rice tissues following DNA uptake into protoplasts," Plant Cell Reports 1988, 7:421-425.

Zhang et al., "Genotypic effects on tissue culture response of lettuce cotyledons". J. Genet. & Breed (1992), 46:287-290.

Zhang et al., "Chromosome elimination and in vivo haploid production induced by Stock 6-derived inducer line in maize (*Zea mays* L.)". Plant Cell Rep. Dec. 2008;27(12):1851-60.

Zhu et al., "Cleavage-dependent Ligation by the FLP Recombinase: Characterization of a mutant FLP protein with an alteration in a catalytic amino acid". Journal of Biological Chemistry. Sep. 29, 1995;270(39):23044-54.

Zorzi et al., "Non-covalent albumin-binding ligands for extending the circulating half-life of small biotherapeutics". MedChemComm. 2019;10(7):1068-81.

* cited by examiner

Figure 1C:
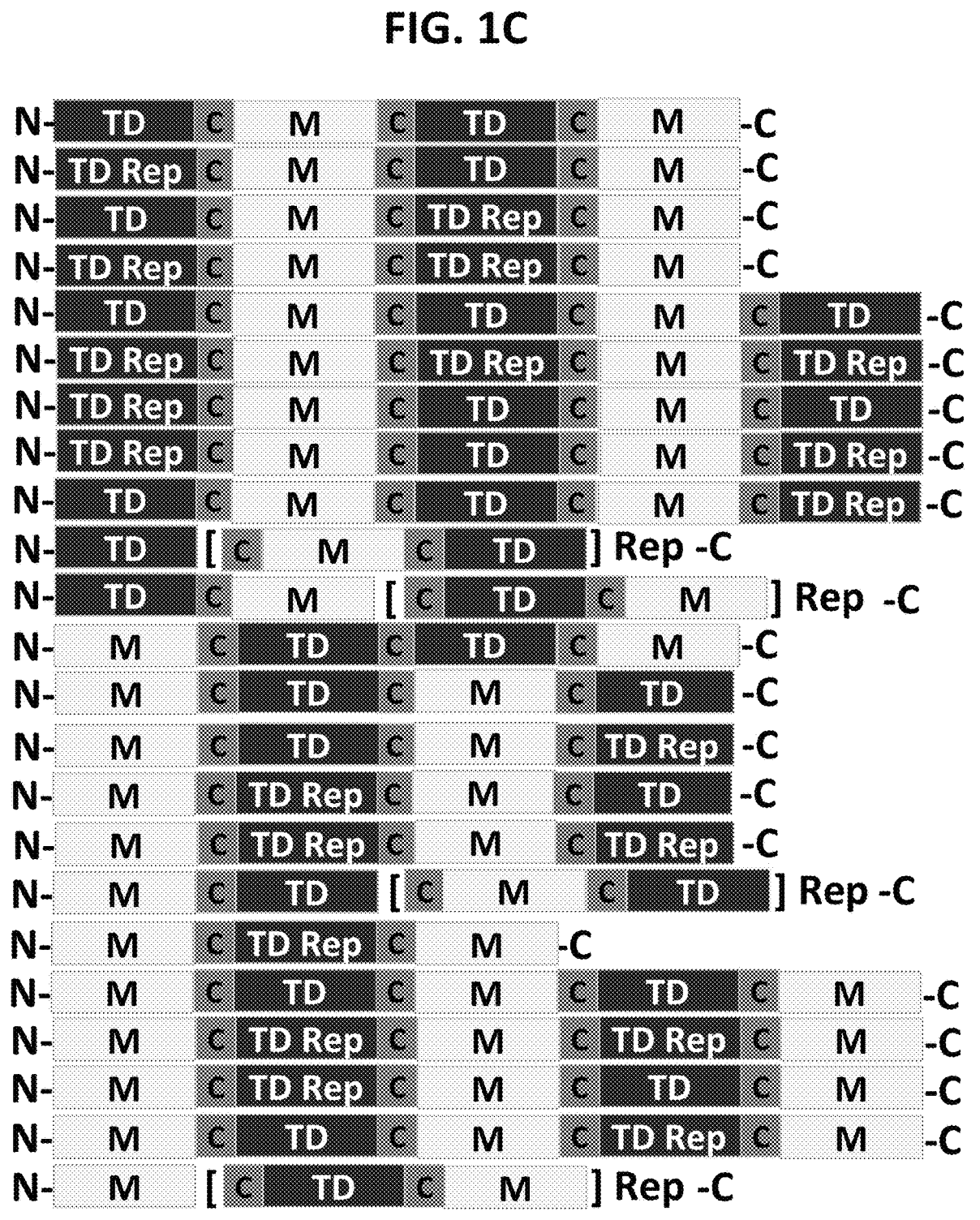

N- TD Rep C M C TD C M -C

N- TD C M C TD Rep C M -C

N- TD Rep C M C TD Rep C M -C

N- TD C M C TD C M C TD -C

N- TD Rep C M C TD Rep C M C TD Rep -C

N- TD Rep C M C TD C M C TD -C

N- TD Rep C M C TD C M C TD Rep -C

N- TD C M C TD C M C TD Rep -C

N- TD [ C M C TD ] Rep -C

N- TD C M [ C TD C M ] Rep -C

N- M C TD C TD C M -C

N- M C TD C M C TD -C

N- M C TD C M C TD Rep -C

N- M C TD Rep C M C TD -C

N- M C TD Rep C M C TD Rep -C

N- M C TD [ C M C TD ] Rep -C

N- M C TD Rep C M -C

N- M C TD C M C TD C M -C

N- M C TD Rep C M C TD Rep C M -C

N- M C TD Rep C M C TD C M -C

N- M C TD C M C TD Rep C M -C

N- M [ C TD C M ] Rep -C

Figure 2A:
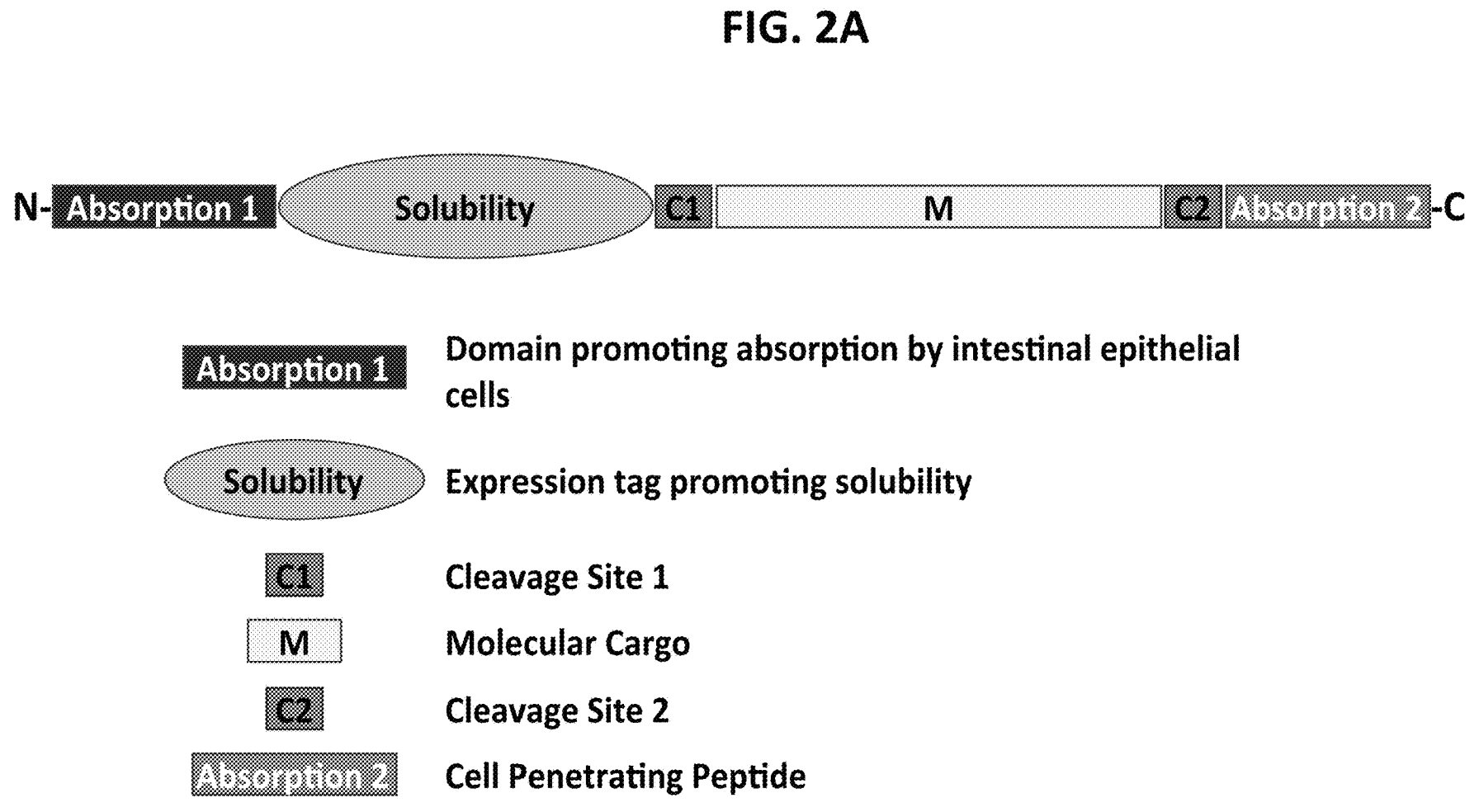

Absorption 1 — Domain promoting absorption by intestinal epithelial cells

Solubility — Expression tag promoting solubility

C1 — Cleavage Site 1

M — Molecular Cargo

C2 — Cleavage Site 2

Absorption 2 — Cell Penetrating Peptide

FIG. 2B

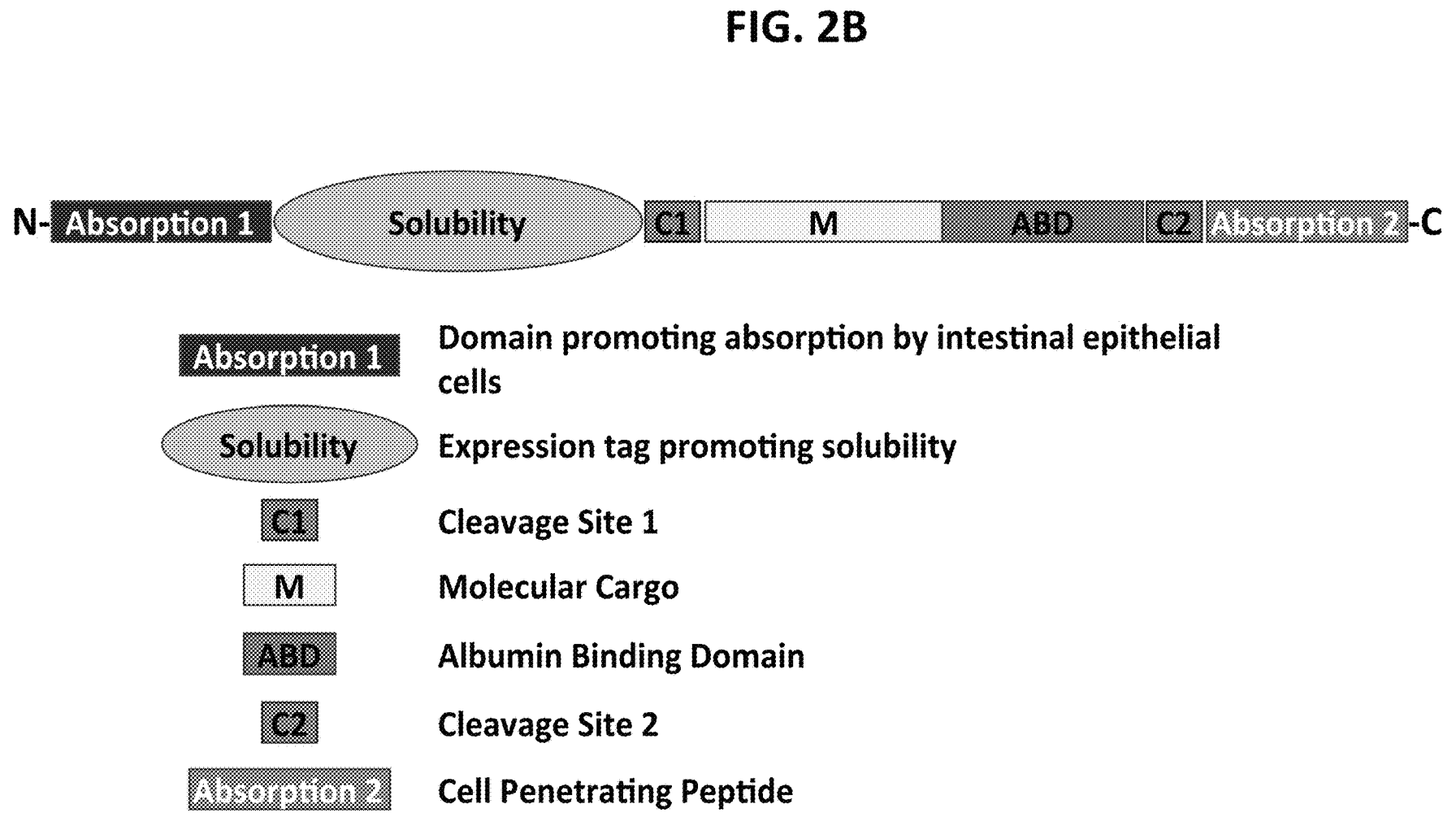

Absorption 1    Domain promoting absorption by intestinal epithelial cells

Solubility    Expression tag promoting solubility

C1    Cleavage Site 1

M    Molecular Cargo

ABD    Albumin Binding Domain

C2    Cleavage Site 2

Absorption 2    Cell Penetrating Peptide

Figure 3:
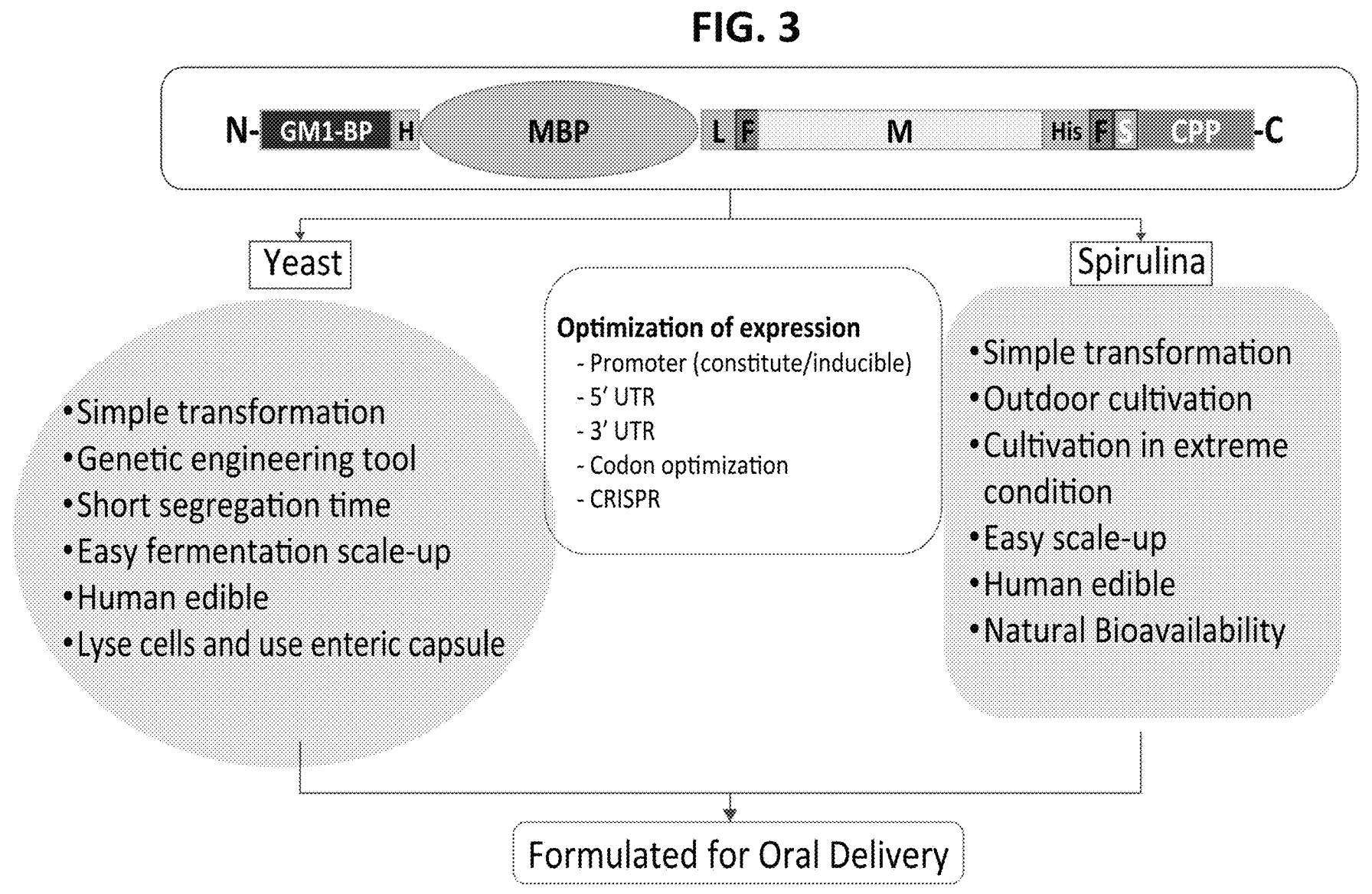

N- GM1-BP H MBP L F M His F S CPP -C

Yeast

Spirulina

Optimization of expression
- Promoter (constitute/inducible)
- 5' UTR
- 3' UTR
- Codon optimization
- CRISPR Spirulina
- Simple transformation
- Outdoor cultivation
- Cultivation in extreme condition
- Easy scale-up
- Human edible
- Natural Bioavailability Yeast
- Simple transformation
- Genetic engineering tool
- Short segregation time
- Easy fermentation scale-up
- Human edible
- Lyse cells and use enteric capsule Formulated for Oral Delivery ① GM1 Binding Peptide (SEQ ID NO: 8)    ⑥ Dual Agonist (SEQ ID NO: 2)
② Hinge (SEQ ID NO: 11)                 ⑦ Albumin Binding Domain (SEQ ID NO: 7)
③ Maltose Binding Protein               ⑧ His₆ tag (SEQ ID NO: 15)
④ Linker (SEQ ID NO: 12)                ⑨ SV
⑤ Furin Cleavage Site (SEQ ID NO: 14)   ⑩ Cell Penetrating Peptide (SEQ ID NO: 10)

FIG. 4B

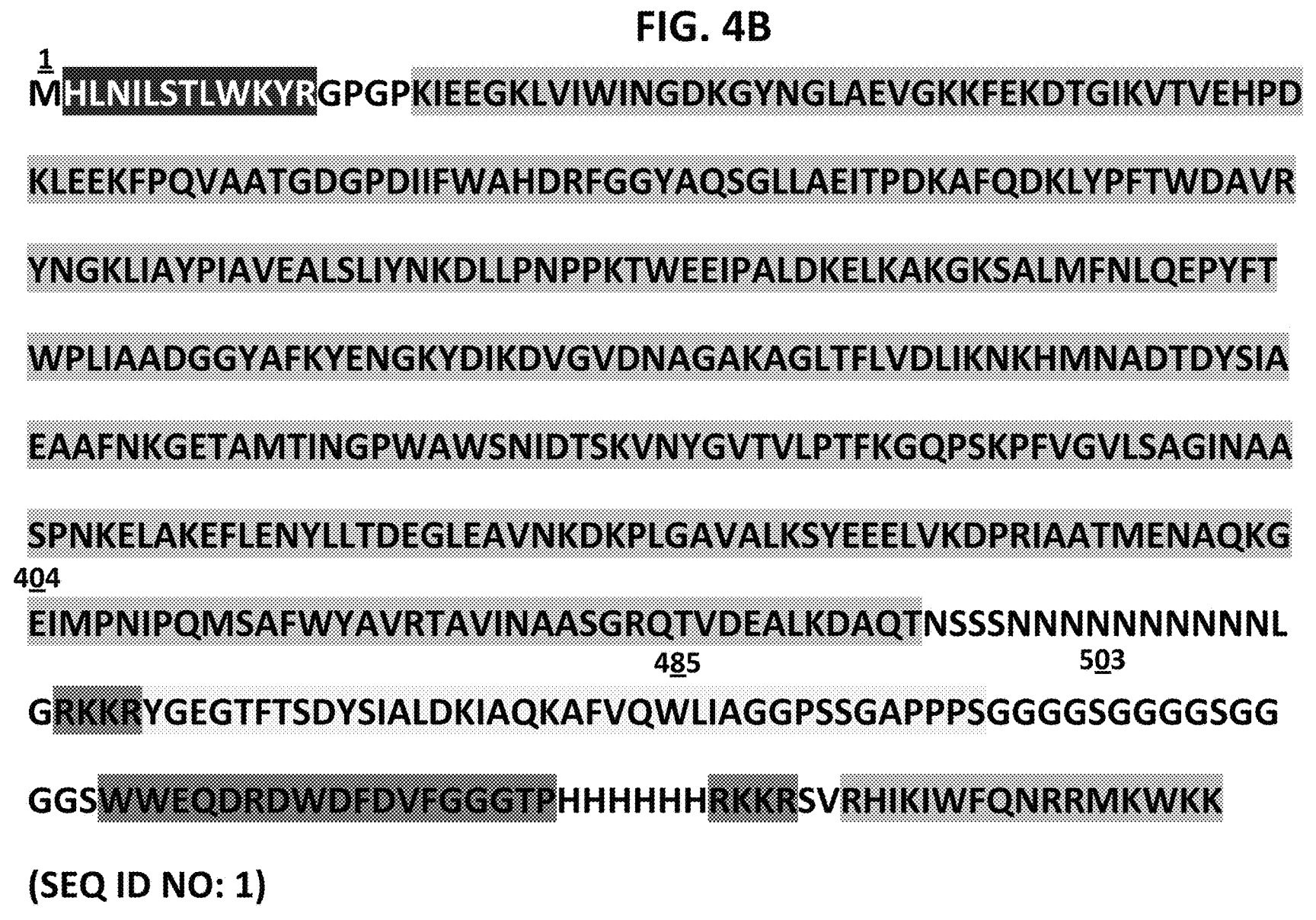

1
MHLNILSTLWKYRGPGPKIEEGKLVIWINGDKGYNGLAEVGKKFEKDTGIKVTVEHPD

KLEEKFPQVAATGDGPDIIFWAHDRFGGYAQSGLLAEITPDKAFQDKLYPFTWDAVR

YNGKLIAYPIAVEALSLYNKDLLPNPPKTWEEIPALDKELKAKGKSALMFNLQEPYFT

WPLIAADGGYAFKYENGKYDIKDVGVDNAGAKAGLTFLVDLIKNKHMNADTDYSIA

EAAFNKGETAMTINGPWAWSNIDTSKVNYGVTVLPTFKGQPSKPFVGVLSAGINAA

SPNKELAKEFLENYLLTDEGLEAVNKDKPLGAVALKSYEEELVKDPRIAATMENAQKG

404
EIMPNIPQMSAFWYAVRTAVINAASGRQTVDEALKDAQTNSSSNNNNNNNNNL
485     503

GRKKRYGEGTFTSDYSIALDKIAQKAFVQWLIAGGPSSGAPPPSGGGGSGGGGGSGG

GGSVVEQDRDVFDVFGGGTPHHHHHHRKKRSVRHIKIWFQNRRMKWKK (SEQ ID NO: 1)

FIG. 4C

YGEGTFTSDYSIALDKIAQKAFVQWLIAGGPSSGAPPPS
(SEQ ID NO: 2)

YGEGTFTSDYSIALDKIAQKAFVQWLIAGGPSSGAPPPSGGGGSGGGGSGGGGS
(SEQ ID NO: 3)

YGEGTFTSDYSIALDKIAQKAFVQWLIAGGPSSGAPPPSGGGGSGGGGSGGGGSWWEQDRDWDFDVFGGGTP
(SEQ ID NO: 4)

YGEGTFTSDYSIALDKIAQKAFVQWLIAGGPSSGAPPPSGGGGSGGGGSGGGGSWWEQDRDWDFDVFGGGTPHHHHHH
(SEQ ID NO: 5)

YGEGTFTSDYSIALDKIAQKAFVQWLIAGGPSSGAPPPSGGGGSGGGGSGGGGSWWEQDRDWDFDVFGGGTPHHHHHHKKK
(SEQ ID NO: 6)

WWEQDRDWDFDVFGGGTP
(SEQ ID NO: 7)

FIG. 6
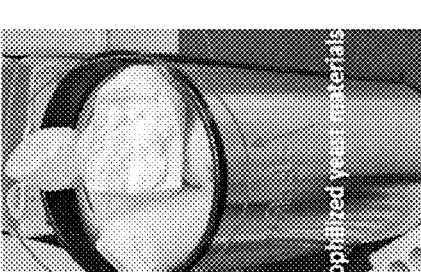
Lyophilizer:
Labconco (FreeZone
2.5L, -84C)
Lyophilized yeast materials
(-80C/0.00mbar) for 3 days
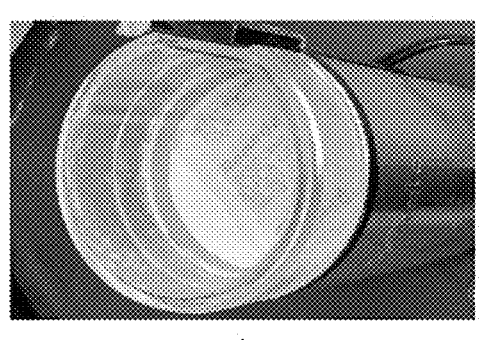
Coffee grinder:
Wancle Electric Coffee Grinder
[Grinding (5 sec) - Break (5sec)] x 4
Enteric capsule:
XPRS Nutra
Size: 0
Material: Gelatin, HPMCP
(Hypromellose phthalate), and water
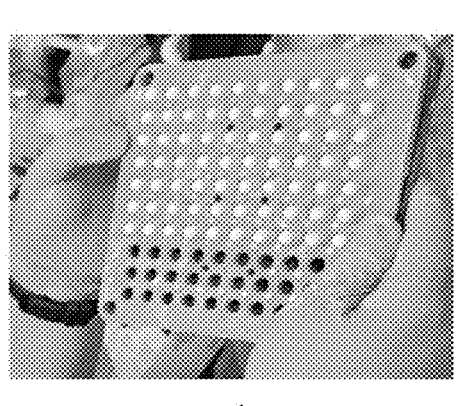
Capsule filter:
CAPSULE-IT Capsule Filler
Amount: 320mg/capsule
Dose (DA): 18.5 ug/capsule
Dose (MBP-DA): 120.3 ug/capsule Baseline data, CGM End of trial data, CGM

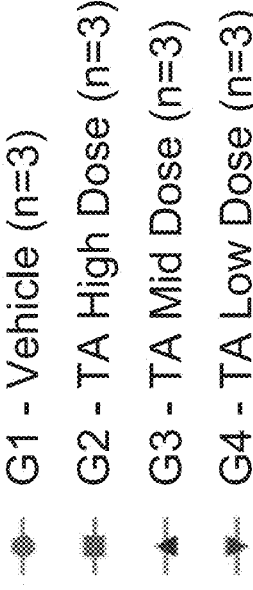
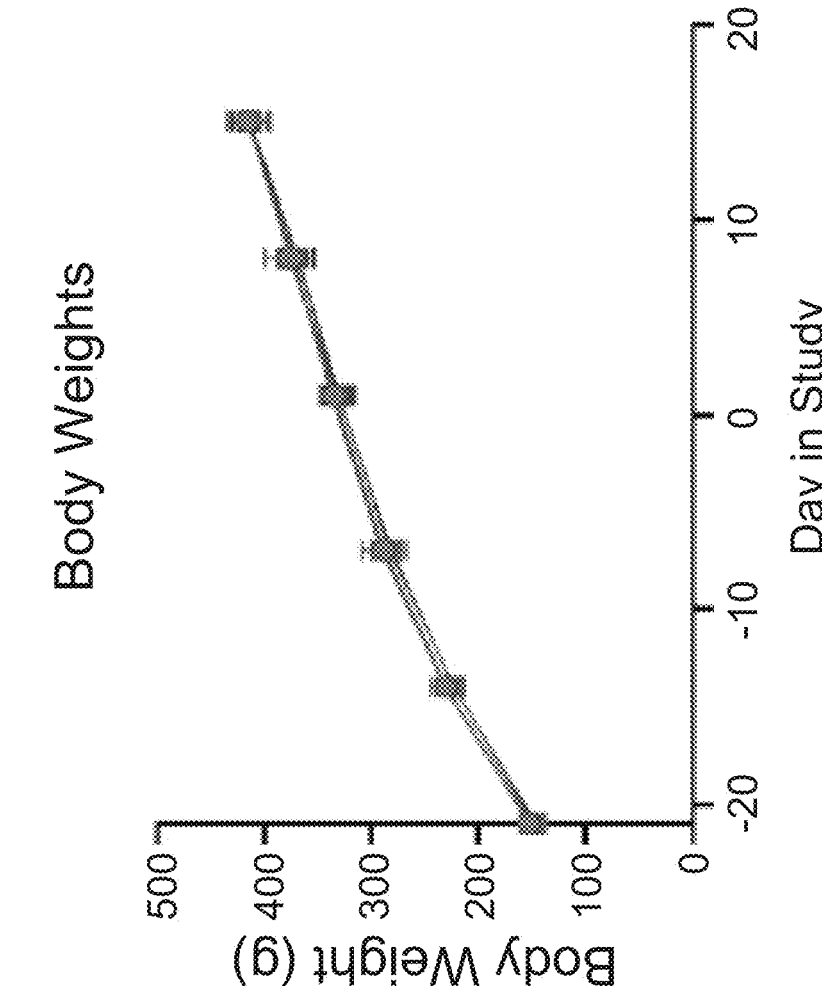
FIG. 10

G1 - Vehicle (n=3)
G2 - TA High Dose (n=3)
G3 - TA Mid Dose (n=3)
G4 - TA Low Dose (n=3)
Start of Dosing

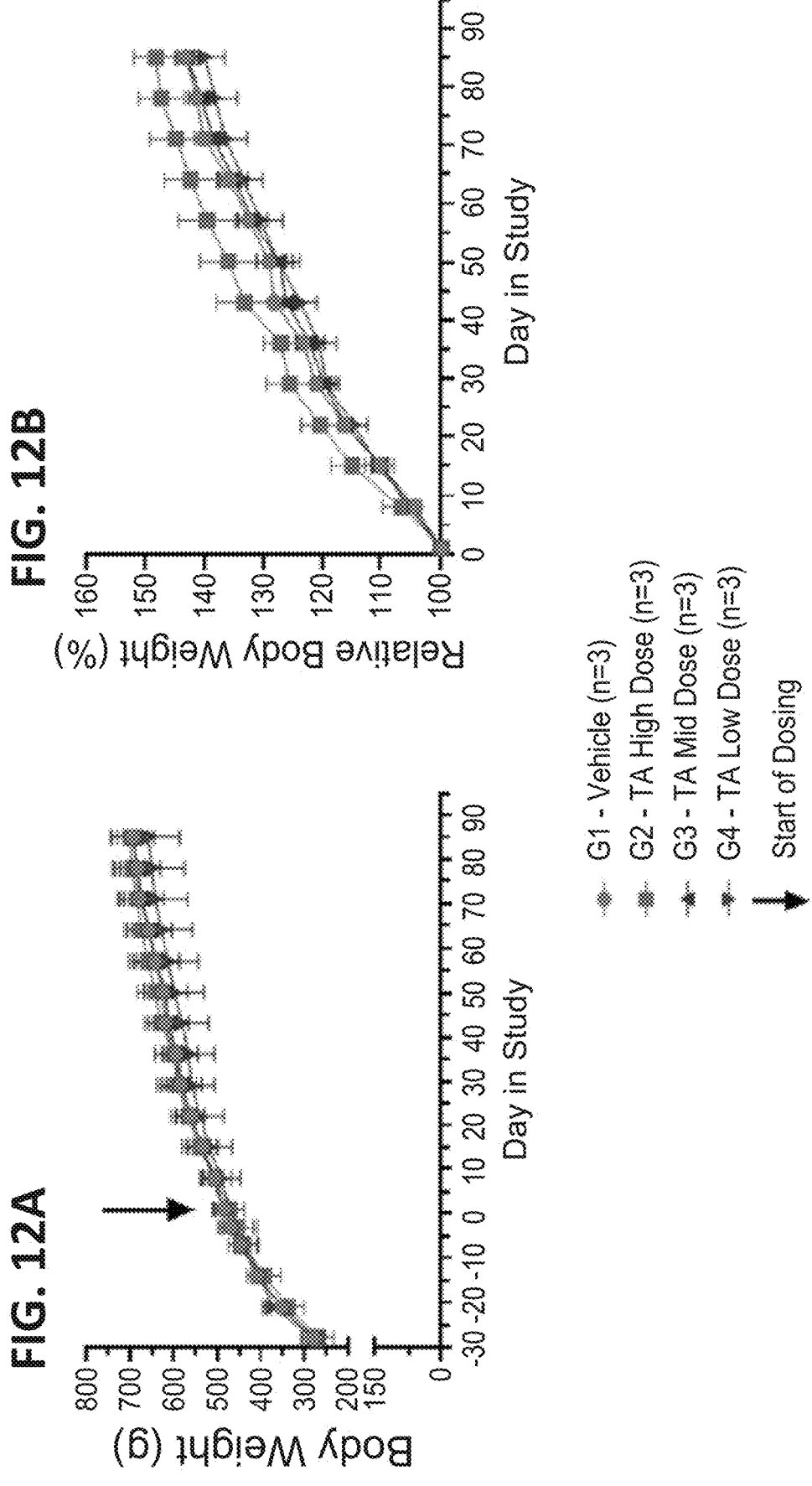

Female Average Body Weights

Male Average Body Weights

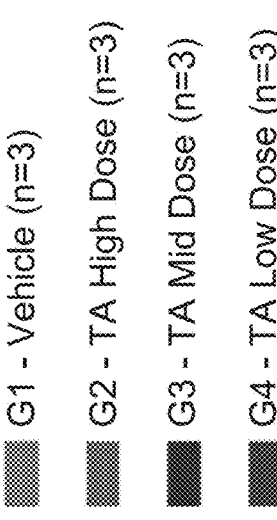
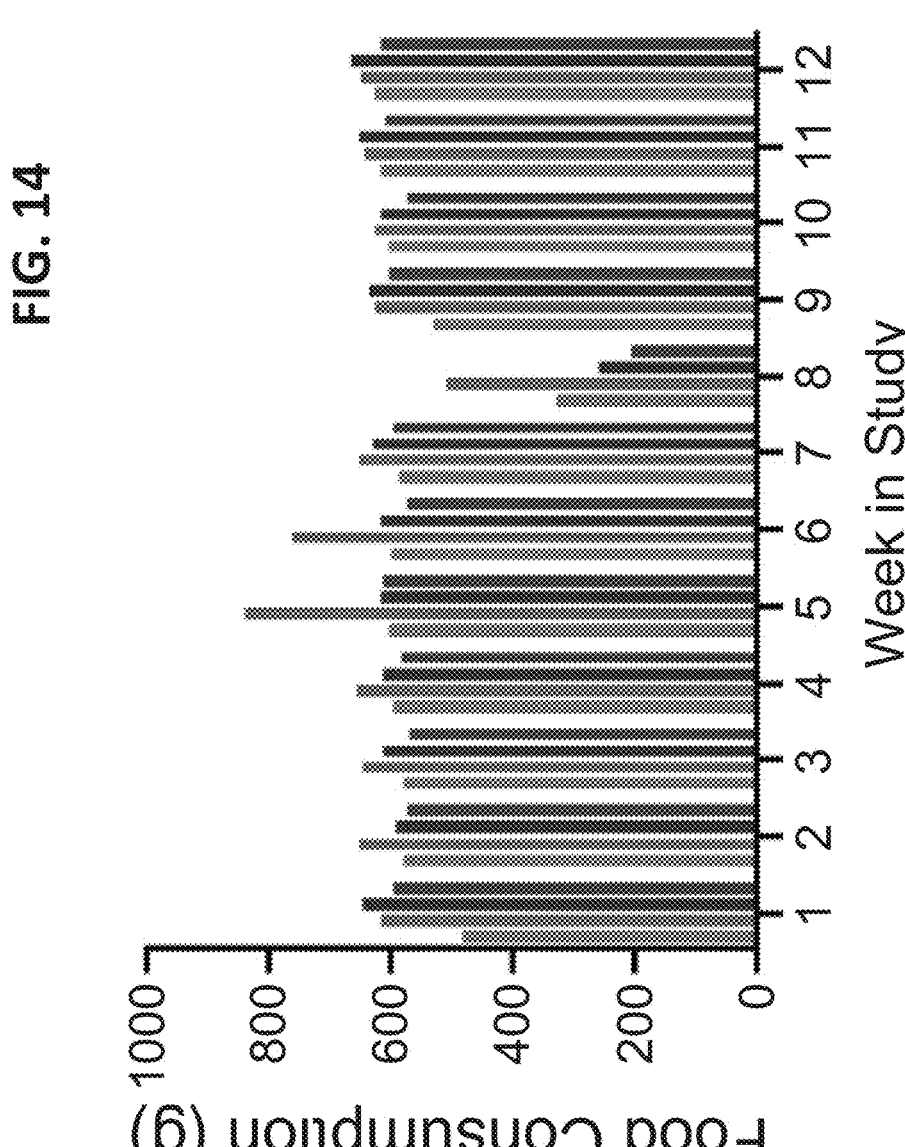
FIG. 14

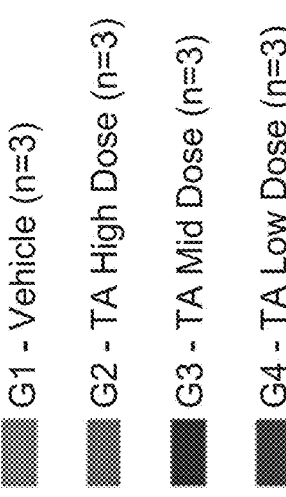
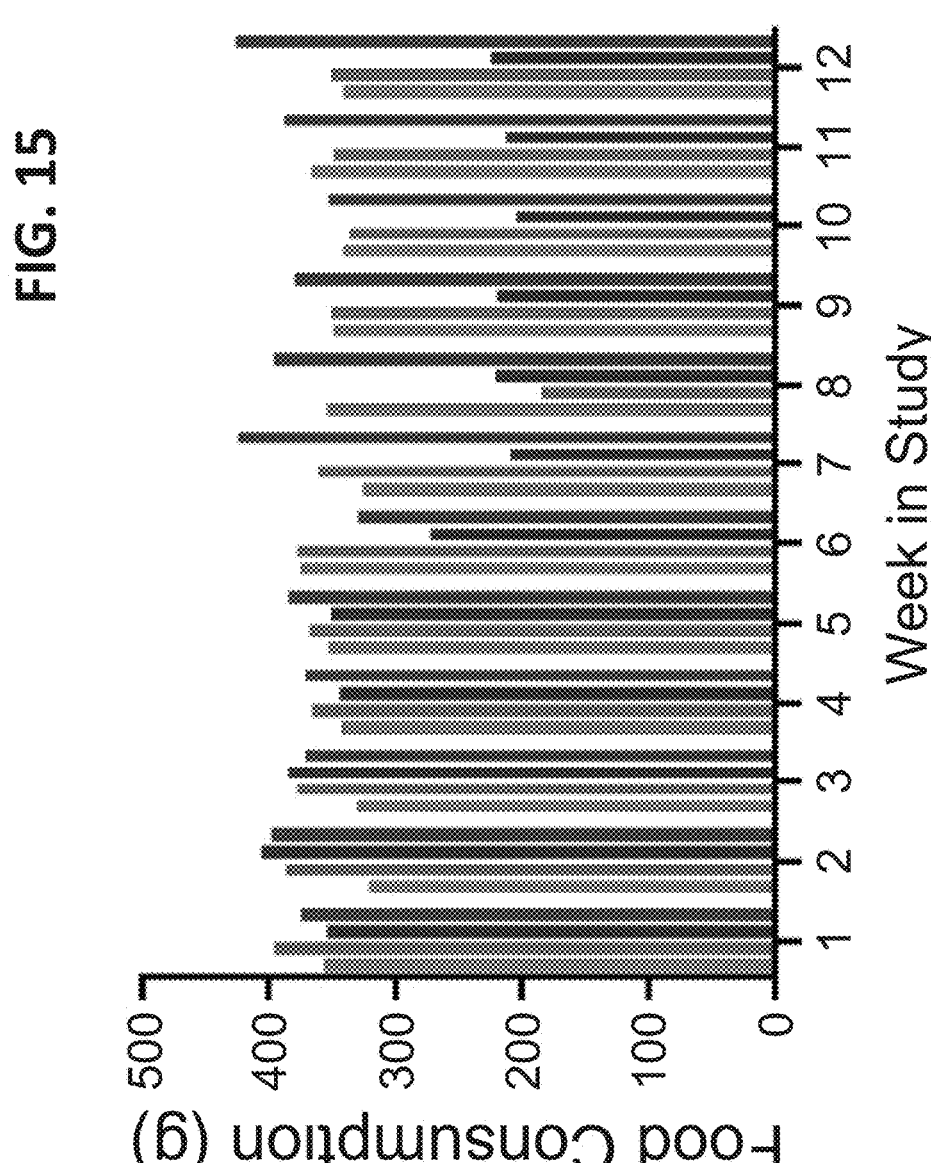
FIG. 15

SEQUENCE LISTING

```
Sequence total quantity: 81
SEQ ID NO: 1          moltype = AA  length = 503
FEATURE               Location/Qualifiers
source                1..503
                      mol_type = protein
                      organism = synthetic construct
SEQUENCE: 1
MHLNILSTLW KYRGPGPKIE EGKLVIWING DKGYNGLAEV GKKFEKDTGI KVTVEHPDKL  60
EEKFPQVAAT GDGPDIIFWA HDRFGGYAQS GLLAEITPDK AFQDKLYPFT WDAVRYNGKL  120
IAYPIAVEAL SLIYNKDLLP NPPKTWEEIP ALDKELKAKG KSALMFNLQE PYFTWPLIAA  180
DGGYAFKYEN GKYDIKDVGV DNAGAKAGLT FLVDLIKNKH MNADTDYSIA EAAFNKGETA  240
MTINGPWAWS NIDTSKVNYG VTVLPTFKGQ PSKPFVGVLS AGINAASPNK ELAKEFLENY  300
LLTDEGLEAV NKDKPLGAVA LKSYEEELVK DPRIAATMEN AQKGEIMPNI PQMSAFWYAV  360
RTAVINAASG RQTVDEALKD AQTNSSSNNN NNNNNNNLGR KKRYGEGTFT SDYSIALDKI  420
AQKAFVQWLI AGGPSSGAPP PSGGGGSGGG GSGGGGSWWE QDRDWDFDVF GGGTPHHHHH  480
```

```
HRKKRSVRHI KIWFQNRRMK WKK                                               503

SEQ ID NO: 2              moltype = AA   length = 39
FEATURE                   Location/Qualifiers
source                    1..39
                          mol_type = protein
                          organism = synthetic construct
SEQUENCE: 2
YGEGTFTSDY SIALDKIAQK AFVQWLIAGG PSSGAPPPS                              39

SEQ ID NO: 3              moltype = AA   length = 54
FEATURE                   Location/Qualifiers
source                    1..54
                          mol_type = protein
                          organism = synthetic construct
SEQUENCE: 3
YGEGTFTSDY SIALDKIAQK AFVQWLIAGG PSSGAPPPSG GGGSGGGGSG GGGS             54

SEQ ID NO: 4              moltype = AA   length = 72
FEATURE                   Location/Qualifiers
source                    1..72
                          mol_type = protein
                          organism = synthetic construct
SEQUENCE: 4
YGEGTFTSDY SIALDKIAQK AFVQWLIAGG PSSGAPPPSG GGGSGGGGSG GGGSWWEQDR       60
DWDFDVFGGG TP                                                           72

SEQ ID NO: 5              moltype = AA   length = 78
FEATURE                   Location/Qualifiers
source                    1..78
                          mol_type = protein
                          organism = synthetic construct
SEQUENCE: 5
YGEGTFTSDY SIALDKIAQK AFVQWLIAGG PSSGAPPPSG GGGSGGGGSG GGGSWWEQDR       60
DWDFDVFGGG TPHHHHHH                                                     78

SEQ ID NO: 6              moltype = AA   length = 82
FEATURE                   Location/Qualifiers
source                    1..82
                          mol_type = protein
                          organism = synthetic construct
SEQUENCE: 6
YGEGTFTSDY SIALDKIAQK AFVQWLIAGG PSSGAPPPSG GGGSGGGGSG GGGSWWEQDR       60
DWDFDVFGGG TPHHHHHHRK KR                                                82

SEQ ID NO: 7              moltype = AA   length = 18
FEATURE                   Location/Qualifiers
source                    1..18
                          mol_type = protein
                          organism = synthetic construct
SEQUENCE: 7
WWEQDRDWDF DVFGGGTP                                                     18

SEQ ID NO: 8              moltype = AA   length = 12
FEATURE                   Location/Qualifiers
source                    1..12
                          mol_type = protein
                          organism = synthetic construct
SEQUENCE: 8
HLNILSTLWK YR                                                           12

SEQ ID NO: 9              moltype = AA   length = 366
FEATURE                   Location/Qualifiers
source                    1..366
                          mol_type = protein
                          organism = synthetic construct
SEQUENCE: 9
KIEEGKLVIW INGDKGYNGL AEVGKKFEKD TGIKVTVEHP DKLEEKFPQV AATGDGPDII       60
FWAHDRFGGY AQSGLLAEIT PDKAFQDKLY PFTWDAVRYN GKLIAYPIAV EALSLIYNKD       120
LLPNPPKTWE EIPALDKELK AKGKSALMFN LQEPYFTWPL IAADGGYAFK YENGKYDIKD       180
VGVDNAGAKA GLTFLVDLIK NKHMNADTDY SIAEAAFNKG ETAMTINGPW AWSNIDTSKV       240
NYGVTVLPTF KGQPSKPFVG VLSAGINAAS PNKELAKEFL ENYLLTDEGL EAVNKDKPLG       300
AVALKSYEEE LVKDPRIAAT MENAQKGEIM PNIPQMSAFW YAVRTAVINA ASGRQTVDEA       360
LKDAQT                                                                  366

SEQ ID NO: 10             moltype = AA   length = 16
FEATURE                   Location/Qualifiers
source                    1..16
                          mol_type = protein
```

-continued

```
                        organism = synthetic construct
SEQUENCE: 10
RHIKIWFQNR RMKWKK                                                              16

SEQ ID NO: 11            moltype = AA   length = 4
FEATURE                  Location/Qualifiers
source                   1..4
                         mol_type = protein
                         organism = synthetic construct
SEQUENCE: 11
GPGP                                                                           4

SEQ ID NO: 12            moltype = AA   length = 16
FEATURE                  Location/Qualifiers
source                   1..16
                         mol_type = protein
                         organism = synthetic construct
SEQUENCE: 12
NSSSNNNNNN NNNNLG                                                              16

SEQ ID NO: 13            moltype = AA   length = 15
FEATURE                  Location/Qualifiers
source                   1..15
                         mol_type = protein
                         organism = synthetic construct
SEQUENCE: 13
GGGGSGGGGS GGGGS                                                               15

SEQ ID NO: 14            moltype = AA   length = 4
FEATURE                  Location/Qualifiers
source                   1..4
                         mol_type = protein
                         organism = synthetic construct
SEQUENCE: 14
RKKR                                                                           4

SEQ ID NO: 15            moltype = AA   length = 6
FEATURE                  Location/Qualifiers
source                   1..6
                         mol_type = protein
                         organism = synthetic construct
SEQUENCE: 15
HHHHHH                                                                         6

SEQ ID NO: 16            moltype = AA   length = 42
FEATURE                  Location/Qualifiers
VARIANT                  1
                         note = H or Y
VARIANT                  2
                         note = A, or G, or aminoisobutyric acid (Aib)
VARIANT                  3
                         note = E or D
VARIANT                  7
                         note = T, S, or I
VARIANT                  9
                         note = D or E
VARIANT                  10
                         note = Y, L, or S
VARIANT                  11
                         note = S or L
VARIANT                  13
                         note = A, or Y, aminoisobutyric acid (Aib), or
                          alpha-methyl-L-Leucine
VARIANT                  14
                         note = M, L, or S
VARIANT                  15
                         note = D or E
VARIANT                  16
                         note = K, G, S, or E
VARIANT                  17
                         note = I, K, Q, R, or E
VARIANT                  19
                         note = Q, A, E, or K
VARIANT                  20
                         note = Q, K, or R
VARIANT                  21
                         note = D, A, or E
VARIANT                  23
                         note = V, I, or L
```

-continued

```
VARIANT              24
                     note = Q, N, E, R or K
VARIANT              27
                     note = L, V, I, K, E, or S
VARIANT              28
                     note = A, S, or R, or aminoisobutyric acid (Aib)
VARIANT              29
                     note = Q, E, K, G, or Y, or aminoisobutyric acid (Aib)
VARIANT              30
                     note = K, G, P, or absent
VARIANT              31
                     note = G, P, S, E, or absent
VARIANT              32
                     note = K, S, or absent
VARIANT              33
                     note = K, S, E, or absent
VARIANT              34
                     note = N, G, A, K, or absent
VARIANT              35
                     note = D, A, P, E, or absent
VARIANT              36
                     note = W, P, K, or absent
VARIANT              37
                     note = K, P, E, or absent
VARIANT              38
                     note = H, P, S, K, or absent
VARIANT              39
                     note = N, S, or absent
VARIANT              40
                     note = I or absent
VARIANT              41
                     note = T or absent
VARIANT              42
                     note = Q or absent
source               1..42
                     mol_type = protein
                     organism = synthetic construct
SEQUENCE: 16
XXXGTFXSXX XIXXXXXAXX XFXXWLXXXX XXXXXXXXXX XX                            42

SEQ ID NO: 17        moltype = AA  length = 39
FEATURE              Location/Qualifiers
source               1..39
                     mol_type = protein
                     organism = synthetic construct
SEQUENCE: 17
YGQGTFTSDY SIYLDKQAQQ AFIEYLLEGG PSSGAPPPS                                39

SEQ ID NO: 18        moltype = AA  length = 11
FEATURE              Location/Qualifiers
source               1..11
                     mol_type = protein
                     organism = synthetic construct
SEQUENCE: 18
DXCLPXWGCL W                                                              11

SEQ ID NO: 19        moltype = AA  length = 13
FEATURE              Location/Qualifiers
source               1..13
                     mol_type = protein
                     organism = synthetic construct
SEQUENCE: 19
XDXCLPXWGC LWX                                                            13

SEQ ID NO: 20        moltype = AA  length = 11
FEATURE              Location/Qualifiers
source               1..11
                     mol_type = protein
                     organism = synthetic construct
SEQUENCE: 20
DICLPRWGCL W                                                              11

SEQ ID NO: 21        moltype = AA  length = 13
FEATURE              Location/Qualifiers
source               1..13
                     mol_type = protein
                     organism = synthetic construct
SEQUENCE: 21
XDICLPRWGC LWX                                                            13
```

-continued

```
SEQ ID NO: 22           moltype = AA  length = 11
FEATURE                 Location/Qualifiers
source                  1..11
                        mol_type = protein
                        organism = synthetic construct
SEQUENCE: 22
DLCLRDWGCL W                                                        11

SEQ ID NO: 23           moltype = AA  length = 15
FEATURE                 Location/Qualifiers
source                  1..15
                        mol_type = protein
                        organism = synthetic construct
SEQUENCE: 23
MEDICLPRWG CLWGD                                                    15

SEQ ID NO: 24           moltype = AA  length = 20
FEATURE                 Location/Qualifiers
source                  1..20
                        mol_type = protein
                        organism = synthetic construct
SEQUENCE: 24
QRLMEDICLP RWGCLWEDDE                                               20

SEQ ID NO: 25           moltype = AA  length = 20
FEATURE                 Location/Qualifiers
source                  1..20
                        mol_type = protein
                        organism = synthetic construct
SEQUENCE: 25
QGLIGDICLP RWGCLWGRSV                                               20

SEQ ID NO: 26           moltype = AA  length = 21
FEATURE                 Location/Qualifiers
source                  1..21
                        mol_type = protein
                        organism = synthetic construct
SEQUENCE: 26
QGLIGDICLP RWGCLWGRSV K                                             21

SEQ ID NO: 27           moltype = AA  length = 15
FEATURE                 Location/Qualifiers
source                  1..15
                        mol_type = protein
                        organism = synthetic construct
SEQUENCE: 27
EDICLPRWGC LWEDD                                                    15

SEQ ID NO: 28           moltype = AA  length = 18
FEATURE                 Location/Qualifiers
source                  1..18
                        mol_type = protein
                        organism = synthetic construct
SEQUENCE: 28
RLMEDICLPR WGCLWEDD                                                 18

SEQ ID NO: 29           moltype = AA  length = 16
FEATURE                 Location/Qualifiers
source                  1..16
                        mol_type = protein
                        organism = synthetic construct
SEQUENCE: 29
MEDICLPRWG CLWEDD                                                   16

SEQ ID NO: 30           moltype = AA  length = 15
FEATURE                 Location/Qualifiers
source                  1..15
                        mol_type = protein
                        organism = synthetic construct
SEQUENCE: 30
MEDICLPRWG CLWED                                                    15

SEQ ID NO: 31           moltype = AA  length = 18
FEATURE                 Location/Qualifiers
source                  1..18
                        mol_type = protein
                        organism = synthetic construct
SEQUENCE: 31
```

```
RLMEDICLAR WGCLWEDD                                              18

SEQ ID NO: 32          moltype = AA  length = 20
FEATURE                Location/Qualifiers
source                 1..20
                       mol_type = protein
                       organism = synthetic construct
SEQUENCE: 32
EWRSFCTRWP AEKSCKPLRG                                            20

SEQ ID NO: 33          moltype = AA  length = 20
FEATURE                Location/Qualifiers
source                 1..20
                       mol_type = protein
                       organism = synthetic construct
SEQUENCE: 33
RAPESFVCYW ETICFERSEQ                                            20

SEQ ID NO: 34          moltype = AA  length = 11
FEATURE                Location/Qualifiers
source                 1..11
                       mol_type = protein
                       organism = synthetic construct
SEQUENCE: 34
EMCYFPGICW M                                                     11

SEQ ID NO: 35          moltype = AA  length = 12
FEATURE                Location/Qualifiers
source                 1..12
                       mol_type = protein
                       organism = synthetic construct
SEQUENCE: 35
FYPSYHSTPQ RP                                                    12

SEQ ID NO: 36          moltype = AA  length = 502
FEATURE                Location/Qualifiers
source                 1..502
                       mol_type = protein
                       organism = synthetic construct
SEQUENCE: 36
MHLNILSTLW KYRGPGPKIE EGKLVIWING DKGYNGLAEV GKKFEKDTGI KVTVEHPDKL   60
EEKFPQVAAT GDGPDIIFWA HDRFGGYAQS GLLAEITPDK AFQDKLYPFT WDAVRYNGKL  120
IAYPIAVEAL SLIYNKDLLP NPPKTWEEIP ALDKELKAKG KSALMFNLQE PYFTWPLIAA  180
DGGYAFKYEN GKYDIKDVGV DNAGAKAGLT FLVDLIKNKH MNADTDYSIA EAAFNKGETA  240
MTINGPWAWS NIDTSKVNYG VTVLPTFKGQ PSKPFVGVLS AGINAASPNK ELAKEFLENY  300
LLTDEGLEAV NKDKPLGAVA LKSYEEELVK DPRIAATMEN AQKGEIMPNI PQMSAFWYAV  360
RTAVINAASG RQTVDEALKD AQTGGGGSGG GGSGGGGSRK KRYGEGTFTS DYSIALDKIA  420
QKAFVQWLIA GGPSSGAPPP SGGGGSGGGG SGGGGSWWEQ DRDWDFDVFG GGTPHHHHHH  480
RKKRSVRHIK IWFQNRRMKW KK                                          502

SEQ ID NO: 37          moltype = AA  length = 39
FEATURE                Location/Qualifiers
source                 1..39
                       mol_type = protein
                       organism = synthetic construct
SEQUENCE: 37
HGEGTFTSDL SKQMEEEAVR LFIEWLKNGG PSSGAPPPS                        39

SEQ ID NO: 38          moltype = AA  length = 32
FEATURE                Location/Qualifiers
source                 1..32
                       mol_type = protein
                       organism = synthetic construct
SEQUENCE: 38
HAEGTFTSDV SSYLEGQAAK EEFIAWLVRG RG                               32

SEQ ID NO: 39          moltype = AA  length = 275
FEATURE                Location/Qualifiers
source                 1..275
                       mol_type = protein
                       organism = synthetic construct
SEQUENCE: 39
HGEGTFTSDV SSYLEEQAAK EFIAWLVKGG GGGGGSGGGG SGGGGSAESK YGPPCPPCPA   60
PEAAGGPSVF LFPPKPKDTL MISRTPEVTC VVVDVSQEDP EVQFNWYVDG VEVHNAKTKP  120
REEQFNSTYR VVSVLTVLHQ DWLNGKEYKC KVSNKGLPSS IEKTISKAKG QPREPQVYTL  180
PPSQEEMTKN QVSLTCLVKG FYPSDIAVEW ESNGQPENNY KTTPPVLDSD GSFFLYSRLT  240
VDKSRWQEGN VFSCSVMHEA LHNHYTQKSL SLSLG                            275

SEQ ID NO: 40          moltype = AA  length = 31
```

```
FEATURE              Location/Qualifiers
source               1..31
                     mol_type = protein
                     organism = synthetic construct
SITE                 2
                     note = aminoisobutyric acid (Aib)
SEQUENCE: 40
HXEGTFTSDV SSYLEGQAAK EFIAWLVRGR G                                     31

SEQ ID NO: 41        moltype = AA  length = 44
FEATURE              Location/Qualifiers
source               1..44
                     mol_type = protein
                     organism = synthetic construct
SEQUENCE: 41
HGEGTFTSDL SKQMEEEAVR LFIEWLKNGG PSSGAPPSKK KKKK                       44

SEQ ID NO: 42        moltype = AA  length = 645
FEATURE              Location/Qualifiers
source               1..645
                     mol_type = protein
                     organism = synthetic construct
SEQUENCE: 42
HGEGTFTSDV SSYLEGQAAK EFIAWLVKGR HGEGTFTSDV SSYLEGQAAK EFIAWLVKGR   60
DAHKSEVAHR FKDLGEENFK ALVLIAFAQY LQQCPFEDHV KLVNEVTEFA KTCVADESAE  120
NCDKSLHTLF GDKLCTVATL RETYGEMADC CAKQEPERNE CFLQHKDDNP NLPRLVRPEV  180
DVMCTAFHDN EETFLKKYLY EIARRHPYFY APELLFFAKR YKAAFTECCQ AADKAACLLP  240
KLDELRDEGK ASSAKQRLKC ASLQKFGERA FKAWAVARLS QRFPKAEFAE VSKLVTDLTK  300
VHTECCHGDL LECADDRADL AKYICENQDS ISSKLKECCE KPLLEKSHCI AEVENDEMPA  360
DLPSLAADFV ESKDVCKNYA EAKDVFLGMF LYEYARRHPD YSVVLLLRLA KTYETTLEKC  420
CAAADPHECY AKVFDEFKPL VEEPQNLIKQ NCELFEQLGE YKFQNALLVR YTKKVPQVST  480
PTLVEVSRNL GKVGSKCCKH PEAKRMPCAE DYLSVVLNQL CVLHEKTPVS DRVTKCCTES  540
LVNRRPCFSA LEVDETYVPK EFNAETFTFH ADICTLSEKE RQIKKQTALV ELVKHKPKAT  600
KEQLKAVMDD FAAFVEKCCK ADDKETCFAE EGKKLVAASQ AALGL                 645

SEQ ID NO: 43        moltype = AA  length = 30
FEATURE              Location/Qualifiers
source               1..30
                     mol_type = protein
                     organism = synthetic construct
SEQUENCE: 43
HAEGTFTSDV SSYLEGQAAK EFIAWLVKGR                                       30

SEQ ID NO: 44        moltype = AA  length = 39
FEATURE              Location/Qualifiers
SITE                 2
                     note = aminoisobutyric acid (Aib)
SITE                 13
                     note = aminoisobutyric acid (Aib)
source               1..39
                     mol_type = protein
                     organism = synthetic construct
SEQUENCE: 44
YXEGTFTSDY SIXLDKIAQK AFVQWLIAGG PSSGAPPPS                             39

SEQ ID NO: 45        moltype = AA  length = 39
FEATURE              Location/Qualifiers
SITE                 1
                     note = N-terminus is is PEGylated
SITE                 2
                     note = D-Alanine
SITE                 14
                     note = Norleucine
source               1..39
                     mol_type = protein
                     organism = synthetic construct
SEQUENCE: 45
HAEGTFTSDL SKQXEEEAVR LFIEWLKQGG PSSGAPPPC                             39

SEQ ID NO: 46        moltype = AA  length = 7
FEATURE              Location/Qualifiers
source               1..7
                     mol_type = protein
                     organism = synthetic construct
SEQUENCE: 46
ENLYFQG                                                                7

SEQ ID NO: 47        moltype = AA  length = 6
FEATURE              Location/Qualifiers
```

-continued

```
source                1..6
                      mol_type = protein
                      organism = synthetic construct
SEQUENCE: 47
LVPRGS                                                                          6

SEQ ID NO: 48         moltype = AA   length = 4
FEATURE               Location/Qualifiers
source                1..4
                      mol_type = protein
                      organism = synthetic construct
SEQUENCE: 48
IEGR                                                                            4

SEQ ID NO: 49         moltype = AA   length = 5
FEATURE               Location/Qualifiers
source                1..5
                      mol_type = protein
                      organism = synthetic construct
SEQUENCE: 49
DDDDK                                                                           5

SEQ ID NO: 50         moltype = AA   length = 5
FEATURE               Location/Qualifiers
source                1..5
                      mol_type = protein
                      organism = synthetic construct
SEQUENCE: 50
GGGGS                                                                           5

SEQ ID NO: 51         moltype = AA   length = 5
FEATURE               Location/Qualifiers
source                1..5
                      mol_type = protein
                      organism = synthetic construct
SEQUENCE: 51
EAAAK                                                                           5

SEQ ID NO: 52         moltype = AA   length = 39
FEATURE               Location/Qualifiers
SITE                  2
                      note = aminoisobutyric acid (Aib)
SITE                  13
                      note = alpha-Methylleucine
SITE                  17
                      note =
                       diacid-C20-gamma-Glutamyl-(2-[2-(2-aminoethoxy)ethoxy]aceti
                       c acid)-Lysine
SITE                  20
                      note = aminoisobutyric acid (Aib)
SITE                  39
                      note = C-terminus is amidated
source                1..39
                      mol_type = protein
                      organism = synthetic construct
SEQUENCE: 52
YXQGTFTSDT SILLDKKAQX AFIEYLLEGG PSSGAPPPS                                      39

SEQ ID NO: 53         moltype = AA   length = 11
FEATURE               Location/Qualifiers
source                1..11
                      mol_type = protein
                      organism = synthetic construct
SEQUENCE: 53
YGRKKRRQRR R                                                                    11

SEQ ID NO: 54         moltype = AA   length = 17
FEATURE               Location/Qualifiers
source                1..17
                      mol_type = protein
                      organism = synthetic construct
SEQUENCE: 54
DRQIKIWFQN RRMKWKK                                                              17

SEQ ID NO: 55         moltype = AA   length = 11
FEATURE               Location/Qualifiers
source                1..11
                      mol_type = protein
                      organism = synthetic construct
```

-continued

```
SEQUENCE: 55
YGRKKRRQRR R                                                      11

SEQ ID NO: 56        moltype = AA  length = 28
FEATURE              Location/Qualifiers
source               1..28
                     mol_type = protein
                     organism = synthetic construct
SEQUENCE: 56
LSTAADMQGV VTDGMASGLD KDYLKPDD                                    28

SEQ ID NO: 57        moltype = AA  length = 13
FEATURE              Location/Qualifiers
source               1..13
                     mol_type = protein
                     organism = synthetic construct
SEQUENCE: 57
ETFSDLWKLL PEN                                                    13

SEQ ID NO: 58        moltype = AA  length = 7
FEATURE              Location/Qualifiers
source               1..7
                     mol_type = protein
                     organism = synthetic construct
SEQUENCE: 58
RRRRRRR                                                           7

SEQ ID NO: 59        moltype = AA  length = 12
FEATURE              Location/Qualifiers
source               1..12
                     mol_type = protein
                     organism = synthetic construct
SITE                 2
                     note = 6-aminohexanoic acid
SITE                 5
                     note = 6-aminohexanoic acid
SITE                 8
                     note = 6-aminohexanoic acid
SITE                 11
                     note = 6-aminohexanoic acid
SEQUENCE: 59
RXRRXRRXRR XR                                                     12

SEQ ID NO: 60        moltype = AA  length = 13
FEATURE              Location/Qualifiers
source               1..13
                     mol_type = protein
                     organism = synthetic construct
SEQUENCE: 60
YGRKKRRQRR RVR                                                    13

SEQ ID NO: 61        moltype = AA  length = 11
FEATURE              Location/Qualifiers
source               1..11
                     mol_type = protein
                     organism = synthetic construct
SEQUENCE: 61
YARVRRRGPR R                                                      11

SEQ ID NO: 62        moltype = AA  length = 9
FEATURE              Location/Qualifiers
source               1..9
                     mol_type = protein
                     organism = synthetic construct
SEQUENCE: 62
RRRRRRRRR                                                         9

SEQ ID NO: 63        moltype = AA  length = 7
FEATURE              Location/Qualifiers
source               1..7
                     mol_type = protein
                     organism = synthetic construct
SEQUENCE: 63
KKSRALF                                                           7

SEQ ID NO: 64        moltype = AA  length = 9
FEATURE              Location/Qualifiers
source               1..9
                     mol_type = protein
```

-continued

```
                        organism = synthetic construct
SEQUENCE: 64
RRRRRRRRR                                                                9

SEQ ID NO: 65          moltype = AA   length = 16
FEATURE                Location/Qualifiers
source                 1..16
                       mol_type = protein
                       organism = synthetic construct
SEQUENCE: 65
RQIKIWFQNR RMKWKK                                                        16

SEQ ID NO: 66          moltype = AA   length = 11
FEATURE                Location/Qualifiers
source                 1..11
                       mol_type = protein
                       organism = synthetic construct
SEQUENCE: 66
YGRKKRRQRR R                                                             11

SEQ ID NO: 67          moltype = AA   length = 21
FEATURE                Location/Qualifiers
source                 1..21
                       mol_type = protein
                       organism = synthetic construct
SITE                   21
                       note = C-terminus is amidated
SEQUENCE: 67
AGYLLGKINL KALAALAKKI L                                                  21

SEQ ID NO: 68          moltype = AA   length = 18
FEATURE                Location/Qualifiers
source                 1..18
                       mol_type = protein
                       organism = synthetic construct
SEQUENCE: 68
KLALKLALKA LKAALKLA                                                      18

SEQ ID NO: 69          moltype = AA   length = 21
FEATURE                Location/Qualifiers
source                 1..21
                       mol_type = protein
                       organism = synthetic construct
SEQUENCE: 69
KETWWETWWT EWSQPKKKRK V                                                  21

SEQ ID NO: 70          moltype = AA   length = 11
FEATURE                Location/Qualifiers
source                 1..11
                       mol_type = protein
                       organism = synthetic construct
SEQUENCE: 70
YARAAARQAR A                                                             11

SEQ ID NO: 71          moltype = AA   length = 5
FEATURE                Location/Qualifiers
source                 1..5
                       mol_type = protein
                       organism = synthetic construct
SEQUENCE: 71
KKKKK                                                                    5

SEQ ID NO: 72          moltype = AA   length = 5
FEATURE                Location/Qualifiers
source                 1..5
                       mol_type = protein
                       organism = synthetic construct
SEQUENCE: 72
RRRRR                                                                    5

SEQ ID NO: 73          moltype = AA   length = 82
FEATURE                Location/Qualifiers
source                 1..82
                       mol_type = protein
                       organism = synthetic construct
SEQUENCE: 73
YGEGTFTSDY SIALDKIAQK AFVQWLIAGG PSSGAPPPSG GGGSGGGGSG GGGSWWEQDR  60
DWDFDVFGGG TPHHHHHRK KR                                                  82
```

-continued

```
SEQ ID NO: 74          moltype = AA  length = 18
FEATURE                Location/Qualifiers
source                 1..18
                       mol_type = protein
                       organism = synthetic construct
REPEAT                 1..3
                       note = single repeat of HHH
VARIANT                4..18
                       note = up to 5 copies of HHH repeat may be absent
SEQUENCE: 74
HHHHHHHHHH HHHHHHHH                                                    18

SEQ ID NO: 75          moltype = AA  length = 15
FEATURE                Location/Qualifiers
source                 1..15
                       mol_type = protein
                       organism = synthetic construct
SEQUENCE: 75
VWRLLAPPFS NRLLP                                                       15

SEQ ID NO: 76          moltype = AA  length = 14
FEATURE                Location/Qualifiers
source                 1..14
                       mol_type = protein
                       organism = synthetic construct
SEQUENCE: 76
WRLLAPPFSN RLLP                                                        14

SEQ ID NO: 77          moltype = AA  length = 14
FEATURE                Location/Qualifiers
source                 1..14
                       mol_type = protein
                       organism = synthetic construct
VARIANT                1
                       note = W or F
VARIANT                5
                       note = P or any amino acid
VARIANT                6
                       note = P or any amino acid
VARIANT                11
                       note = R or any amino acid
VARIANT                12
                       note = R or any amino acid
SEQUENCE: 77
XRXLXXXFXX XXXP                                                        14

SEQ ID NO: 78          moltype = AA  length = 13
FEATURE                Location/Qualifiers
source                 1..13
                       mol_type = protein
                       organism = synthetic construct
SEQUENCE: 78
GRKKRRQRRR PPQ                                                         13

SEQ ID NO: 79          moltype = AA  length = 4
FEATURE                Location/Qualifiers
source                 1..4
                       mol_type = protein
                       organism = synthetic construct
SEQUENCE: 79
GGGG                                                                    4

SEQ ID NO: 80          moltype = AA  length = 17
FEATURE                Location/Qualifiers
source                 1..17
                       mol_type = protein
                       organism = synthetic construct
SEQUENCE: 80
GGGGSGGGGS GGGGSAL                                                     17

SEQ ID NO: 81          moltype = AA  length = 16
FEATURE                Location/Qualifiers
source                 1..16
                       mol_type = protein
                       organism = synthetic construct
SEQUENCE: 81
GGGGSGGGGS GGGGSA                                                      16
```

ORAL BIODELIVERY PLATFORM

CROSS-REFERENCE TO RELATED APPLICATIONS

This application is a continuation of International Application No. PCT/US2025/049519, filed Oct. 3, 2025, which claims the benefit of U.S. Provisional Patent Application No. 63/703,206 filed Oct. 4, 2024, U.S. Provisional Patent Application No. 63/722,040 filed Nov. 18, 2024, U.S. Provisional Patent Application No. 63/703,207 filed Oct. 4, 2024, U.S. Provisional Patent Application No. 63/722,039 filed Nov. 18, 2024, and U.S. Provisional Patent Application No. 63/860,426 filed Aug. 8, 2025, the entire contents of each of which are incorporated herein by reference in their entireties.

REFERENCE TO AN ELECTRONIC SEQUENCE LISTING

The contents of the electronic sequence listing (BDRV_006_04US_SeqList_ST26.xml; Size: 95,295 bytes; and Date of Creation: Feb. 26, 2026) are herein incorporated by reference in their entirety.

FIELD OF THE DISCLOSURE

The present disclosure relates to biodelivery platforms for the oral delivery of molecular cargo to a subject in need thereof. Also provided are methods of delivering a molecular cargo with biodelivery platforms of the disclosure and methods of making biodelivery platforms of the disclosure. In some aspects, the disclosure relates to multi-incretin agonist mimetics targeting, e.g., GLP-1 and/or GIP receptors, and their use in treating conditions such as obesity, diabetes, and related metabolic diseases.

BACKGROUND

Oral administration remains the most preferred route for drug delivery due to its convenience, patient compliance, and cost-effectiveness. However, the gastrointestinal (GI) tract presents significant challenges for the delivery of many therapeutics. Therapeutic molecules such as peptides and proteins are highly susceptible to enzymatic degradation in the stomach and upper intestines, and often exhibit poor permeability across the intestinal epithelium, resulting in low bioavailability.

There remains an ongoing and unmet need for improved biodelivery systems to enhance the stability and efficacy of orally administered molecular cargo.

BRIEF SUMMARY

The present disclosure addresses long-standing obstacles associated with the oral administration of biologically active macromolecules, particularly therapeutic peptides and proteins. As noted in the Background, conventional peptide therapeutics administered orally are prone to rapid enzymatic degradation within the gastrointestinal tract and suffer from poor epithelial permeability, resulting in low systemic exposure and reduced therapeutic efficacy. The disclosure provided herein overcomes these limitations by, inter alia, providing engineered fusion proteins and associated biodelivery platforms that enhance stability, promote absorption across the intestinal epithelium, and release the therapeutic cargo in active form once in systemic circulation.

In an embodiment, the disclosure provides an oral biodelivery platform comprising engineered fusion proteins that overcome the instability and poor absorption traditionally associated with peptide therapeutics. In aspects, the fusion proteins include a molecular cargo domain, such as an incretin agonist, operably linked to one or more transduction domains that promote epithelial uptake, and may further comprise protease cleavage sites for controlled release, solubility-enhancing tags, and albumin-binding domains for extended half-life. Nucleic acids, vectors, and host cells encoding such fusion proteins are provided, as are formulations in which lyophilized host cells expressing the fusion protein are encapsulated for oral administration. Methods of treatment using these compositions enable effective delivery of molecular cargo, e.g. incretin agonists and other therapeutic peptides to treat metabolic disorders such as obesity and diabetes.

In one aspect, the disclosure provides fusion proteins comprising (a) a molecular cargo domain, such as an incretin agonist, and (b) at least one transduction domain configured to facilitate intestinal uptake. Certain embodiments further include dual transduction domains, for example, a GM1-binding peptide at one terminus and a cell-penetrating peptide at the other, thereby leveraging complementary uptake mechanisms to maximize oral bioavailability. In aspects, the fusion proteins may also incorporate additional functional elements—such as protease cleavage sites, solubility-enhancing domains, or albumin-binding domains—to improve folding, stability, pharmacokinetics, and controlled release of the therapeutic moiety.

In another aspect, the disclosure provides nucleic acids, vectors, and host cells encoding such fusion proteins, enabling scalable recombinant production in systems such as *Saccharomyces cerevisiae*. Host cells expressing the fusion proteins may be dried, lyophilized, or ground into powders and subsequently formulated into capsules or tablets for oral administration. The resulting pharmaceutical compositions, or dietary supplements, afford a practical and cost-effective means of delivering molecular cargo, e.g. incretin agonists and related therapeutic peptides, while maintaining patient convenience and compliance.

Various methods of treatment are also provided. These methods include administering an effective amount of the fusion protein, host cell, or pharmaceutical composition to subjects in need thereof, e.g., patients with metabolic disorders such as obesity, diabetes, insulin resistance, or related cardiovascular conditions. In embodiments, oral administration of the disclosed biodelivery platforms induces weight loss, increases insulin sensitivity, and improves glycemic control.

Collectively, these various features provide an integrated solution to the problems of peptide instability and poor intestinal absorption, enabling the generation of a robust platform for the oral delivery of molecular cargo that overcomes the problems of the art.

In some embodiments, the techniques described herein relate to a fusion protein including: a) a molecular cargo domain; and b) at least one transduction domain.

In some embodiments, the techniques described herein relate to a fusion protein, wherein the fusion protein includes a transduction domain at the N-terminus and/or C-terminus of the fusion protein.

In some embodiments, the techniques described herein relate to a fusion protein, wherein the fusion protein includes a transduction domain at each of the N-terminus and the C-terminus of the fusion protein.

In some embodiments, the techniques described herein relate to a fusion protein, wherein the fusion protein includes a transduction domain including a GM-1 binding peptide at one terminus and a transduction domain including a CPP at the other terminus.

In some embodiments, the techniques described herein relate to a fusion protein, wherein at least one transduction domain includes a GM1 receptor binding protein (GM1-BP), transferrin, antibody fragment crystallizable region (Fc region), a dendritic cell peptide (DCpep), or a cell penetrating peptide (CPP).

In some embodiments, the techniques described herein relate to a fusion protein, wherein at least one transduction domain includes a GM1-BP selected from: Cholera Toxin B subunit (CTB), Heat-labile Enterotoxin B subunit (LTB), and an anti-GM1 antibody.

In some embodiments, the techniques described herein relate to a fusion protein, wherein at least one transduction domain includes an amino acid sequence having at least 85% sequence identity to the amino acid sequence of SEQ ID NO: 8 (HLNILSTLWKYR).

In some embodiments, the techniques described herein relate to a fusion protein, wherein at least one transduction domain includes the amino acid sequence of SEQ ID NO: 8 (HLNILSTLWKYR).

In some embodiments, the techniques described herein relate to a fusion protein, wherein at least one transduction domain includes a CPP.

In some embodiments, the techniques described herein relate to a fusion protein, wherein at least one transduction domain includes a CPP selected from the list consisting of: TAT, ATX-101, AM-111, P28, ALRN-6924, R7, (R-Ahx-R)4, TransMTS, MTS, AVB-620 (ACPP), Pepducin, BT1718, PEP-010, ATP128, PTD4, and a charged oligo peptide.

In some embodiments, the techniques described herein relate to a fusion protein, wherein at least one transduction domain includes a CPP that binds to PDX-1.

In some embodiments, the techniques described herein relate to a fusion protein, wherein at least one transduction domain includes an amino acid sequence having at least 85% sequence identity to the amino acid sequence of SEQ ID NO: 10 (RHIKIWFQNRRMKWKK).

In some embodiments, the techniques described herein relate to a fusion protein, wherein at least one transduction domain includes the amino acid sequence of SEQ ID NO: 10 (RHIKIWFQNRRMKWKK).

In some embodiments, the techniques described herein relate to a fusion protein, wherein the fusion protein includes a solubility-enhancing domain.

In some embodiments, the techniques described herein relate to a fusion protein, wherein the solubility-enhancing domain includes a domain selected from the list consisting of: maltose-binding protein (MBP), cross-linked amylose/maltose, glutathione S-transferase (GST), SlyD, thioredoxin (Trx), galactose, ubiquitin, N-utilization substance A (NusA), small ubiquitin-like modifier (SUMO), and green fluorescent protein (GFP).

In some embodiments, the techniques described herein relate to a fusion protein or claim 15, wherein the solubility-enhancing domain includes MBP.

In some embodiments, the techniques described herein relate to a fusion protein, wherein the solubility-enhancing domain includes a sequence having at least 85% sequence identity to the amino acid sequence of SEQ ID NO: 9.

In some embodiments, the techniques described herein relate to a fusion protein, wherein the solubility-enhancing domain includes the amino acid sequence of SEQ ID NO: 9.

In some embodiments, the techniques described herein relate to a fusion protein, wherein the fusion protein includes an albumin binding domain.

In some embodiments, the techniques described herein relate to a fusion protein, wherein the albumin binding domain binds to an albumin serum protein or at least a fragment, epitope, or domain thereof.

In some embodiments, the techniques described herein relate to a fusion protein, wherein the albumin binding domain includes an amino acid sequence having at least 85% sequence identity to the amino acid sequence of SEQ ID NO: 7 (WWEQDRDWDFDVFGGGTP).

In some embodiments, the techniques described herein relate to a fusion protein, wherein the albumin binding domain includes the amino acid sequence of SEQ ID NO: 7 (WWEQDRDWDFDVFGGGTP).

In some embodiments, the techniques described herein relate to a fusion protein, wherein the fusion protein includes at least one protease cleavage site.

In some embodiments, the techniques described herein relate to a fusion protein, wherein the fusion protein includes two protease cleavage sites.

In some embodiments, the techniques described herein relate to a fusion protein, wherein the fusion protein includes a protease cleavage site N-terminally and C-terminally from the molecular cargo domain.

In some embodiments, the techniques described herein relate to a fusion protein, wherein the fusion protein includes a protease cleavage site between the molecular cargo domain and a transduction domain.

In some embodiments, the techniques described herein relate to a fusion protein, wherein the protease cleavage site(s) are selected from: furin, BACE1, BACE2, Cathepsin D, Cathepsin E, Chymosin (or "rennin"), Napsin-A, Nepenthesin, Pepsin, Presenilin, Renin, Papain, bromelain, cathepsin K and, calpain, Caspase-1, separase, Adenain, Pyroglutamyl-peptidase I, Hepatitis C virus peptidase 2, Sindbis virus-type nsP2 peptidase, Dipeptidyl-peptidase VI, DeSI-1 peptidase, TEV protease, Amidophosphoribosyltransferase precursor, Gamma-glutamyl hydrolase, Hedgehog protein, DmpA aminopeptidase, Subtilisin, Prolyl oligopeptidase, D-Ala-D-Ala peptidase C, Signal peptidase I, Cytomegalovirus assembling, Lon-A peptidase, Clp protease, Phage KIF endosialidase CIMCD self-cleaving protein, Nucleoporin 145, Lactoferrin, Murein tetrapeptidase LD-carboxypeptidase, Rhomboid-1, Chymotrypsin A, Penicillin G acylase precursor, Dipeptidase E, DmpA aminopeptidase, MMP 1 to MMP 28, Interstitial collagenase, Gelatinase-A, 72 kDa gelatinase, Stromelysin 1, Matrilysin, PUMP 1, Neutrophil collagenase, Gelatinase-B, 92 kDa gelatinase, Stromelysin 2, Stromelysin 3, Macrophage metalloelastase, Collagenase 3, MT1-MMP, MT2-MMP, MT3-MMP, MT4-MMP, Collagenase 4, RASI-1, stromelysin-4, Enamelysin, X-MMP, CA-MMP, MT5-MMP, MT6-MMP, Matrilysin-2, endometase, MMP-22, C-MMP, and Epilysin cleavage sites.

In some embodiments, the techniques described herein relate to a fusion protein, wherein at least one protease cleavage site is a furin cleavage site.

In some embodiments, the techniques described herein relate to a fusion protein, wherein at least one protease cleavage site includes the amino acid sequence of SEQ ID NO: 14 (RKKR).

In some embodiments, the techniques described herein relate to a fusion protein, wherein the fusion protein includes two protease cleavage sites including the amino acid sequence of SEQ ID NO: 14 (RKKR).

In some embodiments, the techniques described herein relate to a fusion protein, further including an affinity tag.

In some embodiments, the techniques described herein relate to a fusion protein, wherein the affinity tag includes a histidine tag.

In some embodiments, the techniques described herein relate to a fusion protein, wherein the histidine tag includes the amino acid sequence of (HHH)n (SEQ ID NO: 74), wherein n is selected from 1, 2, 3, 4, 5, and 6.

In some embodiments, the techniques described herein relate to a fusion protein, wherein the molecular cargo domain includes a therapeutic peptide selected from the list consisting of: hormonal peptides, cardiovascular peptides, neurological peptides, pain-modulating peptides, antimicrobial peptides, anti-infective peptides, immunomodulatory peptides, oncological peptides, gastrointestinal peptides, dermatological peptides, wound-healing peptides, musculoskeletal peptides, growth-modulating peptides, metabolic peptides, appetite-regulating peptides, diagnostic peptides, an structural peptides.

In some embodiments, the techniques described herein relate to a fusion protein, wherein the molecular cargo domain includes an incretin agonist.

In some embodiments, the techniques described herein relate to a fusion protein, wherein the incretin agonist is selected from the list consisting of: a glucagon-like peptide 1 (GLP-1) receptor (GLP-1R) agonist, a gastric inhibitory polypeptide (GIP) receptor (GIP-R) agonist, a dual GLP-1R and GIP-1R incretin agonist, and a triple incretin agonist.

In some embodiments, the techniques described herein relate to a fusion protein, wherein the incretin agonist mimetic includes the sequence of: X1-X2-X3-Gly-Thr-Phe-X7-Ser-X9-X10-X11-Ile-X13-X14-X15-X16-X17-Ala-X19-X20-X21-X22-X23-X24-Trp-Leu-X27-X28-X29-X30-X31-X32-X33-X34-X35-X36-X37-X38-X39-X40-X41-X42 (SEQ ID NO: 16), wherein X1 is His or Tyr; X2 is Ala, Gly, or aminoisobutyric acid (Aib); X3 is Glu or Asp; X7 is Thr, Ser, or Ile; X9 is Asp or Glu; X10 is Tyr, Leu, or Ser; X11 is Ser or Leu; X13 is Ala, Tyr, Aib, or alpha-methyl-L-leucine (αMeL); X14 is Met, Leu, or Ser; X15 is Asp or Glu; X16 is Lys, Gly, Ser, or Glu; X17 is Ile, Lys, Gln, Arg, or Glu; X19 is Gln, Ala, Glu, or Lys; X20 is Gln, Lys, or Arg; X21 is Asp, Ala, or Glu; X22 is Phe; X23 is Val, Ile, or Leu; X24 is Gln, Asn, Glu, Arg or Lys; X27 is Leu, Val, Ile, Lys, Glu, or Ser; X28 is Ala, Ser, Arg, or Aib; X29 is Gln, Glu, Lys, Gly, Tyr, or Aib; X30 is Lys, Gly, Pro, or absent; X31 is Gly, Pro, Ser, Glu, or absent; X32 is Lys, Ser, or absent; X33 is Lys, Ser, Glu, or absent; X34 is Asn, Gly, Ala, Lys, or absent; X35 is Asp, Ala, Pro, Glu, or absent; X36 is Trp, Pro, Lys, or absent; X37 is Lys, Pro, Glu, or absent; X38 is His, Pro, Ser, Lys, or absent; X39 is Asn, Ser, or absent; X40 is Ile or absent; X41 is Thr or absent; and X42 is Gln or absent.

In some embodiments, the techniques described herein relate to a fusion protein, wherein the incretin agonist includes an amino acid sequence having at least 85% sequence identity to the amino acid sequence of SEQ ID NO: 2 (YGEGTFTSDY SIALDKIAQK AFVQWLIAGG PSSGAPPPS).

In some embodiments, the techniques described herein relate to a fusion protein, wherein the incretin agonist includes the amino acid sequence of SEQ ID NO: 2 (YGEGTFTSDY SIALDKIAQK AFVQWLIAGG PSSGAPPPS).

In some embodiments, the techniques described herein relate to a fusion protein, wherein the incretin agonist includes an amino acid sequence having at least 85% sequence identity to the amino acid sequence of SEQ ID NO: 17 (YGQGTFTSDY SIYLDKQAQQ AFIEYLLEGG PSSGAPPPS).

In some embodiments, the techniques described herein relate to a fusion protein, wherein the incretin agonist includes the amino acid sequence of SEQ ID NO: 17 (YGQGTFTSDY SIYLDKQAQQ AFIEYLLEGG PSSGAPPPS).

In some embodiments, the techniques described herein relate to a fusion protein, wherein the fusion protein includes, from N-terminus to C-terminus, a first transduction domain, a first protease cleavage site, a molecular cargo domain, a second protease cleavage site, and a second transduction domain.

In some embodiments, the techniques described herein relate to a fusion protein, wherein the fusion protein includes, from N-terminus to C-terminus, a first transduction domain, a solubility domain, a first protease cleavage site, a molecular cargo domain, a second protease cleavage site, and a second transduction domain.

In some embodiments, the techniques described herein relate to a fusion protein, wherein the fusion protein includes, from N-terminus to C-terminus, a first transduction domain including a GM1-BP or a CPP, a first protease cleavage site, a molecular cargo domain, a second protease cleavage site, and a second transduction domain including a GM1-BP or a CPP.

In some embodiments, the techniques described herein relate to a fusion protein, wherein the fusion protein includes a therapeutic moiety including the molecular cargo domain, wherein the fusion protein includes a non-therapeutic moiety including a transduction domain, and wherein the therapeutic moiety and the non-therapeutic moiety are separated by a protease cleavage site.

In some embodiments, the techniques described herein relate to a fusion protein, wherein the fusion protein includes an amino acid sequence having at least 85% sequence identity to the amino acid sequence of SEQ ID NO: 1.

In some embodiments, the techniques described herein relate to a fusion protein, wherein the fusion protein includes the amino acid sequence of SEQ ID NO: 1.

In some embodiments, the techniques described herein relate to a nucleic acid encoding the fusion protein.

In some embodiments, the techniques described herein relate to a vector encoding the fusion protein or including the nucleic acid.

In some embodiments, the techniques described herein relate to a host cell including the fusion protein, the nucleic acid, or the vector.

In some embodiments, the techniques described herein relate to a host cell, wherein the host cell is an algal, plant, or yeast cell.

In some embodiments, the techniques described herein relate to a host cell, wherein the host cell is a *Saccharomyces cerevisiae* cell.

In some embodiments, the techniques described herein relate to a host cell, wherein the host cell has been dried, lyophilized, and/or ground into a powder.

In some embodiments, the techniques described herein relate to a pharmaceutical composition including: the fusion protein or the host cell; and a pharmaceutically acceptable excipient.

In some embodiments, the techniques described herein relate to a method of producing a fusion protein of the disclosure; comprising recombinantly expressing the fusion protein in the host cell.

In some embodiments, the techniques described herein relate to a method, wherein the method includes purifying the fusion protein.

In some embodiments, the techniques described herein relate to a method, wherein the method includes lyophilizing the host cell and/or the purified fusion protein.

In some embodiments, the techniques described herein relate to a method of administering a fusion protein, a host cell, or a pharmaceutical composition of the disclosure to a subject.

In some embodiments, the techniques described herein relate to a method, wherein the subject has a disease or condition associated with weight gain.

In some embodiments, the techniques described herein relate to a method, wherein the disease or condition associated with weight gain is selected from obesity, obesity-linked gallbladder disease, obesity-induced sleep apnea, diabetes, excessive appetite, fatty liver disease, non-alcoholic fatty liver disease (NASH), dyslipidemia, metabolic syndrome, insufficient satiety, hyperinsulinemia, and hypoglycemia.

In some embodiments, the techniques described herein relate to a method, wherein the subject has insulin resistance syndrome or syndrome X.

In some embodiments, the techniques described herein relate to a method, wherein the subject has, or is at risk of developing a condition in which there is a lack of or diminished insulin production.

In some embodiments, the techniques described herein relate to a method, wherein the subject has, or is at risk of developing diabetic obesity.

In some embodiments, the techniques described herein relate to a method, wherein the subject has, or is at risk of developing type 1 diabetes, type 2 diabetes, or gestational diabetes.

In some embodiments, the techniques described herein relate to a method, wherein the subject has, or is at risk of developing one or more of hypertension, dyslipidemia, obstructive sleep apnea, and cardiovascular disease.

In some embodiments, the techniques described herein relate to a method, wherein the pharmaceutical composition, the fusion protein, or the host cell is administered at least once or twice daily.

In some embodiments, the techniques described herein relate to a method, wherein the method includes administration in the form of a tablet or pill.

In some embodiments, the techniques described herein relate to a method of administering a fusion protein, a host cell, or a pharmaceutical composition of the disclosure to a subject in need thereof.

In some embodiments, the techniques described herein relate to a dietary supplement, including: Saccharomyces cerevisiae S288C EV1-Peptide.

In some embodiments, the techniques described herein relate to a dietary supplement, wherein the Saccharomyces cerevisiae S288C EV1-Peptide includes SEQ ID NO: 1.

In some embodiments, the techniques described herein relate to a dietary supplement, wherein the EV1-Peptide includes SEQ ID NO: 6.

In some embodiments, the techniques described herein relate to a dietary supplement, wherein the Saccharomyces cerevisiae S288C EV1-Peptide is encapsulated.

In some embodiments, the techniques described herein relate to a dietary supplement, wherein the Saccharomyces cerevisiae S288C EV1-Peptide is encapsulated in a capsule and present in a dosage form including from about 50 mg to about 1000 mg of Saccharomyces cerevisiae S288C EV1-Peptide.

In some embodiments, the techniques described herein relate to a dietary supplement, wherein the Saccharomyces cerevisiae S288C EV1-Peptide is encapsulated in a capsule and present in a dosage form including from about 100 mg to about 300 mg of Saccharomyces cerevisiae S288C EV1-Peptide.

In some embodiments, the techniques described herein relate to a dietary supplement, wherein the Saccharomyces cerevisiae S288C EV1-Peptide is encapsulated in a capsule and present in a dosage form of about 200 mg of Saccharomyces cerevisiae S288C EV1-Peptide.

In some embodiments, the techniques described herein relate to a dietary supplement, wherein the EV1-Peptide is present from about 100 mcg to about 3000 mcg.

In some embodiments, the techniques described herein relate to a dietary supplement, wherein the EV1-Peptide is present from about 500 mcg to about 2000 mcg.

In some embodiments, the techniques described herein relate to a dietary supplement, wherein the EV1-Peptide is present at about 814 mcg.

In some embodiments, the techniques described herein relate to a dietary supplement, wherein the EV1-Peptide is present at about 1600 mcg.

In some embodiments, the techniques described herein relate to a dietary supplement, wherein the Saccharomyces cerevisiae S288C EV1-Peptide is encapsulated in a vegan capsule.

In some embodiments, the techniques described herein relate to a dietary supplement, wherein the Saccharomyces cerevisiae S288C EV1-Peptide is encapsulated in a vegan capsule engineered for delayed release in the small intestine.

In some embodiments, the techniques described herein relate to a dietary supplement, wherein the Saccharomyces cerevisiae S288C EV1-Peptide is present in a dry powder form.

In some embodiments, the techniques described herein relate to a method 1 to a human in need thereof.

In some embodiments, the techniques described herein relate to a method 1 to a human in need thereof in an amount containing about 100 mg to about 300 mg of Saccharomyces cerevisiae S288C EV1-Peptide.

In some embodiments, the techniques described herein relate to a method 1 to a human in need thereof in an amount containing about 200 mg of Saccharomyces cerevisiae S288C EV1-Peptide.

In some embodiments, the techniques described herein relate to a method 1 to a human in need thereof in an amount containing about 500 mcg to about 2000 mcg of EV1-Peptide.

In some embodiments, the techniques described herein relate to a method 1 to a human in need thereof in an amount containing about 800 to about 1600 mcg of EV1-Peptide.

BRIEF DESCRIPTION OF THE SEVERAL VIEWS OF THE DRAWINGS

The accompanying figures, which are incorporated herein and form a part of the specification, illustrate some, but not the only or exclusive, example embodiments and/or features. It is intended that the embodiments and figures disclosed herein are to be considered illustrative rather than limiting.

FIG. 1B provides additional embodiments of TD, M, and C domain organizations comprised by fusion proteins of the disclosure. FIG. 1C provides additional embodiments of domain organizations comprised by fusion proteins of the disclosure. FIG. 1D provides some embodiments of fusion protein domain organization also comprising solubility-enhancing domains.

FIG. 2A provides a schematic of a fusion protein according to some embodiments of the present disclosure. FIG. 2B provides a schematic of a dual agonist fusion protein according to an embodiment of the present disclosure. FIG. 2C provides a schematic of a dual agonist fusion protein according to an embodiment of the present disclosure.

FIG. 3 provides examples of different expression systems (e.g., host cells such as yeast or *spirulina*) that can be used to express and make the biodelivery platform of the present disclosure.

FIG. 4B provides the annotated full-length sequence of SEQ ID NO: 1. FIG. 4C provides dual incretin agonist sequences (SEQ ID NO: 2-6), and an amino acid sequence of an albumin binding domain (SEQ ID NO: 7).

FIG. 6 provides an encapsulation process of lyophilized yeast cells expressing a fusion protein of the present disclosure.

FIG. 7A shows baseline glucose monitoring data compared to FIG. 7B, which demonstrates decreased average glucose and decreased fluctuation in glucose levels after two weeks of full dose of DA therapeutic.

FIG. 10 shows average body weight measurements for rats in a subacute toxicology study of *Saccharomyces cerevisiae* S288C-I EV1-Peptide. Dosing began on Day 1. Animals in group 1 received vehicle (PBS) and the remaining groups received decreasing dosing (0.3 g-high, 0.15 g-mid, and 0.03 g-low) of study sponsor test article ("TA"). Error bars are+SD.

FIG. 12A shows average body weight (mean±SD) and FIG. 12B shows relative body weight (mean±SEM) of male Sprague Dawley rats throughout a subchronic toxicology study of *Saccharomyces cerevisiae* S288C-I EV1-Peptide. Relative body weight was calculated to the start of dosing on Day 1. No significance was found. (Two-way ANOVA with repeated measures Tukey's multiple comparison test *$p<0.05$).

FIG. 14 shows food consumption of male Sprague Dawley rats throughout the study. Food consumption was measured weekly on a group basis. Statistical significance was not performed.

FIG. 15 shows food consumption of female Sprague Dawley rats throughout the study. Food consumption was measured weekly on a group basis. Statistical significance was not performed.

DETAILED DESCRIPTION

Figure 1A:
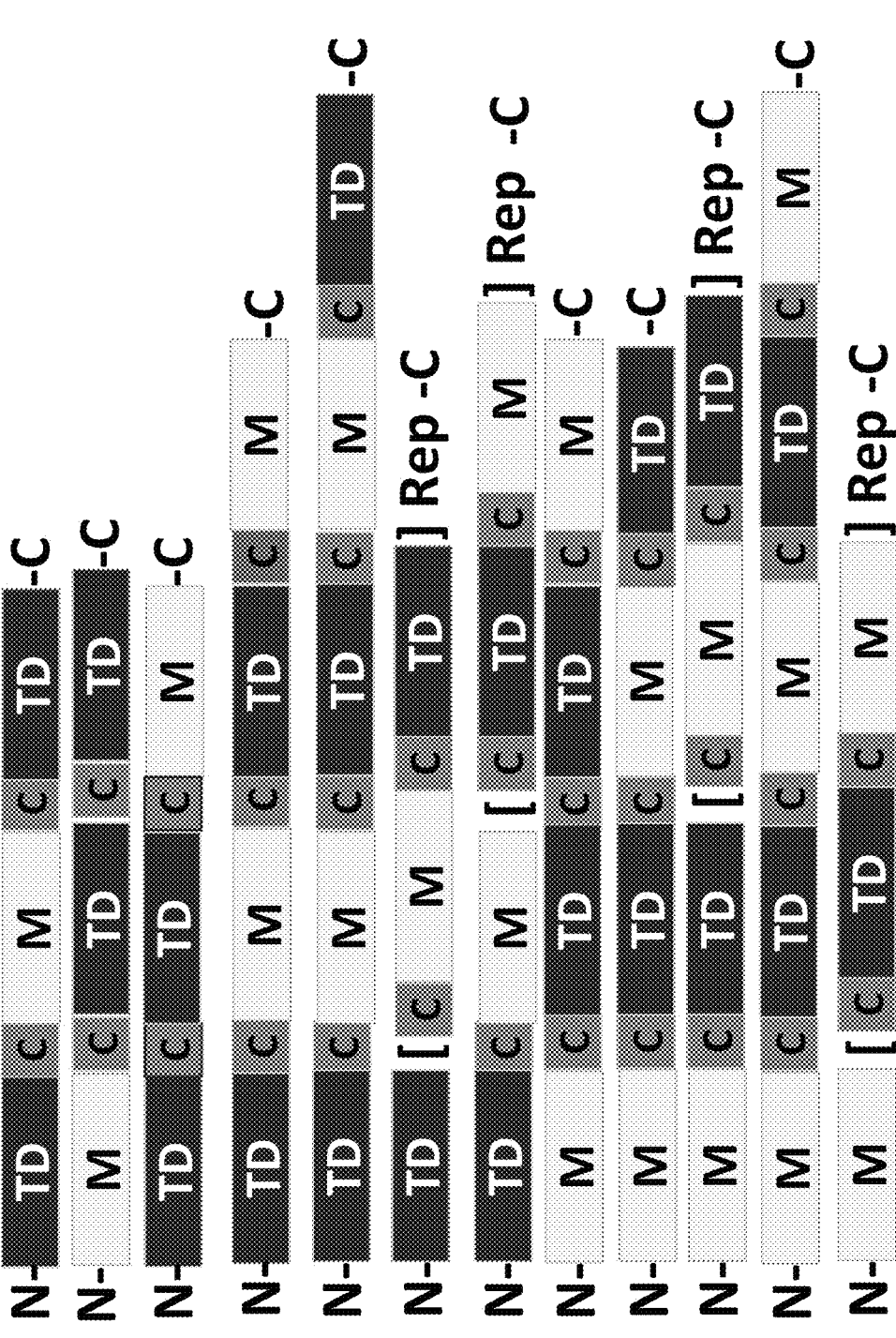
FIG. 1A provides some embodiments of domain organizations comprised by fusion proteins of the disclosure, showing arrangements of transduction domains (TD), molecular cargo domains (M), and cleavage sites (C).

All publications, patents and patent applications, including any drawings and appendices, are herein incorporated by reference to the same extent as if each individual publication or patent application was specifically and individually indicated to be incorporated by reference.

The following description includes information that may be useful in understanding the present disclosure. It is not an admission that any of the information provided herein is prior art or relevant to the presently claimed disclosures, or that any publication specifically or implicitly referenced is prior art.

Definitions

The term "a" or "an" refers to one or more of that entity, i.e. can refer to plural referents. As such, the terms "a," "an," "one or more," and "at least one" are used interchangeably herein. In addition, reference to "an element" by the indefinite article "a" or "an" does not exclude the possibility that more than one of the elements is present, unless the context clearly requires that there is one and only one of the elements.

Throughout this application, the term "about" is used to indicate that a value includes the inherent variation of error for the device or the method being employed to determine the value, or the variation that exists among the samples being measured. Unless otherwise stated or otherwise evident from the context, the term "about" means within 10% above or below the reported numerical value (except where such number would exceed 100% of a possible value or go below 0%). When used in conjunction with a range or series of values, the term "about" applies to the endpoints of the range or each of the values enumerated in the series, unless otherwise indicated. As used in this application, the terms "about" and "approximately" are used as equivalents.

Unless otherwise specified, all numerical ranges disclosed herein include the stated endpoints and encompass all values between those endpoints, as well as any sub-range contained within the stated limits. For example, a range of 10 to 100 includes both 10 and 100, as well as all intermediate values such as 15, 25.5, 50, and 99, as well as sub-ranges such as 20 to 80 and 30 to 60. All numerical values and ranges may be combined with other disclosed ranges or values to form new ranges, unless explicitly stated otherwise.

The term "including all ranges and subranges therebetween" or equivalents, is used herein to denote the intention that disclosure of any range or series of possible values, inherently also discloses all ranges and subranges encompassed by the highest and lowest values disclosed. This term includes the entire range from highest to lowest disclosed values, as well as subranges from any two or more disclosed points. This term is also intended to disclose any subranges encompassed anywhere within the highest and lowest disclosed values, including between two points that are explicitly recited in the document, up to one decimal point. Thus, disclosure of values 0, 5, 10, 15, 20, including all ranges and subranges therebetween, should be interpreted as also encompassing a range from 0-20, a range from 0-5 or 5-15, as well as a range from 2-16, or 3.1 to 19.8, etc. Unless otherwise indicated, it is to be understood that all numbers expressing quantities, ratios, and numerical properties of ingredients, reaction conditions, and so forth, used in the specification are contemplated to be able to be modified in all instances by the term "including all ranges and subranges therebetween".

As used herein the term "sequence identity" refers to the extent to which two optimally aligned polynucleotides or polypeptide sequences are invariant throughout a window of alignment of residues, e.g. nucleotides or amino acids. An "identity fraction" for aligned segments of a test sequence and a reference sequence is the number of identical residues which are shared by the two aligned sequences divided by the total number of residues in the reference sequence segment, i.e. the entire reference sequence or a smaller defined part of the reference sequence. "Percent identity" is the identity fraction times 100. Comparison of sequences to determine percent identity can be accomplished by a number of well-known methods, including for example by using mathematical algorithms, such as, for example, those in the BLAST suite of sequence analysis programs. Unless noted otherwise, the term "sequence identity" in the claims refers to sequence identity as calculated by Clustal Omega® using default parameters.

Overview

The present disclosure provides novel biodelivery platforms for oral administration of molecular cargo, e.g., therapeutic peptides. In some embodiments, the biodelivery platform comprises a fusion protein comprising the molecular cargo. In some embodiments, the biodelivery platform is used to deliver a molecular cargo to a subject in need thereof. Accordingly, the present disclosure also provides methods of treatment using these biodelivery platforms. The present disclosure also provides fusion proteins, nucleic acids, vectors, host cells, pharmaceutical compositions, and methods of treatment related to molecular cargos.

The present disclosure also provides novel incretin agonist mimetics, fusion proteins comprising these mimetics, and methods of treatment using these incretin agonist mimetics and fusion proteins. In aspects, these mimetics are designed to target GLP-1 and/or GIP receptors. In some embodiments, these compositions are delivered via novel oral biodelivery platforms. The present disclosure provides fusion proteins, nucleic acids, vectors, host cells, pharmaceutical compositions, and methods of treatment related to incretin agonist mimetics.

In some embodiments, a fusion protein of the disclosure is formulated for oral delivery. The present inventors developed a fusion protein containing a molecular cargo of interest as a biodelivery platform for delivering the molecular cargo that could overcome many of the disadvantages of previous oral delivery platforms. For example, in some embodiments, when a fusion protein of the disclosure is delivered orally, the fusion protein can make it through the intestinal lumen intact, and once the fusion protein passes through the intestinal epithelial barrier, the delivery components of the fusion peptide are cleaved off, leaving only the molecular cargo to circulate in the bloodstream.

Fusion Proteins

The present disclosure provides fusion proteins. In some embodiments, a fusion protein of the disclosure comprises a molecular cargo domain. In some embodiments, the fusion protein comprises a transduction domain. In some embodiments, the fusion protein comprises an albumin binding domain. In some embodiments, the fusion protein comprises a solubility-enhancing domain. In some embodiments, the fusion protein comprises one or more of: a linker, a hinge, an affinity tag, and a protease cleavage site.

Molecular Cargo Domain

The fusion proteins of the disclosure comprise a molecular cargo domain. This molecular cargo domain comprises a molecular cargo. In some embodiments, the molecular cargo is a therapeutic peptide.

In some embodiments, the therapeutic peptide comprises a full-length protein. In some embodiments, the therapeutic peptide comprises an enzyme, hormone, cytokine, antibody, antibody fragment, and/or antigen. In some embodiments, the therapeutic peptide comprises a peptide-small molecule conjugate. In some embodiments, the therapeutic peptide comprises a ribonucleoprotein (RNP).

In some embodiments, the therapeutic peptide is a cardiovascular peptide. In some embodiments, the therapeutic peptide is selected from the list consisting of: natriuretic peptides, bradykinin analogs, and endothelin antagonists. In some embodiments, the therapeutic peptide is a neurological peptide. In some embodiments, the therapeutic peptide is a pain-modulating peptide. In some embodiments, the therapeutic peptide is selected from the list consisting of: opioid receptor ligands, enkephalin analogs, endorphin mimetics, substance P antagonists, neurotensin analogs, and neuropeptide receptor modulators. In some embodiments, the therapeutic peptides is an oncological peptide. In some embodiments, the therapeutic peptide is selected from the list consisting of: somatostatin analogs (e.g., octreotide, lanreotide, pasireotide), GnRH analogs (e.g., leuprolide, goserelin, buserelin), peptide-drug conjugates, and radiolabeled peptide analogs (e.g., for diagnostic or therapeutic use). In some embodiments, the therapeutic peptide is a hormone or hormone analog. In some embodiments, the therapeutic peptide is selected from the list consisting of: insulin, glucagon, calcitonin, glucagon-like peptide-1 (GLP-1) receptor agonists, parathyroid hormone (PTH) analogs, vasopressin analogs, oxytocin analogs, gonadotropin-releasing hormone (GnRH) analogs, and luteinizing hormone-releasing hormone (LHRH) analogs.

In some embodiments, the therapeutic peptide is a follistatin-derived therapeutic peptide. In some embodiments, the therapeutic peptide is a myostatin-derived therapeutic peptide, e.g., a myostatin antagonist. In some embodiments, the therapeutic peptide is an erythropoietin-derived therapeutic peptide. In some embodiments, the therapeutic peptide is an anti-mullerian hormone therapeutic peptide. In some embodiments, the therapeutic peptide is an insulin-like growth factor-1 (IGF-1) derived therapeutic peptide. In some embodiments, the therapeutic peptide is selected from the list consisting of: Follistatin, IGF-1, EMP-17, GIP, Glucagon, Amylin receptor agonist, Neuropeptide Y receptor type 2 agonist, Melanocortin 4 receptor agonist, Ghrelin receptor antagonist, and Cannabinoid receptor 1 antagonist. In some embodiments, the therapeutic peptide is a myostatin inhibitor.

In some embodiments, the therapeutic peptide is an anti-microbial peptide. In some embodiments, the therapeutic peptide is an anti-infective peptide. In some embodiments, the therapeutic peptide is selected from the list consisting of: defensins, cathelicidins, lactoferrin-derived peptides, magainins, viral fusion inhibitors, and antifungal peptides. In some embodiments, the therapeutic peptide is an immunomodulatory peptide. In some embodiments, the therapeutic peptide is selected from the list consisting of: T-cell epitope peptides, immune checkpoint-modulating peptides, cytokine mimetic peptides, and adjuvant peptides for vaccine formulations. In some embodiments, the therapeutic peptide is a gastrointestinal peptide. In some embodiments, the therapeutic peptide is selected from the list consisting of: motilin agonists, ghrelin analogs, gastrin analogs, and peptide regulators of gastric motility. In some embodiments, the therapeutic peptide is a dermatological peptide. In some embodiments, the therapeutic peptide is a wound-healing peptide. In some embodiments, the therapeutic peptide is selected from the list consisting of: collagen-stimulating peptides, peptides that promote angiogenesis, peptides that modulate metalloproteinase activity, and antimicrobial wound-healing peptides.

In some embodiments, the therapeutic peptide is classified by its structural characteristics. In some embodiments, the therapeutic peptides is a linear peptide. In some embodiments, the therapeutic peptide is a cyclic peptide. In some embodiments, the therapeutic peptide is cyclosporine, lanreotide, or a synthetic macrocyclic analog. In some embodiments, the therapeutic peptide is derived from a natural source. In some embodiments, the therapeutic peptide is a synthetic or modified peptide analog. In some embodiments, the therapeutic peptide is engineered for improved receptor selectivity, stability, or bioavailability. In some embodiments, the therapeutic peptide is a peptide conjugate. In some embodiments, the therapeutic peptide is selected from the list consisting of: drug-peptide conjugates, antibody-peptide conjugates, lipidated peptides, PEGylated peptides, and radiolabeled peptides. In some embodiments, the therapeutic peptide is a peptidomimetic. In some embodiments, the therapeutic peptide comprises a non-natural amino acid, a D-amino acid, and/or a chemically modified backbone. In some embodiments, the therapeutic peptide comprises N-terminal amidation. In some embodiments, the therapeutic peptide comprises features designed to enhance pharmacokinetic and pharmacodynamic properties. In some embodiments, therapeutic peptides include multifunctional or hybrid peptides that combine two or more activities, such as antimicrobial activity and immunomodulatory activity, or receptor agonism and targeted delivery. In some embodiments, therapeutic peptides are designed for diagnostic use, including radiolabeled peptide tracers for imaging or fluorescently tagged peptides for biomarker detection.

In some embodiments, the therapeutic peptide comprises a therapeutic protein. In some embodiments, the therapeutic peptide comprises a naturally occurring, recombinant, engineered, or modified therapeutic protein.

In some embodiments, the therapeutic peptide is an antibody-based therapeutic. In some embodiments, the therapeutic peptide comprises a full-length monoclonal antibody, a humanized or fully human antibody, an antibody fragment (e.g., Fab, scFv, nanobody), or an antibody-drug conjugate (ADC). In some embodiments, the therapeutic peptide comprises an antibody selected from the list consisting of: rituximab, trastuzumab, bevacizumab, cetuximab, nivolumab, pembrolizumab, atezolizumab, durvalumab, ipilimumab, adalimumab, infliximab, golimumab, ustekinumab, secukinumab, ixekizumab, dupilumab, omalizumab, eculizumab, ravulizumab, and denosumab.

In some embodiments, the therapeutic peptide comprises an enzyme replacement therapy. In some embodiments, the therapeutic peptide comprises an enzyme used for lysosomal storage disorders and/or related metabolic deficiencies. In some embodiments, the therapeutic peptide comprises an enzyme selected from the list consisting of: imiglucerase, velaglucerase alfa, taliglucerase alfa (Gaucher disease); alglucosidase alfa, avalglucosidase alfa (Pompe disease); agalsidase alfa, agalsidase beta (Fabry disease); laronidase (MPS I), idursulfase (MPS II), galsulfase (MPS VI), elosulfase alfa (MPS IVA); asfotase alfa (hypophosphatasia); and pegademase bovine (adenosine deaminase deficiency).

In some embodiments, the therapeutic peptide comprises a clotting factor and/or hematologic protein. In some embodiments, the therapeutic peptide comprises a blood coagulation protein, or a variant thereof. In some embodiments, the therapeutic peptide comprises a protein selected from the list consisting of: recombinant Factor VIII (e.g., Advate, Eloctate, Esperoct), recombinant Factor IX (e.g., BeneFIX, Alprolix), von Willebrand factor (Vonvendi), fibrinogen concentrate, recombinant antithrombin (ATryn), and recombinant Factor VIIa (NovoSeven).

In some embodiments, the therapeutic peptide comprises a hormone. In some embodiments, the therapeutic peptide comprises a growth factor. These include peptide and protein hormones and their analogs. In some embodiments, the therapeutic peptide comprises a protein selected from the list consisting of: insulins (lispro, glargine, aspart, degludec), glucagon-like peptide-1 (GLP-1) analogs (liraglutide, semaglutide, dulaglutide, exenatide), pramlintide, somatropin (human growth hormone), mecasermin (IGF-1), erythropoietins (epoetin alfa, darbepoetin alfa, peginesatide), romiplostim, interferon-alpha, interferon-beta, and interferon-gamma.

In some embodiments, the therapeutic peptide comprises a cytokine. In some embodiments, the therapeutic peptide comprises an immune modulator. These include interleukins and colony-stimulating factors. In some embodiments, the therapeutic peptide comprises a protein selected from the list consisting of: aldesleukin (IL-2), anakinra (IL-1 receptor antagonist), tocilizumab (IL-6 receptor antibody), sarilumab, sargramostim (GM-CSF), and etanercept (TNFR-Fc fusion).

In some embodiments, the therapeutic peptide comprises an enzyme for metabolic disease. In some embodiments, the therapeutic peptide comprises an enzyme for oncology. These include therapeutic enzymes beyond classical ERT. In some embodiments, the therapeutic peptide comprises a protein selected from the list consisting of: include pegloticase (urate oxidase, for gout), rasburicase (urate oxidase, for tumor lysis syndrome), asparaginase and pegaspargase (for acute lymphoblastic leukemia), iduronate-2-sulfatase, and heparan N-sulfatase.

In some embodiments, the therapeutic peptide comprises a fusion protein. In some embodiments, the therapeutic peptide comprises an engineered construct. These include receptor-Fc fusions, ligand traps, and immune-modulatory fusions. In some embodiments, the therapeutic peptide is selected from the list consisting of: etanercept (TNFR-Fc), abatacept and belatacept (CTLA4-Ig fusions), and afliber-cept (VEGF-trap).

In some embodiments, the therapeutic peptide comprises other therapeutic peptides and proteins. In some embodi-ments, the therapeutic peptide is selected from the list consisting of: calcitonin, parathyroid hormone analogs (teri-paratide, abaloparatide), glucagon, oxytocin, vasopressin analogs (desmopressin, lypressin), neurotrophic factors (BDNF, NGF, CNTF), and additional hormones or bioactive peptides.

In some embodiments, the expression platform may be applied to any therapeutic protein or peptide currently approved, in clinical development, or rationally designed, thereby encompassing antibody-based drugs, enzyme drugs, coagulation factors, metabolic enzymes, growth factors, hormones, cytokines, fusion proteins, and engineered con-structs.

Incretin Agonist Domain

In some embodiments, the fusion protein comprises a molecular cargo domain comprising an incretin agonist capable of specifically binding to one or more incretin receptors, also referred to herein as an incretin agonist domain. In some embodiments, the incretin agonist domain comprises an incretin agonist mimetic disclosed herein. In some embodiments, the incretin agonist domain is derived from, or comprises, a full-length incretin, a fragment thereof, or an engineered variant thereof with binding affin-ity for an incretin receptor. In some embodiments, the incretin agonist domain comprises a peptide-small molecule conjugate.

In some embodiments, the incretin agonist domain com-prises a dual-incretin agonist. In some embodiments, the incretin agonist domain comprises a triple incretin agonist.

In some embodiments, the incretin agonist is selected from: a glucagon-like peptide 1 (GLP-1) receptor (GLP-1R) agonist (GLP-1RA), a gastric inhibitory polypeptide (GIP) receptor (GIP-R) agonist, a glucagon (G) receptor (GR) agonist (GRA), a dual GLP-1R and GIPR incretin agonist, or a triple GLP-1R, GIPR and GRA incretin agonist. In some embodiments, the incretin agonist is a GLP-1 peptide. In some embodiments, the incretin agonist is a GIP peptide. In some embodiments, the incretin agonist domain is derived from the glucagon-like peptide-1 receptor agonist (GLP-1RA), the glucose-dependent insulinotropic polypeptide receptor agonist (GIPRA), the glucagon receptor agonist (GRA) or derivatives thereof that retain incretin-binding functionality.

In some embodiments, the domain includes modifications to enhance solubility, stability, binding affinity, or specific-ity. In some embodiments, the incretin agonist domain comprises an antibody or antigen-binding antibody frag-ment. In some embodiments, the domain comprises a mono-clonal antibody, a single-chain variable fragment (scFv), a nanobody, or an aptamer.

In some embodiments, the incretin agonist domain binds to GLP-1R. In some embodiments, the incretin agonist domain binds to GIPR. In some embodiments, the incretin agonist domain is a dual incretin agonist that binds both GLP-1 and GIP receptors. In some embodiments, the incre-tin agonist domain binds to a receptor in addition to GLP-1R and GIPR. In some embodiments, the incretin agonist domain comprises GLP-1, a fragment thereof, or a deriva-tive thereof. In some embodiments, the incretin agonist domain comprises a variant of the GLP-1 (7-37) form. In some embodiments, the incretin agonist domain binds to a glucagon receptor (GCGR). In some embodiments, the incretin agonist domain binds to a GLP-2 receptor (GLP-2R).

In some embodiments, the incretin agonist domain is a dual incretin agonist having the sequence of X1-X2-X3-Gly-Thr-Phe-X7-Ser-X9-X10-X11-Ile-X13-X14-X15-X16-X17-Ala-X19-X20-X21-X22-X23-X24-Trp-Leu-X27-X28-X29-X30-X31-X32-X33-X34-X35-X36-X37-X38-X39-X40-X41-X42 (SEQ ID NO: 16), wherein X1 is His or Tyr; X2 is Ala, Gly, or aminoisobutyric acid (Aib); X3 is Glu or Asp; X7 is Thr, Ser, or Ile; X9 is Asp or Glu; X10 is Tyr, Leu, or Ser; X11 is Ser or Leu; X13 is Ala, Tyr, Aib, or alpha-methyl-L-leucine (αMeL); X14 is Met, Leu, or Ser; X15 is Asp or Glu; X16 is Lys, Gly, Ser, or Glu; X17 is Ile, Lys, Gln, Arg, or Glu; X19 is Gln, Ala, Glu, or Lys; X20 is Gln, Lys, or Arg; X21 is Asp, Ala, or Glu; X22 is Phe; X23 is Val, Ile, or Leu; X24 is Gln, Asn, Glu, Arg or Lys; X27 is Leu, Val, Ile, Lys, Glu, or Ser; X28 is Ala, Ser, Arg, or Aib; X29 is Gln, Glu, Lys, Gly, Tyr, or Aib; X30 is Lys, Gly, Pro, or absent; X31 is Gly, Pro, Ser, Glu, or absent; X32 is Lys, Ser, or absent; X33 is Lys, Ser, Glu, or absent; X34 is Asn, Gly, Ala, Lys, or absent; X35 is Asp, Ala, Pro, Glu, or absent; X36 is Trp, Pro, Lys, or absent; X37 is Lys, Pro, Glu, or absent; X38 is His, Pro, Ser, Lys, or absent; X39 is Asn, Ser, or absent; X40 is Ile or absent; X41 is Thr or absent; and X42 is Gln or absent. In some embodiments, the incretin agonist domain comprises an amino acid sequence having at least about 70, 75, 80, 85, 90, 95, 96, 97, 98, or 99% sequence identity to SEQ ID NO: 16. In some embodiments, the incretin agonist domain comprises an amino acid sequence having at least about 90, 95, 96, 97, 98, or 99% sequence identity to SEQ ID NO: 16. In some embodiments, the incretin agonist domain comprises an amino acid sequence having at least about 87, 89, 92, 94, or 97% sequence identity to SEQ ID NO: 16. In some embodiments, the incretin agonist domain comprises an amino acid sequence having at least about 90% sequence identity to SEQ ID NO: 16. In some embodiments, SEQ ID NO: 16 comprises a fatty acid lipidation. In some embodiments, SEQ ID NO: 16 comprises a fatty acid lipidation equivalent to one of those comprised by any of the incretin agonists disclosed herein, e.g., semaglutide, tirzepatide, or retatrutide.

In some embodiments, the incretin agonist domain com-prises the amino acid sequence YGEGTFTSDYSIALDKI-AQKAFVQWLIAGGPSSGAPPPS (SEQ ID NO: 2). In some embodiments, the incretin agonist domain comprises an amino acid sequence having 1, 2, 3, 4, 5, 6, 7, 8, 9, or 10 amino acids different from SEQ ID NO: 2. In some embodi-ments, the incretin agonist domain comprises an amino acid sequence having 1, 2, 3, 4, or 5 amino acids different from SEQ ID NO: 2. In some embodiments, the incretin agonist domain comprises an amino acid sequence having at least about 70, 75, 80, 85, 90, 95, 96, 97, 98, or 99% sequence identity to SEQ ID NO: 2. In some embodiments, the incretin agonist domain comprises an amino acid sequence having at least about 90, 95, 96, 97, 98, or 99% sequence identity to SEQ ID NO: 2. In some embodiments, the incretin agonist domain comprises an amino acid sequence having at least about 87, 89, 92, 94, or 97% sequence identity to SEQ ID NO: 2. In some embodiments, the incretin agonist domain comprises an amino acid sequence having at least about 90% sequence identity to SEQ ID NO:

2. SEQ ID NO: 2 was developed by the inventors and can bind both GLP-1 and GIP receptors while also increasing its half-life in the system. Additionally, the binding affinities to both receptors were found to be higher than those of their corresponding incretins.

In some embodiments, the incretin agonist domain comprises the amino acid sequence YGQGTFTSDYSIYLDKQAQQAFIEYL-LEGGPSSGAPPPS (SEQ ID NO: 17). In some embodiments, the incretin agonist domain comprises an amino acid sequence having 1, 2, 3, 4, 5, 6, 7, 8, 9, or 10 amino acids different from SEQ ID NO: 17. In some embodiments, the incretin agonist domain comprises an amino acid sequence having 1, 2, 3, 4, or 5 amino acids different from SEQ ID NO: 17. In some embodiments, the incretin agonist domain comprises an amino acid sequence having at least about 70, 75, 80, 85, 90, 95, 96, 97, 98, or 99% sequence identity to SEQ ID NO: 17. In some embodiments, the incretin agonist domain comprises an amino acid sequence having at least about 90, 95, 96, 97, 98, or 99% sequence identity to SEQ ID NO: 17. In some embodiments, the incretin agonist domain comprises an amino acid sequence having at least about 90% sequence identity to SEQ ID NO: 17.

In some embodiments, the incretin agonist domain has an amino acid sequence disclosed in Table 1. In some embodiments, the incretin agonist domain has an amino acid sequence having 1, 2, 3, 4, 5, 6, 7, 8, 9, or 10 amino acids different from an amino acid sequence disclosed in Table 1. In some embodiments, the incretin agonist domain has an amino acid sequence having 1, 2, 3, 4, or 5 amino acids different from an amino acid sequence disclosed in Table 1. In some embodiments, the incretin agonist domain has an amino acid sequence having at least about 70, 75, 80, 85, 90, 95, 96, 97, 98, or 99% sequence identity to an amino acid sequence disclosed in Table 1. n some embodiments, the incretin agonist domain has an amino acid sequence having at least about 80, 85, 90, 95, 96, 97, 98, or 99% sequence identity to an amino acid sequence disclosed in Table 1.

TABLE 1

| Incretin Agonists. | | |
| --- | --- | --- |
| Generic Name; Trade Names & Drug Bank Entry | Base Protein & Modifications | Amino Acid Sequence |
| Exenatide; Byetta ®, Bydureon ® go.drugbank.com/drugs/DB01276 | Exendin-4 None | HGEGTFTSDLSKQMEEEAVRLFIEWLKNG GPSSGAPPPS (SEQ ID NO: 37) |
| Liraglutide; Victoza ®, Saxenda ® go.drugbank.com/drugs/DB06655 | GLP-1(7-37) K34R, Lys26-[N-ε-(γ-Glu{N-α-hexadecanoyl})] | HAEGTFTSDVSSYLEGQAAKEEFIAWLVR GRG (SEQ ID NO: 38) |
| Dulaglutide; Trulicity ® go.drugbank.com/drugs/DB09045 | GLP-1 analog Fc-fusion (IgG4), DPP-4 resistant substitutions: A8G, G22E, R36G | HGEGTFTSDVSSYLEEQAAKEFIAWLVKG GGGGGGSGGGGSGGGGSAESKYGPPCPPC PAPEAAGGPSVFLFPPKPKDTLMISRTPEVT CVVVDVSQEDPEVQFNWYVDGVEVHNAK TKPREEQFNSTYRVVSVLTVLHQDWLNGK EYKCKVSNKGLPSSIEKTISKAKGQPREPQ VYTLPPSQEEMTKNQVSLTCLVKGFYPSDI AVEWESNGQPENNYKTTPPVLDSDGSFFL YSRLTVDKSRWQEGNVFSCSVMHEALHN HYTQKSLSLSLG (SEQ ID NO: 39) |
| Semaglutide; Ozempic ®, Wegovy ®, Rybelsus ® go.drugbank.com/drugs/DB13928 | GLP-1(7-37) A8Aib; K34R; acylation of Lys26 with a spacer consisting of two 8-amino-3,6-dioxaoctanoic acid (ADO) moieties, a glutamic acid moiety, and a C-18 fatty di-acid side chain | HAibEGTFTSDVSSYLEGQAAKEFIAWLVR GRG (SEQ ID NO: 40) |
| Lixisenatide; Adlyxin ®, Lyxumia ® go.drugbank.com/drugs/DB09265 | Exendin-4 analog C-terminal extension, DPP-4 resistance | HGEGTFTSDLSKQMEEEAVRLFIEWLKNG GPSSGAPPSKKKKKK (SEQ ID NO: 41) |
| Albiglutide; Tanzeum ® (withdrawn) go.drugbank.com/drugs/DB09043 | GLP-1(7-36) dimer A8G; Fused to human albumin | HGEGTFTSDVSSYLEGQAAKEFIAWLVKG RHGEGTFTSDVSSYLEGQAAKEFIAWLVK GRDAHKSEVAHRFKDLGEENFKALVLIAF AQYLQQCPFEDHVKLVNEVTEFAKTCVAD ESAENCDKSLHTLFGDKLCTVATLRETYG EMADCCAKQEPERNECFLQHKDDNPNLPR LVRPEVDVMCTAFHDNEETFLKKYLYEIA RRHPYFYAPELLFFAKRYKAAFTECCQAA DKAACLLPKLDELRDEGKASSAKQRLKCA SLQKFGERAFKAWAVARLSQRFPKAEFAE VSKLVTDLTKVHTECCHGDLLECADDRAD LAKYICENQDSISSKLKECCEKPLLEKSHCI AEVENDEMPADLPSLAADFVESKDVCKNY AEAKDVFLGMFLYEYARRHPDYSVVLLLR LAKTYETTLEKCCAAADPHECYAKVFDEF KPLVEEPQNLIKQNCELFEQLGEYKFQNAL |

TABLE 1-continued

Incretin Agonists.

| Generic Name; Trade Names & Drug Bank Entry | Base Protein & Modifications | Amino Acid Sequence |
|---|---|---|
| | | LVRYTKKVPQVSTPTLVEVSRNLGKVGSK CCKHPEAKRMPCAEDYLSVVLNQLCVLHE KTPVSDRVTKCCTESLVNRRPCFSALEVDE TYVPKEFNAETFTFHADICTLSEKERQIKK QTALVELVKHKPKATKEQLKAVMDDFAA FVEKCCKADDKETCFAEEGKKLVAASQAA LGL (SEQ ID NO: 42) |
| Beinaglutide; Benemae ® go.drugbank.com/drugs/DB15072 | GLP-1(7-36) None, recombinant human sequence | HAEGTFTSDVSSYLEGQAAKEFIAWLVKG R (SEQ ID NO: 43) |
| Tirzepatide; Mounjaro ®, Zepbound ® go.drugbank.com/drugs/DB15171 | GIP-based hybrid A2Aib; A13Aib; eicosanedioic acid linked via a glutamic acid and two (2-(2-aminoethoxy)ethoxy) acetic acid units to Lys20 | YXEGTFTSDYSIXLDKIAQKAFVQWLIAGG PSSGAPPPS (SEQ ID NO: 44) |
| PEG-loxenatide go.drugbank.com/drugs/DB19230 | GLP-1 analog PEGylation for half-life extension | PEGn-H-{d-Ala}-EGTFTSDLSKQ-{Nle}-EEEAVRLFIEWLKQGGPSSGAPPPC (SEQ ID NO: 45) |
| Retatrutide go.drugbank.com/drugs/DB18993 guidetopharmacology.org/GRAC/ LigandDisplayForward?tab=structure&ligandId=13769 | GCGR, GIPR, GLP-1R agonist H1Y; A2Aib; L13MeL; lipidation of K17 with eicosanedioic acid via γ-glutamic acid and two units of (2-(2-aminoethoxy)ethoxy) acetic acid | Tyr-{Aib}-Gln-Gly-Thr-Phe-Thr-Ser-Asp-Tyr-Ser-Ile-{α-Me-Leu}-Leu-Asp-Lys-{diacid-C20-gamma-Glu-(AEEA)-Lys}-Ala-Gln-{Aib}-Ala-Phe-Ile-Glu-Tyr-Leu-Leu-Glu-Gly-Gly-Pro-Ser-Ser-Gly-Ala-Pro-Pro-Pro-Ser-NH2 (SEQ ID NO: 52) |

GLP-1 Receptor Agonists

In some embodiments, the molecular cargo domain comprises a GLP-1 receptor agonist. Glucagon-like peptide-1 (GLP-1) receptor agonists are glucose-lowering drugs that induce clinically significant reductions in body weight. Glucagon-like peptide 1 receptor (GLP-1R) belongs to Family B1 of the seven-transmembrane G protein-coupled receptors, and its natural agonist ligand is the peptide hormone glucagon-like peptide-1 (GLP-1). GLP-1 is a peptide hormone arising by its alternative enzymatic cleavage from proglucagon, the prohormone precursor for GLP-1, which is highly expressed in enteroendocrine cells of the intestine, the alpha cells of the endocrine pancreas (islets of Langerhans), and the colon. GLP-1 acts through a G protein-coupled cell surface receptor (GLP-1R) and enhances nutrient-induced insulin synthesis and release. GLP-1 stimulates insulin secretion (insulinotropic action) and cAMP formation. GLP-1 (7-36) amide stimulates insulin release, lowers glucagon secretion, and inhibits gastric secretion and emptying. These gastrointestinal effects of GLP-1 are not found in vagotomized subjects, pointing to a centrally-mediated effect. GLP-1 stimulates glycogen synthesis, glucose oxidation, and lactate formation in rat skeletal muscle. In some embodiments, the GLP-1 receptor agonist comprises a peptide-small molecule conjugate comprising any one of the small molecules disclosed herein.

On activation, GLP-1 receptors couple to the α-subunit of G protein, with subsequent activation of adenylate cyclase and increase of cAMP levels, thereby potentiating glucose-stimulated insulin secretion. Therefore, GLP-1 is also an attractive therapeutic target to lower blood glucose and preserve the B-cells of the pancreas of diabetic patients or patients diagnosed with obesity. The capability of activating the human GLP-1 receptor may be determined in a medium containing membrane expressing the GLP-1 receptor, and/or in an assay with whole cells expressing the GLP-1 receptor. Alternatively, the response of the human GLP-1 receptor may be measured in a reporter gene assay.

In some embodiments, the molecular cargo domain comprises a GLP-1 receptor agonist (GLP-1RA) that is a polypeptide or polypeptide analog. A GLP-1RA can be an incretin mimetic, or GLP-1 analog. In some embodiments, the GLP-1RA is a fusion protein, or fusion of a protein and peptide. In some embodiments, the GLP-1RA is a recombinant polypeptide. In some embodiments, the GLP-1RA is a synthetic polypeptide. In some embodiments, the GLP-1RA is a fusion protein that agonizes GLP1R for Type 2 diabetes.

In some embodiments, the molecular cargo domain comprises a GLP-1RA that has additional agonist activity at one or more receptors or relevant biological targets. In some embodiments, the GLP-1RA is a dual agonist. In some embodiments, the dual agonist is an agonist of GLP-1R and gastric inhibitory polypeptide (GIP) receptor.

In some embodiments, the dual agonist is an agonist of GLP-1R and gastric inhibitory polypeptide (GIP) receptor. In some embodiments, the GLP-1RA is an agonist of GLP-1R, GIP receptor and/or glucagon receptor. In some embodiments, the GLP-1RA is an agonist of GLP-1R and glucagon receptor. In some embodiments, the GLP-1RA is an agonist of GLP-1R and GIP receptor. In some embodiments, the GLP-1RA is a peptide drug for diabetes and/or obesity that agonizes GLP-1R and GCGR.

In some embodiments, the molecular cargo domain comprises a GLP-1RA that is a triple agonist, e.g., an agonist of GLP-1R, GIP receptor and glucagon receptor. Retatrutide (LY3437943) is an exemplary triple G agonist. Other triple G agonists of interest include those described by Knerr et al. (Next generation GLP-1/GIP/glucagon triple agonists normalize body weight in obese mice, Mol. Metab. 2022 September; 63:101533), incorporated by reference herein.

In some embodiments, the molecular cargo domain comprises a GLP-1RA that is selected from the list consisting of: exenatide, semaglutide, liraglutide, insulin degludec+liraglutide, insulin glargine+lixisenatide, cagrilintide [INN]+ semaglutide, albenatide [INN], cotadutide, CT-868, PF 06882961, efocipegtrutide, LY-3502970 (Orforglipron), NLY-001, pegapamodutide, pemvidutide, PF-07081532, retatrutide, RGT-075, TTP-273, vurolenatide, GZR-18, mazdutide, PB-119, AMG-133, dapiglutide, DD-01, DR-10627, ECC-5004, exenatide biobetter, GL-0034, GMA-105, HEC-88473, LY-3493269, NN-6177, NN-9847, NNC0519-0130, PB-1023, Peptides to Agonize GLP-1 and GCGR for Diabetes and Obesity, Peptides to Agonize GLP-1 and GCGR for Diabetes and Obesity, SCO-094, semaglutide, VK-2735, YH-25724, YN-012 (Supaglutide), NLY-02, ZP7570 (dapiglutide), and YN-015.

In some embodiments, the molecular cargo domain comprises a GLP-1 receptor agonist selected from the list consisting of: albenatide, albiglutide, avexitide, cafraglutide, cotadutide, danuglipron, dapiglutide, diabegone, dulaglutide, ecnoglutide, efpeglenatide, efinopegdutide, efocipegtrutide, exenatide, exenatide biobetter, exenatide SR, froniglutide, liraglutide, liraglutide biobetter, lixisenatide, CT-868, efocipegtrutide, LY-3502970 (Orforglipron), maridebart, mazdutide, NLY-001, orforglipron, pegapamodutide, pemvidutide, retatrutide (LY-3437943), semaglutide, semaglutide injection, survodutide, vurolenatide, dapagliflozin+semaglutide, (cagrilintide+semaglutide), (LAI-287+semaglutide), (semaglutide+GIP analogue), 4P-004, AMG-133, AP-026, AZD-9550, BGM-0504, BMS-686117, Zn/BMS-686117 adduct, CT-388, CT-868, CT-996, DD-01, DR-10624, DR-10627, ECC-5004, E-2HSA, GL-0034, GLP-06, GMA-105, GMA-106, GMA-102, GSBR-1290, GXG-6, GZR-18, HEC-88473, HR-17031, HRS-7535, HRS-9531, HS-20004, HS-20094, HB-1085, HDM-1002, HL-08, HZ-010, JY-09, KN-056, LY-3493269, MBX-1416, MDR-001, MWN-101, NLY-001, NN-9490, NNC0519-0130, NN-6177, NN-9847, NN-9904, NN-6535 (semaglutide), NN-9932 (semaglutide), PF-06954522, PF-07081532, PF-06882961 (Danuglipron), PB-1023, PB-119, PB-718, RGT-075, SAL-015, SAL-0112, SCO-094, TERN-601, TTP-273, Uni-E4, VK-2735, YH-25724, ecnoglutide (XW-004), XW-003, XW-014, YH-25724, YN-012 (Supaglutide), YN-015, ZP7570 (dapiglutide), ZT-002, and pharmaceutically acceptable salts thereof.

In some embodiments, the GLP-1 receptor agonist is danuglipron.

In some embodiments, the molecular cargo domain comprises dulaglutide. Dulaglutide reduces fasting glucose concentrations and reduces postprandial glucose (PPG) concentrations in patients with type 2 diabetes mellitus through the agonism of the GLP-1 receptor. This drug primarily acts as an incretin mimetic hormone or analog of human glucagon-like peptide-1, which normally acts on the GLP-1 receptor. Dulaglutide activates the GLP-1 receptor found in pancreatic beta cells, increasing intracellular cyclic AMP (CAMP) in beta cells, leading to insulin release and subsequent reduction of blood glucose concentrations. Additionally, dulaglutide decreases glucagon secretion and slows gastric emptying.

In some embodiments, the molecular cargo domain comprises exenatide. Exenatide binds to the intact human Glucagon-like peptide-1 receptor (GLP-1R) in a similar way to the human peptide glucagon-like peptide-1 (GLP-1).

In some embodiments, the molecular cargo domain comprises semaglutide. Semaglutide is a polypeptide that contains a linear sequence of 31 amino acids joined together by peptide linkages. It has a role as a hypoglycemic agent, a glucagon-like peptide-1 receptor agonist, an anti-obesity agent, a neuroprotective agent and an appetite depressant. It is a polypeptide and a lipopeptide.

In some embodiments, the molecular cargo domain comprises liraglutide. Liraglutide is a lipopeptide that is an analogue of human GLP-1 in which the lysine residue at position 27 is replaced by arginine and a hexadecanoyl group attached to the remaining lysine via a glutamic acid spacer. Liraglutide is typically used as an adjunct to diet and exercise to improve glycemic control in adults with type 2 diabetes mellitus. It has a role as a glucagon-like peptide-1 receptor agonist and a neuroprotective agent. It is a lipopeptide and a polypeptide. In some embodiments, liraglutide and insulin degludec are co-administered. Insulin degludec is typically used with a proper diet and exercise program to control high blood sugar in people with diabetes. The combination therapy of insulin degludec and liraglutide gives a robust glycemic control with a low risk for hypoglycemia and less weight gain or even weight loss.

In some embodiments, the molecular cargo domain comprises lixisenatide. In some embodiments, a method of the disclosure comprises administering a fusion protein comprising GLP-1RA in combination with insulin glargine. In some embodiments, the method further comprises administering GLP-1RA in combination with glucose-dependent insulinotropic polypeptide (GIP). In some embodiments, the insulin glargine in combination with lixisenatide is Soliqua 100/33. Insulin glargine and lixisenatide is a combination medicine that is typically used together with diet and exercise to improve blood sugar control in adults with type 2 diabetes. Insulin glargine is a long-acting insulin that starts to work several hours after injection and keeps working evenly for 24 hours. Lixisenatide is a drug that helps the pancreas produce insulin more efficiently.

In some embodiments, the molecular cargo domain comprises cotadutide. Cotadutide (MEDI0382), a dual GLP-1 and glucagon receptor agonist, is currently under development for type 2 diabetes and NASH.

In some embodiments, the molecular cargo domain comprises CT-868. CT-868 is a dual GLP-1 and GIP receptor modulator that is optimized for improved tolerability at the GLP-1 receptor. The combined action of GLP-1 and GIP result in greater body weight loss and glucose control.

In some embodiments, the molecular cargo domain comprises efocipegtrutide. Efocipegtrutide is a glucagon, gastric inhibitory polypeptide (GIP) and glucagon-like peptide 1 (GLP-1) receptors agonist. Efocipegtrutide shares sequence homology with glucagon, glucagon-like peptide 1 (GLP1) and gastric inhibitory polypeptide (GIP, glucose-dependent insulinotropic polypeptide, incretin hormone), where the gastric inhibitory peptide (GIP) and glucagon-like peptide-1 (GLP-1) triple full agonist is chemically conjugated with constant region of human immunoglobulin via non-peptidyl flexible linker.

In some embodiments, the molecular cargo domain comprises NLY-001. NLY-001 is a microglia-targeted GLP-1RA.

NLY-001 is a pegylated exendin-4 analogue of Glucagon Like Peptide-1 Receptor (GLP-1R) agonist.

In some embodiments, the molecular cargo domain comprises pegapamodutide.

In some embodiments, the molecular cargo domain comprises pemvidutide. Pemvidutide is a peptide-based GLP-1/glucagon dual receptor agonist developed for the treatment of obesity and non-alcoholic steatohepatitis (NASH). Pemvidutide has been shown to substantially decrease the amount of fat within the liver which could have beneficial effects on insulin resistance and cardiorenal risk, common problems in people with obesity. In clinical trials, pemvidutide demonstrated striking reductions in body weight, liver fat, serum lipids and markers of liver inflammation.

In some embodiments, the molecular cargo domain comprises retatrutide. Retatrutide stimulates GIPR, GLP-1, and GLP-1 receptors.

In some embodiments, the molecular cargo domain comprises TTP-273.

In some embodiments, the molecular cargo domain comprises vurolenatide. Vurolenatide is a GLP-1 receptor agonist.

In some embodiments, the molecular cargo domain comprises GZR-18. GZR-18 is an analog of glucagon-like peptide-1 (GLP-1). In vitro pharmacology and activity of GZR18 were previously characterized by a binding assay of GZR18 using human serum albumin (HSA), an activation assay in human GLP-1 receptor-expressing cell lines, and its effect on glucose-stimulated insulin secretion (GSIS) in primary mice islets.

In some embodiments, the molecular cargo domain comprises mazdutide. Mazdutide (IBI362) is a glucagon-like peptide-1 (GLP-1) and glucagon receptor dual agonist. Mazdutide is a long-acting synthetic peptide related to mammalian oxyntomodulin (OXM), which uses a fatty acid side chain to prolong the duration of action and allow once-weekly administration. Mazdutide is thought to exert its biological effects by activating GLP-1 receptor and glucagon receptor in human beings, which is estimated to improve glucose tolerance and induce weight loss, mimicking the effects of endogenous oxyntomodulin.

In some embodiments, the molecular cargo domain comprises PB-119. PB-119 is a pegylated human glucagon-like peptide-1 (GLP-1) receptor agonist.

In some embodiments, the molecular cargo domain comprises AMG-133. AMG 133 is a bispecific glucose-dependent insulinotropic polypeptide receptor (GIPR) antagonist and glucagon-like peptide-1 (GLP-1) receptor agonist molecule. AMG 133 mimics the agonist effects of GLP-1 and antagonizes the effects of glucose-dependent insulinotropic polypeptide (GIP).

In some embodiments, the molecular cargo domain comprises dapiglutide. Dapiglutide promotes significant intestinal growth, as indicated by significantly increased villus height as well as intestinal length. Dapiglutide reduces stool water losses, resulting in reduced plasma aldosterone. It has been shown that dapiglutide possesses specific and potent GLP-1R and GLP-2R agonist effects in rodents.

In some embodiments, the molecular cargo domain comprises semaglutide. Semaglutide is a GLP-1 agonist and works by increasing insulin release, lowering the amount of glucagon released, delaying gastric emptying and reducing appetite.

In some embodiments, the molecular cargo domain comprises DD-01. DD-01 is a pegylated, long-acting, peptide based dual agonist of glucagon-like peptide 1 (GLP-1) receptor and glucagon receptor (GCGR). In some embodiments, the GLP-1RA is DR-10627. In some embodiments, the GLP-1RA is ECC-5004. ECC-5004 is an orally administered small-molecule GLP-1 RA. In some embodiments, the GLP-1RA is exenatide biobetter. In some embodiments, the GLP-1RA is GL-0034. GL0034 is a glucagon-like peptide-1 receptor (GLP-1R) agonist that has been shown to have glucose-lowering effects with increased insulin and C-peptide levels, reduced plasma glucagon levels, long-term reduction in HbAlC, and reduced body weight when tested in type 2 diabetic mice. In some embodiments, the GLP-1RA is GMA-105. GMA-105 is a humanized anti-GLP-1R monoclonal antibody carrying a GLP-1 fragment. In some embodiments, the GLP-1RA is HEC-88473. HEC88473 is a GLP-1/FGF21 dual agonist. In some embodiments, the GLP-1RA is LY-3493269. LY-3493269 is a GIP/GLP coagonist peptide. In some embodiments, the GLP-1RA is NN-6177. NN-6177 acts by targeting glucagon receptor (GCGR) and glucagon like peptide 1 receptor (GLP1R). In some embodiments, the GLP-1RA is NN-9847. In some embodiments, the GLP-1RA is NNC0519-0130. In some embodiments, the GLP-1RA is PB-1023. PB-1023 is a recombinant GLP-1 analogue used to treat sarcopenia-related diseases. In some embodiments, the GLP-1RA is SCO-094. SCO-094 is a dual agonist for GLP-1R and GIPR. Preclinical studies have shown that SCO-094 is more effective in improving diabetes and obesity than the GLP-1R mono-agonist. In some embodiments, the GLP-1RA is VK-2735. VK-2735 is a dual agonist of the glucagon-like peptide 1 (GLP-1) and glucose-dependent insulinotropic polypeptide (GIP) receptors for the potential treatment of various metabolic disorders such as diabetes, obesity and NASH. In some embodiments, the GLP-1RA is YH-25724. YH-25724 is a long-acting GLP-1/FGF21 dual agonist that lowers both non-alcoholic fatty liver disease activity score and fibrosis stage in a diet-induced obese mouse model of biopsy-confirmed non-alcoholic steatohepatitis. In some embodiments, the GLP-1RA is YN-012 (Supaglutide). In some embodiments, the GLP-1RA is YN-015. In some embodiments, the GLP-1RA is ZP7570 (dapiglutide).

In some embodiments, the GLP-1 receptor agonist (GLP-1RA) is a small molecule agonist of the GLP-1 receptor. In some embodiments, the GLP-1RA is PF-07081532. PF-07081532 is an oral small molecule GLP-1 receptor agonist that is being developed for the treatment of Type 2 diabetes and obesity.

GLP-1RA agents can include, but are not limited to, dapagliflozin+semaglutide, 4P-004, AP-026, BGM-0504, CT-996, DD-01, DR-10624, DR-10627, dulaglutide, ECC-5004, exenatide, exenatide biobetter, GL-0034, GLP-06, GMA-106, HB-1085, HDM-1002, HL-08, HZ-010, KN-056, liraglutide, MWN-101, NN-6177, NN-9847, NN-9904, PF-06954522, SAL-0112, SCO-094, TERN-601, ecnoglutide (XW-004), XW003, XW-014, YH-25724, YN-012 (Supaglutide), YN-015, ZP7570 (dapiglutide), and ZT-002.

GLP-1RA agents of interest which can be utilized in the methods of this disclosure include, but are not limited to, dapagliflozin+semaglutide, 4P-004, AP-026, BGM-0504, CT-996, DD-01, DR-10624, DR-10627, dulaglutide, ECC-5004, exenatide, exenatide biobetter, GL-0034, GLP-06, GMA-106, HB-1085, HDM-1002, HL-08, HZ-010, KN-056, liraglutide, MWN-101, NN-6177, NN-9847, NN-9904, PF-06954522, SAL-0112, SCO-094, TERN-601, XW-004, XW-014, YH-25724, YN-012 (Supaglutide), YN-015, and ZT-002.

Other GLP-1RA agents of interest, e.g., in clinical trials include, but are not limited to, (semaglutide+GIP analogue), AZD-9550, CT-388, CT-868, danuglipron tromethamine, dapiglutide, E-2HSA, efinopegdutide (HM12525A), efocipegtrutide, exenatide SR, froniglutide, GMA-105, GSBR-1290, GXG-6, GZR-18, HEC-88473, HR-17031, HRS-7535, HRS-9531, HS-20004, HS-20094, JY-09, liraglutide biobetter, maridebart cafraglutide, MBX-1416, MDR-001, NLY-001, NN-9490, NNC0519-0130, PB-718, pegapamodutide (OPK 88003/TT401), pemvidutide (ALT-801), semaglutide injection, TTP-273, and VK-2735.

Additional GLP-1RA agents of interest in clinical trials which can be utilized in the methods of this disclosure include, but are not limited to, (cagrilintide+semaglutide), retatrutide, (LAI-287+semaglutide), albenatide, avexitide acetate, Diabegone, ecnoglutide, efpeglenatide LA, GMA-102, liraglutide, mazdutide, NN-6535 (semaglutide), NN-9932 (semaglutide), orforglipron calcium, PB-119, SAL-015, survodutide, Uni-E4, and vurolenatide.

Further GLP-1RA agents of interest which can be utilized in the methods of this disclosure include, but are not limited to, (dorzagliatin+GLP-1), (exenatide+insulin aspart), ACT-1003, Adogel Sema, AER-601, AGM-212, BEBT-808, BZ-043B, C-2816, DAJC-1, DD-02, DR-10625, DR-10628, DS-004, DS-005, DS-006, DS-012, E-6, efpeglenatide+HM-12470, exenatide 2, exenatide LA, exenatide SR, Extendin-Fc, G-49, GB-7001, Gene Encoding GLP-1, GLP-1 Incretin Triagonist, GLP-1 Oral Preparation, GLP-1R Antagonist for Hypoglycemia, glucagon, Glucagon-Like Peptide-1+insulin human, GPCR-targeted Project 012, GPCR-targeted Project 013, GT-01123, HM-15275, HPG-5119, HSP-001, HSP-004, HSP-005, HSP012-C, Hydrogel Exenatide, 120-105S, 120-110, KP-405, LA-EX, liraglutide biobetter, liraglutide LA, MK-1462, MLX-7000, MWN-105, MWN-109, NLY-12, NPM-115, OGB-21502, OXM, P-11, PB-2301, PB-2309, RGT-028, RGT-274, RPC-8844, RT-104, SHX-022, SL-209, synthetic peptides to agonize GLP-1R and CCKBR for diabetes, TB-013, TB-222023, TB-592, TE-8105, THDBH-111, UDS-003, VTCG-15, XL-110, XL-310, XW-003+XW-015, XW-003+XW-017, Y-002, YGX-1, ZT-003, ZT-006, ZT-007, DA-1726, HDM-1005, (insulin degludec+liraglutide), DB-081, GW-002, HZCX-012, ID-110521156, THDB-0211, THDBH-110, THDBH-120, THDBH-121, UBT-251, ATBB-22, BEM-012, CIN-209, CIN-210, DD-03, exenatide+ND-017, exenatide+Synthetic Peptide 2, glucagon, Insulin-GLP1, MD-02, OGB-21501, P-01, PAT-201, PF-1807, and PT-3.

Other GLP-1RA agents of interest include, but are not limited to: HMS-5678 BI-3034701, DD-02S, DD-15, efpegerglucagon, 120-130, 120-105S, MBX-4291, NA-931, RJVA-001, TERN-800, HZ-012, HS-10501, ZX-2010, ZX-2021, HYBR-014, PG-102, and VCT-220. S Albumin Binding Domain In some embodiments, a fusion protein of the disclosure comprises an albumin binding domain. In some embodiments, the present disclosure provides fusion proteins comprising an incretin agonist domain and an albumin binding domain. In some embodiments, a fusion protein of the disclosure comprises a molecular cargo domain and an albumin binding domain. In some embodiments, a fusion protein of the disclosure comprises a) a molecular cargo domain comprising a therapeutic peptide of the disclosure, and b) an albumin binding domain.

In some embodiments, the albumin binding domain comprises a peptide, antibody, or antibody fragment that binds to albumin. In some embodiments, the albumin binding domain binds human serum albumin. In some embodiments, the albumin binding moiety binds to two or more species of albumin. In some embodiments, the albumin binding moiety is Domain 3 of streptococcal Protein G or a sequence derived from Domain 3 of Streptococcal Protein G. In some embodiments, the albumin binding moiety is a domain antibody (dAb).

In some embodiments there is only one albumin binding moiety in the fusion protein linked to the molecular cargo with or without a linker. In some embodiments, multiple albumin binding moieties of the same identity or unique individual subunits are ligated together in tandem with or without a linker.

In some embodiments, the affinity of the albumin binding moiety for albumin is characterized by an equilibrium dissociation constant (Kd) that is about 500 nM. In some embodiments, the Kd is about 500 nM or less. In some embodiments, the Kd is about 500 nM or more. In some embodiments, the Kd is about 200 nM or less. In some embodiments, the Kd is about 50 nM or less. In some embodiments, the Kd is about 10 nM or less. In some embodiments, the Kd is about 1 nM or less.

In some embodiments, the albumin binding domain comprises the amino acid sequence of WWEQDRDWDFDVFGGGTP (SEQ ID NO: 7). In some embodiments, the albumin binding domain comprises an amino acid sequence having 1, 2, 3, 4, 5, 6, 7, 8, 9, or 10 amino acids different from SEQ ID NO: 7. In some embodiments, the albumin binding domain comprises an amino acid sequence having 1, 2, 3, 4, or 5 amino acids different from SEQ ID NO: 7. In some embodiments, the albumin binding domain comprises an amino acid sequence having at least about 70, 75, 80, 85, 90, 95, 96, 97, 98, or 99% sequence identity to SEQ ID NO: 7. In some embodiments, the albumin binding domain comprises an amino acid sequence having at least about 90, 95, 96, 97, 98, or 99% sequence identity to SEQ ID NO: 7. In some embodiments, the albumin binding domain comprises an amino acid sequence having at least about 90% sequence identity to SEQ ID NO: 7.

In some embodiments, the albumin binding domain has an amino acid sequence disclosed in Table 2. In some embodiments, the albumin binding domain has an amino acid sequence having 1, 2, 3, 4, 5, 6, 7, 8, 9, or 10 amino acids different from an amino acid sequence disclosed in Table 2. In some embodiments, the albumin binding domain has an amino acid sequence having 1, 2, 3, 4, or 5 amino acids different from an amino acid sequence disclosed in Table 2.

TABLE 2

Albumin-binding domain sequences.

| SEQ ID NO | Amino Acid Sequence |
|---|---|
| 7 | WWEQDRDWDFDVFGGGTP |
| 18 | DXCLPXWGCLW |
| 19 | XDXCLPXWGCLWX |
| 20 | DICLPRWGCLW |
| 21 | XDICLPRWGCLWX |
| 22 | DLCLRDWGCLW |
| 23 | MEDICLPRWGCLWGD |
| 24 | QRLMEDICLPRWGCLWEDDE |
| 25 | QGLIGDICLPRWGCLWGRSV |

TABLE 2-continued

| Albumin-binding domain sequences. | |
| --- | --- |
| SEQ ID NO | Amino Acid Sequence |
| 26 | QGLIGDICLPRWGCLWGRSVK |
| 27 | EDICLPRWGCLWEDD |
| 28 | RLMEDICLPRWGCLWEDD |
| 29 | MEDICLPRWGCLWEDD |
| 30 | MEDICLPRWGCLWED |
| 31 | RLMEDICLARWGCLWEDD |
| 32 | EWRSFCTRWPAEKSCKPLRG |
| 33 | RAPESFVCYWETICFERSEQ |
| 34 | EMCYFPGICWM |

In some embodiments, the albumin binding moiety comprises the following amino acid sequence motif: Xi-Cys-Xj-Cys-Xk, where the sum of i, j, and k is about 25 or less. In some embodiments, the sum is about 18 or less. In some embodiments, the sum is about 11 or less.

Transduction Domain

In some embodiments, a fusion protein of the disclosure comprises a transduction domain, which facilitates absorption by intestinal epithelial cells. In some embodiments, a fusion protein of the disclosure comprises a transduction domain that binds to a receptor on the surface of intestinal epithelial cells. In some embodiments, a fusion protein of the disclosure comprises a transduction domain that facilitates receptor-mediated endocytosis, transcytosis, and/or direct membrane translocation. In some embodiments, the transduction domain facilitates transcytosis. In some embodiments, the transduction domain binds to intestinal epithelial cells, or binds specifically to a tissue or organ. In some embodiments, the transduction domain comprises a CPP that binds to intestinal epithelial cells, or binds specifically to a tissue or organ.

In some embodiments, a fusion protein of the disclosure comprises a transduction domain selected from the list consisting of: GM1-binding peptides, the B subunit of cholera toxin (CTB), cell-penetrating peptides, and ligands and peptides that bind to intestinal receptors. In some embodiments, a fusion protein of the disclosure comprises a transduction domain that binds to intestinal receptors, such as the transferrin receptor, neonatal Fc receptor (FcRn), or integrins. In some embodiments, the transduction domain is selected from: a GM1 binding peptide, transferrin, antibody fragment crystallizable region (Fc region), and a dendritic cell peptide (DCpep). In some embodiments, the transduction domain comprises the sequence of FYPSYHSTPQRP (SEQ ID NO: 35).

In some embodiments, a fusion protein of the disclosure comprises a transduction domain that is a cell surface receptor, or fragment or ligand thereof. In some embodiments, the transduction domain is a cell surface receptor on intestinal epithelial cells, or fragment or ligand thereof. In some embodiments, the transduction domain comprises a ganglioside molecule, or an analog thereof.

In some embodiments, the transduction domain comprises a GM1 binding peptide. In some embodiments, the transduction domain comprises monosialotetrahexosylganglioside (GM1)-binding peptide. Ganglioside GM1 is an oligosaccharide lipid that is abundantly present on epithelial cells. As the largest mucosal area, the intestinal epithelium covers an area of 1.8-2.7 m². Approximately 15,000 GM1 molecules exist per cell. In some embodiments, a fusion protein of the disclosure comprises a GM1-binding peptide (BP) to facilitate the transport of the fusion protein, or a therapeutic moiety thereof, across the epithelial barrier. In some embodiments, the transduction domain is a GM1-BP selected from: Cholera Toxin B subunit (CTB), Heat-labile Enterotoxin B subunit (LTB), and an anti-GM1 antibody. In some embodiments, the transduction domain comprises the amino acid sequence of HLNILSTLWKYR (SEQ ID NO: 8). In some embodiments, the transduction domain comprises an amino acid sequence having 1, 2, 3, 4, or 5 amino acids different from SEQ ID NO: 8. In some embodiments, the GM1-binding peptide (BP) is fused to a solubility-enhancing domain, e.g., MBP, to facilitate the transport of the molecular cargo across the epithelial barrier. In some embodiments, the GM1-BP comprises the peptide sequence of VWRLLAPPFSNRLLP (SEQ ID NO: 75), WRL-LAPPFSNRLLP (SEQ ID NO: 76) or (W/F)RXL(X/P)(P/X)XFXX(R/X)(X/R)XP (SEQ ID NO: 77), where X can be any amino acid.

In some embodiments, the transduction domain comprises a cell-penetrating peptide (CPP). In certain embodiments, the fusion protein comprises a CPP to facilitate translocation across the intestinal epithelium and enhance systemic absorption following oral administration. In some embodiments, the CPP enables direct penetration of the epithelial cell membrane or promotes endocytic uptake. In some embodiments, the CPP is selected from the list consisting of: TAT, ATX-101, P28, PEP-010, R-Ahx-R repeat peptide, R7, PTD4, AVB-620 (ACPP), Pepducin, TransMTS, MTS, penetratin, transportan, polyarginine, TP10, MAP (model amphipathic peptide), Pep-1, and synthetic or chimeric peptides engineered for enhanced cellular uptake. In some embodiments, the CPP binds to PDX-1. In some embodiments, the CPP is penetratin. In some embodiments, the transduction domain comprises the amino acid sequence of RHIKIWFQNRRMKWKK (SEQ ID NO: 10). In some embodiments, the transduction domain comprises an amino acid sequence having 1, 2, 3, 4, or 5 amino acids different from SEQ ID NO: 10.

In some embodiments, the cell penetrating peptide (CPP) comprises an amino acid sequence disclosed in Table 3. In some embodiments, the CPP comprises an amino acid sequence having 1, 2, 3, 4, 5, 6, 7, 8, 9, or 10 amino acids different from an amino acid sequence disclosed in Table 3. In some embodiments, the CPP comprises an amino acid sequence having 1, 2, 3, 4, or 5 amino acids different from an amino acid sequence disclosed in Table 3. In some embodiments, the CPP comprises an amino acid sequence having at least about 70, 75, 80, 85, 90, 95, 96, 97, 98, or 99% sequence identity to an amino acid sequence disclosed in Table 3. In some embodiments, a fusion protein of the disclosure comprising an incretin agonist domain also comprises an amino acid sequence having at least about 80, 85, 90, 95, 96, 97, 98, or 99% sequence identity to an amino acid sequence disclosed in Table 3.

TABLE 3

Cell Penetrating Peptide Amino Acid Sequences

| CPP | Amino Acid Sequence (CPP portion) | Details, Source |
| --- | --- | --- |
| TAT | YGRKKRRQRRR (SEQ ID NO: 53) | Classic HIV-1 Tat (47-57). Variants: GRKKRRQRRRPPQ (SEQ ID NO: 78). |
| ATX-101 | DRQIKIWFQNRRMKWKK (SEQ ID NO: 54) | Penetratin-derived sequence. |
| AM-111 | YGRKKRRQRRR (TAT) (SEQ ID NO: 55) | Fused to JNK inhibitor domain. |
| P28 | LSTAADMQGVVTDGMASGLDKDYLKPDD (SEQ ID NO: 56) | Derived from bacterial azurin (28 aa). |
| ALRN-6924 | ETFSDLWKLLPEN (SEQ ID NO: 57) | p53 residues 17-29, stapled variant; parent sequence shown. |
| R7 | RRRRRRR (SEQ ID NO: 58) | Hepta-arginine. |
| (R-Ahx-R)$_4$ | R-Ahx-R repeated x4 (SEQ ID NO: 59) | Ahx = 6-aminohexanoic acid spacer. |
| TransMTS | YGRKKRRQRRRVR (SEQ ID NO: 60) | TAT/MTS hybrid. |
| MTS | YARVRRRGPRR (SEQ ID NO: 61) | From FGF-4 leader sequence. |
| AVB-620 (ACPP) | RRRRRRRRR (R$_9$) (SEQ ID NO: 62) | Poly-arginine CPP, activatable by protease cleavage. |
| Pepducin (PZ-128) | KKSRALF (lipidated) (SEQ ID NO: 63) | Derived from PAR-1 receptor loop. |
| BT1718 | RRRRRRRRR (R$_9$) (SEQ ID NO: 64) | Poly-arginine CPP, protease-activated conjugate. |
| PEP-010 | RQIKIWFQNRRMKWKK (SEQ ID NO: 65) | Penetratin sequence. |
| ATP128 | YGRKKRRQRRR (TAT-based) (SEQ ID NO: 66) | Used in self-adjuvanting vaccine platform. |
| TP10 (Transportan-10) | AGYLLGKINLKALAALAKKIL-amide (SEQ ID NO: 67) | Derived from galanin and mastoparan sequences; transportan analog. |
| MAP | KLALKLALKALKAALKLA (SEQ ID NO: 68) | Model Amphipathic Peptide; amphipathic α-helix, often amidated. |
| Pep-1 | KETWWETWWTEWSQPKKKRKV (SEQ ID NO: 69) | Amphipathic CPP used for protein delivery; contains hydrophobic tryptophan-rich and cationic domains. |
| PTD4 | YARAAARQARA (SEQ ID NO: 70) | Engineered CPP variant. |
| Charged oligopeptide | Poly-Lys (KKKKK) (SEQ ID NO: 71) or Poly-Arg (RRRRR) (SEQ ID NO: 72) | Designed synthetic CPPs. |

In some embodiments, a fusion protein of the disclosure comprises a transduction domain. In some embodiments, the fusion protein comprises one transduction domain. In some embodiments, the fusion protein comprises two or more transduction domains. In some embodiments, the fusion protein comprises 1, 2, 3, 4, 5, 6, 7, 8, 9, 10, 11, 12, 13, 14, or 15 transduction domains. In some embodiments, the fusion protein comprises 1, 2, 3, 4, or 5 transduction domains. In some embodiments, the fusion protein comprises two transduction domains. In some embodiments, the fusion protein comprises a GM1-binding peptide and a CPP. In some embodiments, the fusion protein comprises the GM1-binding peptide of SEQ ID NO: 8 and the CPP of SEQ ID NO: 10.

In some embodiments, the transduction domain is positioned at the N- and/or C-terminus of the fusion protein. In some embodiments, a GM1-binding peptide is positioned at the N-terminus, and a CPP is positioned at the C-terminus.

In some embodiments, a GM1-binding peptide is positioned at the C-terminus, and a CPP is positioned at the N-terminus. In some embodiments, the fusion protein comprises a transduction domain within the inner region of the protein, not at a terminus. In some embodiments, the GM1-binding peptide (BP) is fused to a solubility-enhancing domain, e.g., MBP, to increase stability of the molecular cargo expressed in host cells.

Solubility-Enhancing Domain

In some embodiments, a fusion protein of the disclosure comprises a solubility-enhancing domain, which improves solubility of the fusion protein. In some embodiments, the solubility-enhancing domain improves expression, folding, and/or stability of the fusion protein. In some embodiments, the solubility enhancing domain reduces aggregation, enhances yield, and/or facilitates purification. Suitable solubility tags include, but are not limited to, maltose-binding protein (MBP), cross-linked amylose/maltose, glutathione S-transferase (GST), SlyD, thioredoxin (Trx), galactose, ubiquitin, N-utilization substance A (NusA), small ubiquitin-like modifier (SUMO), and green fluorescent protein (GFP).

In some embodiments, the solubility-enhancing domain comprises MBP. In some embodiments, the solubility-enhancing domain comprises the amino acid sequence of SEQ ID NO: 9.

(SEQ ID NO: 9)
```
KIEEGKLVIWINGDKGYNGLAEVGKKFEKDTGIKVTVEHPDKLEEKFPQV

AATGDGPDIIFWAHDRFGGYAQSGLLAEITPDKAFQDKLYPFTWDAVRYN

GKLIAYPIAVEALSLIYNKDLLPNPPKTWEEIPALDKELKAKGKSALMFN

LQEPYFTWPLIAADGGYAFKYENGKYDIKDVGVDNAGAKAGLTFLVDLIK

NKHMNADTDYSIAEAAFNKGETAMTINGPWAWSNIDTSKVNYGVTVLPTF

KGQPSKPFVGVLSAGINAASPNKELAKEFLENYLLTDEGLEAVNKDKPLG

AVALKSYEEELVKDPRIAATMENAQKGEIMPNIPQMSAFWYAVRTAVINA

ASGRQTVDEALKDAQT.
```

In some embodiments, the solubility-enhancing domain comprises an amino acid sequence having 1, 2, 3, 4, 5, 6, 7, 8, 9, or 10 amino acids different from SEQ ID NO: 9. In some embodiments, the solubility-enhancing domain comprises an amino acid sequence having 1, 2, 3, 4, or 5 amino acids different from SEQ ID NO: 9. In some embodiments, the solubility-enhancing domain comprises an amino acid sequence having at least about 70, 75, 80, 85, 90, 95, 96, 97, 98, or 99% sequence identity to SEQ ID NO: 9. In some embodiments, the solubility-enhancing domain comprises an amino acid sequence having at least about 90, 95, 96, 97, 98, or 99% sequence identity to SEQ ID NO: 9.

In some embodiments, the solubility-enhancing domain comprises GST. In some embodiments, the solubility-enhancing domain comprises SlyD. In some embodiments, the solubility-enhancing domain comprises NusA. In some embodiments, the solubility-enhancing domain comprises cross-linked amylose/maltose. In some embodiments, the solubility-enhancing domain comprises thioredoxin. In some embodiments, the solubility-enhancing domain comprises DsbA. In some embodiments, the solubility-enhancing domain comprises DsbC. In some embodiments, the solubility-enhancing domain comprises ubiquitin. In some embodiments, the solubility-enhancing domain comprises SUMO.

Protease Cleavage Sites

In some embodiments, a fusion protein of the disclosure comprises a protease cleavage site. In some embodiments, a fusion protein of the disclosure comprises 1, 2, 3, 4, 5, 6, 7, 8, 9, or 10 protease cleavage sites. In some embodiments, a fusion protein of the disclosure comprises 2 protease cleavage sites.

In some embodiments, a fusion protein of the disclosure comprises a protease cleavage site that enables controlled release of a therapeutically active moiety. In some embodiments, the fusion protein comprises one or more protease cleavage sites to enable selective removal of functional domains, such as solubility-enhancing domains, affinity tags, and/or transduction domains. In some embodiments, the protease cleavage sites allow for removal of domains during purification and/or delivery. In some embodiments, the cleavage site is recognized by a site-specific protease. Suitable protease recognition sequences include, but are not limited to, those cleaved by tobacco etch virus (TEV) protease (e.g., ENLYFQ↓G, SEQ ID NO: 46), thrombin (e.g., LVPR↓GS, SEQ ID NO: 47), Factor Xa (e.g., IEGR↓, SEQ ID NO: 48), and enterokinase (e.g., DDDDK↓, SEQ ID NO: 49). In some embodiments, the cleavage site is engineered to be cleaved intracellularly or in response to environmental cues such as pH or specific enzymes present in the gastrointestinal tract.

In some embodiments, the protease cleavage site is cleaved by a protease selected from the list consisting of: furin, BACE1, BACE2, cathepsin D, cathepsin E, chymosin, napsin-A, nepenthesin, pepsin, presenilin, renin, papain, bromelain, cathepsin K, calpain, caspase-1, separase, adenain, pyroglutamyl-peptidase I, hepatitis C virus peptidase 2, sindbis virus-type nsP2 peptidase, dipeptidyl-peptidase VI, desi-1 peptidase, TEV protease, dmpA aminopeptidase, subtilisin, prolyl oligopeptidase, D-Ala-D-Ala peptidase C, signal peptidase I, lon-A peptidase, clp protease, rhomboid-1, chymotrypsin A, dipeptidase E, MMP-1, MMP-2, MMP-3, MMP-4, MMP-5, MMP-6, MMP-7, MMP-8, MMP-9, MMP-10, MMP-11, MMP-12, MMP-13, MMP-14, MMP-15, MMP-16, MMP-17, MMP-18, MMP-19, MMP-20, MMP-21, MMP-22, MMP-23, MMP-24, MMP-25, MMP-26, MMP-27, MMP-28, C-MMP, CA-MMP, X-MMP, interstitial collagenase, gelatinase-A, 72 kDa gelatinase, stromelysin 1, matrilysin, neutrophil collagenase, gelatinase-B, 92 kDa gelatinase, stromelysin 2, stromelysin 3, macrophage metalloelastase, collagenase 3, MT1-MMP, MT2-MMP, MT3-MMP, MT4-MMP, collagenase 4, stromelysin-4, enamelysin, MT5-MMP, MT6-MMP, amidophosphoribosyltransferase precursor, matrilysin-2, endometase, pump 1, rasi-1, murein tetrapeptidase 1d-carboxypeptidase, nucleoporin 145, penicillin g acylase precursor, phage klf endosialidase cimcd self-cleaving protein, gamma-glutamyl hydrolase, hedgehog protein, lactoferrin, and epilysin.

In some embodiments, the fusion protein comprises one or more protease cleavage sites that are specifically recognized by enzymes present in the gastrointestinal tract, such as those expressed by intestinal epithelial cells. These cleavage sites enable targeted release or activation of a therapeutic domain of a fusion protein herein upon oral administration. In some embodiments, a fusion protein of the disclosure comprises a cleavage sequence recognized by intestinal proteases such as trypsin (e.g., cleavage after lysine or arginine residues), chymotrypsin (e.g., cleavage after aromatic residues like phenylalanine, tyrosine, or tryptophan), or elastase (e.g., cleavage after small neutral residues such as alanine or valine). In some embodiments, the cleavage site is engineered to be selectively processed by membrane-bound or intracellular proteases, facilitating intracellular release of an active moiety.

In some embodiments, the fusion protein comprises a furin cleavage site. Furin is a proprotein convertase that plays a key role in processing precursor proteins by cleaving them at specific recognition sequences, typically at Arg-X-(Lys/Arg)-Arg↓ motifs. Furin is expressed in the trans-Golgi network, endosomes, and cell surface of many cell types, including intestinal epithelial cells. In some embodiments, a fusion protein of the disclosure comprises one or more furin cleavage sites. In some embodiments, a fusion protein of the disclosure comprises an Arg-X-(Lys/Arg)-Arg cleavage site. In some embodiments, a fusion protein of the disclosure comprises an RKKR (SEQ ID NO: 14) cleavage site. In some embodiments, a fusion protein of the disclosure comprises two furin cleavage sites. In some embodiments, a fusion protein of the disclosure comprises a furin cleavage site at each end of a therapeutic sequence comprised by the protein. In some embodiments, a fusion protein of the disclosure enters one of these cells via receptor-mediated endocytosis and is cleaved by furin to release an active therapeutic domain. In some embodiments, a furin cleavage site is recognized by furin, which cleaves a portion of the fusion protein while the fusion protein translocates across epithelial cells, but before entering circulation.

Affinity Tags

In some embodiments, a fusion protein of the disclosure comprises an affinity tag to facilitate purification, isolation, detection, or quantification of the expressed protein. In some embodiments, the tag is positioned at the N-terminus, C-terminus, or internally within the fusion construct. In some embodiments, the tag is removable via a protease cleavage site. In some embodiments, the tag is incorporated into the therapeutic moiety of the fusion protein. In some embodiments, a fusion protein of the disclosure comprises a tag selected from the list consisting of: polyhistidine tags (e.g., His6 or His10), glutathione S-transferase (GST), maltose-binding protein (MBP), Strep-tag, Strep-tag II, FLAG-tag, HA-tag, c-Myc tag, S-tag, thioredoxin (Trx), NusA, and SUMO (small ubiquitin-like modifier). In some embodiments, tags are used individually. In some embodiments, tags are used in combination (e.g., tandem affinity purification tags). In some embodiments, the affinity tags are compatible with a variety of affinity chromatography systems, including nickel-NTA, glutathione-Sepharose, amylose resin, and streptavidin-based matrices. In some embodiments, the tag also enhances solubility and/or stability of the fusion protein during expression and purification. In some embodiments, a fusion protein herein comprises a His-tag, e.g., a His6 tag.

Linkers, Spacers, and Hinges

In some embodiments, a fusion protein of the disclosure comprises one or more linker, spacer, or hinge sequences positioned between adjacent domains. In some embodiments, the linker, spacer, or hinge provides structural flexibility, reduces steric hindrance, and/or promotes proper folding and activity of individual domains. In some embodiments, the linker is a flexible, rigid, or cleavable sequence. In some embodiments, the linker comprises a glycine-and/or serine-rich sequence. In some embodiments, the linker comprises a motif selected from the list consisting of: a (Gly4)n motif (SEQ ID NO: 79), a (Gly4Ser)n motif (SEQ ID NO: 50), a Ser (Gly4Ser)n motif, GGGGS GGGGS GGGGS AL (SEQ ID NO: 80), GGGGS GGGGS GGGGS A (SEQ ID NO: 81), and combinations thereof, wherein n is a positive integer from 1 to 10. In some embodiments, n is an integer from 1 to 6. In some embodiments, the linker comprises EAAAK (SEQ ID NO: 51) repeats or proline-rich motifs to maintain fixed spacing. In some embodiments, the linker comprises n repeats of GS, GGS, or GSG, where n is an integer from 1 to 20. In some embodiments, n is an integer from 1 to 10. In some embodiments, the linker comprises a protease cleavage site to allow post-translational separation of domains.

In some embodiments, a fusion protein of the disclosure comprises a linker positioned between any two domains of the fusion protein. In some embodiments, a fusion protein of the disclosure comprises a linker between a solubility-enhancing domain and a protease cleavage site. In some embodiments, a fusion protein of the disclosure comprises a linker positioned between a solubility-enhancing domain and a molecular cargo domain. In some embodiments, a fusion protein of the disclosure comprises a linker positioned between a transduction domain and a molecular cargo domain.

In some embodiments, a fusion protein of the disclosure comprises a hinge derived from an immunoglobulin domain. In some embodiments, a fusion protein of the disclosure comprises a hinge derived from an IgG1 hinge. In some embodiments, a fusion protein of the disclosure comprises a hinge between the transduction domain and the solubility-enhancing domain. In some embodiments, the hinge region comprises an amino acid sequence of SEQ ID NO: 11 (GPGP).

In some embodiments, the fusion protein comprises one or more spacer sequences positioned between adjacent domains to provide minimal separation between two adjacent sequences. In some embodiments, a fusion protein of the disclosure comprises a spacer sequence comprising a short dipeptide or tripeptide. In some embodiments, the spacer comprises serine-valine (SV), glycine-serine (GS), or alanine-glycine (AG), which offer limited flexibility while maintaining compactness. These short spacers may be particularly useful in constructs where domain proximity is desired but direct fusion may impair folding or activity. The choice of linker, spacer or hinge may be optimized based on the size, function, and interaction requirements of the fused domains.

In some embodiments, a fusion protein of the disclosure comprises a linker comprising the sequence of NSSSNNNNNNNNNNLG (SEQ ID NO: 12), or a variant thereof. In some embodiments, a fusion protein of the disclosure comprises a linker comprising the sequence of GGGGSGGGGSGGGGS (SEQ ID NO: 13), or a variant thereof. In some embodiments, a fusion protein of the disclosure comprises a hinge comprising the sequence of GPGP (SEQ ID NO: 11). In some embodiments, a fusion protein of the disclosure comprises a spacer comprising the sequence SV. In some embodiments, a fusion protein of the disclosure comprises 1, 2, 3, 4, 5, 6, 7, 8, 9, or 10 linkers, spacers, and hinges.

Domain Organization

In some embodiments, the techniques described herein relate to a fusion protein, wherein the fusion protein comprises at least one molecular cargo domain (M). In some embodiments, the fusion protein comprises a transduction domain (TD). In some embodiments, the fusion protein comprises at least two TDs. In some embodiments, the fusion protein comprises a solubility domain (SD). In some embodiments, the fusion protein comprises one or more SDs. In some embodiments, the fusion protein comprises zero, one, or more protease cleavage sites (C) interspersed between other domains.

In some embodiments the TDs are located on the N- and C-terminus of the fusion protein. In some embodiments the TDs are placed in tandem on the N- or C-terminal of the fusion protein. In some embodiments there are a series of 2 or more TDs in tandem interrupted by the M or SD domains.

In some embodiments there is only one copy of the M in the fusion protein. In some embodiments there are multiple copies of the same M in the fusion protein either in tandem or interspersed with TDs or SDs. In some embodiments there are multiple different Ms present in the fusion protein either in tandem or interspersed with TDs and SDs. In some embodiments the M or Ms are present on the N- or C-terminus. In some embodiments the Ms are present on the N- and C-terminus. In some embodiments the M or Ms are placed within the fusion protein flanked by TDs or SDs on both the N- and C-terminal of the M or Ms.

A C may be placed between any defined domain or may be absent entirely. Each C present in the fusion protein may correspond to the same enzyme, or they may correspond to different enzymes to facilitate staged processing of the fusion protein.

Incretin Agonist Mimetics

The present disclosure provides novel incretin agonist mimetics. In some embodiments, the incretin agonist mimetic binds to GLP-1R and/or GIPR. In some embodiments, the incretin agonist mimetic binds to both GLP-1R and GIPR. In some embodiments, the incretin agonist mimetic is a dual incretin agonist mimetic having the sequence of X1-X2-X3-Gly-Thr-Phe-X7-Ser-X9-X10-X11-Ile-X13-X14-X15-X16-X17-Ala-X19-X20-X21-X22-X23-X24-Trp-Leu-X27-X28-X29-X30-X31-X32-X33-X34-X35-X36-X37-X38-X39-X40-X41-X42 (SEQ ID NO: 16), wherein X1 is His or Tyr; X2 is Ala, Gly, or aminoisobutyric acid (Aib); X3 is Glu or Asp; X7 is Thr, Ser, or Ile; X9 is Asp or Glu; X10 is Tyr, Leu, or Ser; X11 is Ser or Leu; X13 is Ala, Tyr, Aib, or alpha-methyl-L-leucine (αMeL); X14 is Met, Leu, or Ser; X15 is Asp or Glu; X16 is Lys, Gly, Ser, or Glu; X17 is Ile, Lys, Gln, Arg, or Glu; X19 is Gln, Ala, Glu, or Lys; X20 is Gln, Lys, or Arg; X21 is Asp, Ala, or Glu; X22 is Phe; X23 is Val, Ile, or Leu; X24 is Gln, Asn, Glu, Arg or Lys; X27 is Leu, Val, Ile, Lys, Glu, or Ser; X28 is Ala, Ser, Arg, or Aib; X29 is Gln, Glu, Lys, Gly, Tyr, or Aib; X30 is Lys, Gly, Pro, or absent; X31 is Gly, Pro, Ser, Glu, or absent; X32 is Lys, Ser, or absent; X33 is Lys, Ser, Glu, or absent; X34 is Asn, Gly, Ala, Lys, or absent; X35 is Asp, Ala, Pro, Glu, or absent; X36 is Trp, Pro, Lys, or absent; X37 is Lys, Pro, Glu, or absent; X38 is His, Pro, Ser, Lys, or absent; X39 is Asn, Ser, or absent; X40 is Ile or absent; X41 is Thr or absent; and X42 is Gln or absent. In some embodiments, the incretin agonist mimetic comprises an amino acid sequence having at least about 70, 75, 80, 85, 90, 95, 96, 97, 98, or 99% sequence identity to SEQ ID NO: 16. In some embodiments, the incretin agonist mimetic comprises an amino acid sequence having at least about 90, 95, 96, 97, 98, or 99% sequence identity to SEQ ID NO: 16. In some embodiments, the incretin agonist mimetic comprises an amino acid sequence having at least about 87, 89, 92, 94, or 97% sequence identity to SEQ ID NO: 16. In some embodiments, the incretin agonist mimetic comprises an amino acid sequence having at least about 90% sequence identity to SEQ ID NO: 16.

In some embodiments, the incretin agonist mimetic comprises the amino acid sequence YGEGTFTSDYSIALDKI-AQKAFVQWLIAGGPSSGAPPPS (SEQ ID NO: 2). In some embodiments, the incretin agonist mimetic comprises an amino acid sequence having 1, 2, 3, 4, 5, 6, 7, 8, 9, or 10 amino acids different from SEQ ID NO: 2. In some embodiments, the incretin agonist mimetic comprises an amino acid sequence having 1, 2, 3, 4, or 5 amino acids different from SEQ ID NO: 2. In some embodiments, the incretin agonist mimetic comprises an amino acid sequence having at least about 70, 75, 80, 85, 90, 95, 96, 97, 98, or 99% sequence identity to SEQ ID NO: 2. In some embodiments, the incretin agonist mimetic comprises an amino acid sequence having at least about 90, 95, 96, 97, 98, or 99% sequence identity to SEQ ID NO: 2. In some embodiments, the incretin agonist mimetic comprises an amino acid sequence having at least about 87, 89, 92, 94, or 97% sequence identity to SEQ ID NO: 2. In some embodiments, the incretin agonist mimetic comprises an amino acid sequence having at least about 90% sequence identity to SEQ ID NO: 2. SEQ ID NO: 2 can bind both GLP-1 and GIP receptors while also increasing its half-life in the system. Additionally, the binding affinities to both receptors were found to be higher than those of their corresponding incretins.

In some embodiments, the incretin agonist mimetic comprises the amino acid sequence YGQGTFTSDYSIYLDKQAQQAFIEYL-LEGGPSSGAPPPS (SEQ ID NO: 17). In some embodiments, the incretin agonist mimetic comprises an amino acid sequence having 1, 2, 3, 4, 5, 6, 7, 8, 9, or 10 amino acids different from SEQ ID NO: 17. In some embodiments, the incretin agonist mimetic comprises an amino acid sequence having 1, 2, 3, 4, or 5 amino acids different from SEQ ID NO: 17. In some embodiments, the incretin agonist mimetic comprises an amino acid sequence having at least about 70, 75, 80, 85, 90, 95, 96, 97, 98, or 99% sequence identity to SEQ ID NO: 17. In some embodiments, the incretin agonist mimetic comprises an amino acid sequence having at least about 90, 95, 96, 97, 98, or 99% sequence identity to SEQ ID NO: 17. In some embodiments, the incretin agonist mimetic comprises an amino acid sequence having at least about 90% sequence identity to SEQ ID NO: 17.

Nucleic Acids, Vectors, and Host Cells

The present disclosure also provides nucleic acids encoding the fusion proteins of the disclosure.

Also provided are vectors encoding a fusion protein of the disclosure or comprising the nucleic acids encoding the fusion proteins of the disclosure. In some embodiments, the vector is a plasmid. In some embodiments, the vector comprises an expression cassette having two or more of: (a) a promoter element, (b) a signal peptide, (c) a nucleotide sequence encoding a fusion protein, and (d) a terminator element.

The present disclosure also provides host cells expressing and/or comprising the fusion proteins of the disclosure. In some embodiments, the host cell comprises a fusion protein, nucleic acid, and/or vector disclosed herein. In some embodiments, the fusion protein is stably or transiently expressed in the host cell.

In some embodiments, the host cell is a prokaryotic cell or a eukaryotic cell. In some embodiments, the host cell is a yeast cell, algal cell, cyanobacteria, or plant cell. In some embodiments, the host cell is a yeast cell. In some embodiments, the host cell is a species of *Saccharomyces, Pichia,* or *Arthrospira.* In some embodiments, the host cell is a species of *Saccharomyces.* In some embodiments, the host cell is *Saccharomyces cerevisiae.*

Aspects of the present disclosure include a method of making a fusion protein, the method comprising: transfecting a host cell with one or more vectors comprising a nucleic acid encoding the fusion protein; and recombinantly expressing the fusion protein in the host cell, wherein the fusion protein is secreted by the host cell into a culture media. In some embodiments, the method further comprises optionally purifying the fusion protein. In some embodiments, the method further comprises lyophilizing the host cell or the purified fusion protein.

In some aspects, the present disclosure provides a biodelivery platform comprising a host-cell encapsulated fusion protein comprising a molecular cargo. In some embodiments, a biodelivery platform herein comprises a host cell expressing a fusion protein of the disclosure. In some embodiments, the biodelivery platform comprises a host cell-encapsulated fusion protein, wherein the host cell has been dried, lyophilized, and/or ground into a powder. In some embodiments, the powdered host cell is encapsulated or otherwise formed into a tablet for oral consumption. In some embodiments, this biodelivery platform enhances stability, bioavailability, and therapeutic efficacy.

In some embodiments, the host cell encapsulating a fusion protein of the disclosure is a yeast, algae, or plant cell. In some embodiments, the host cell is a yeast cell. In some embodiments, the host cell is *Saccharomyces cerevisiae*. *S. cerevisiae* is a unicellular fungus, with a sequenced genome (Goffeau et al 1996), which is used for a variety of industrial applications, including the production of many fermented beverages, such as wine, beer and cider; and distilled beverages, such as rum, vodka, whisky, brandy, and sake (Parapouli et al 2020). *S. cerevisiae* has also been linked to weight loss in some studies (Briskey et al. 2024; Jung et al. 2014). Yeast hydrolysate (yeast extract purified from baker's yeast by hydrolysis) has been shown to increase weight loss in obese adults leading to lower body mass indexes and reduced abdominal fat. It is thought to achieve this through suppression of appetite. Yeast may also improve aspects of diabetes including a reduction in fasting blood sugar and insulin resistance. In a study investigating chromium-enriched yeast, a difference in HbAlc levels between treatment and placebo was shown, indicating an improvement in glucose control. See Jung et al., *Prev Nutr Food Sci* 2017; 22 (1): 45-49; Bahijiri et al., *Saudi Med J* 2000; 21 (9): 831-7; and Racek et al., *Biol Trace Elem Res* 2006; 109 (3): 215-30.

In some embodiments, the biodelivery platform comprises a host cell, e.g., a yeast cell, expressing the incretin agonist, e.g., in a fusion protein herein.

In some embodiments, the fusion protein is expressed in a host cell, such as yeast, algae, or plant cells, that is suitable for oral delivery, e.g., via encapsulated or lyophilized formulations.

In some embodiments, the host cell is lyophilized. In some embodiments, the host cell is in powder form. In some embodiments, the host cell is a powder within a tablet.

Methods of Manufacturing

The present disclosure provides methods of manufacturing the fusion proteins of the disclosure.

In some embodiments, a method of manufacturing a fusion protein of the disclosure comprises expressing a nucleic acid encoding the fusion protein in a suitable host cell. In some embodiments, the host cell is selected from the group consisting of: *Escherichia coli, Saccharomyces cerevisiae, Pichia pastoris*, Chinese hamster ovary (CHO) cells, HEK293 cells, insect cells, and other mammalian, bacterial, yeast, and fungal expression systems.

In some embodiments, the method comprises culturing the host cell under conditions suitable for expression of the fusion protein, followed by harvesting the expressed protein from the culture medium or cell lysate.

In some embodiments, the method comprises purifying the fusion protein using one or more purification techniques selected from the group consisting of: affinity chromatography, ion exchange chromatography, size exclusion chromatography, hydrophobic interaction chromatography, and reverse-phase chromatography.

In some embodiments, the method comprises refolding the fusion protein following purification, wherein the refolding conditions are selected to optimize biological activity, solubility, or structural integrity of the fusion protein.

In some embodiments, the method comprises chemically modifying the fusion protein post-expression, wherein the modification is selected from the group consisting of: PEGylation, glycosylation, lipidation, acetylation, or conjugation to a carrier molecule.

In some embodiments, the method of manufacturing a fusion protein comprises chemically modifying the fusion protein by lipidation. In some embodiments, a fatty acid moiety is covalently attached to one or more lysine residues of the fusion protein. In some embodiments, the fatty acid is selected from the group consisting of: palmitic acid, stearic acid, myristic acid, oleic acid, linoleic acid, and other saturated or unsaturated fatty acids. In some embodiments, the lipidation is performed using activated fatty acid derivatives, such as N-hydroxysuccinimide (NHS) esters, acid chlorides, or carbodiimide-mediated coupling agents, under conditions suitable for selective acylation of lysine side chains. In some embodiments, the lipidation enhances the pharmacokinetic properties of the fusion protein, including increased plasma half-life, improved membrane association, or enhanced cellular uptake. In some embodiments, the lipidation is site-specific, wherein lysine residues are engineered or selected to enable controlled modification without disrupting the biological activity or structural integrity of the fusion protein.

In some embodiments, the method of manufacturing a fusion protein comprises chemically synthesizing the fusion protein. In some embodiments, the fusion protein is synthesized using solid-phase peptide synthesis (SPPS). In some embodiments, the synthesis is performed using Fmoc or Boc chemistry, wherein amino acids are sequentially added to a growing peptide chain anchored to a solid resin.

In some embodiments, the method comprises synthesizing individual peptide domains of the fusion protein separately, followed by chemical ligation to form the full-length fusion protein. In some embodiments, the ligation is performed using native chemical ligation, enzymatic ligation, or click chemistry.

In some embodiments, the method comprises incorporating non-natural amino acids, D-amino acids, or chemically modified residues into the fusion protein during synthesis to enhance stability, bioavailability, or receptor selectivity.

In some embodiments, the method comprises cyclizing one or more domains of the fusion protein to improve conformational stability or resistance to proteolytic degradation. Cyclization may be achieved via disulfide bond formation, head-to-tail cyclization, or side-chain crosslinking.

In some embodiments, the method comprises conjugating the fusion protein to a carrier molecule, such as polyethylene glycol (PEG), a lipid moiety, or a targeting ligand, using chemical crosslinkers or reactive functional groups.

In some embodiments, the method comprises formulating the fusion protein into a pharmaceutical composition, wherein the formulation comprises one or more pharmaceutically acceptable excipients, stabilizers, buffers, or delivery agents.

In some embodiments, the method comprises lyophilizing the fusion protein for long-term storage, wherein the lyophilized product is reconstituted prior to administration.

In some embodiments, the method comprises validating the identity, purity, and activity of the fusion protein using analytical techniques selected from the group consisting of: SDS-PAGE, Western blotting, ELISA, mass spectrometry, HPLC, and bioassays.

Methods of Treatment

The present disclosure provides methods of treating a subject with a biodelivery platform of the disclosure. The present disclosure provides methods of treating a subject with a fusion protein of the disclosure.

In some embodiments, the subject has a condition. In some embodiments, the condition is a hormonal disorder. In some embodiments, the condition is a cardiovascular disorder. In some embodiments, the condition is a neurological disorder. In some embodiments, the condition is a pain disorder. In some embodiments, the condition is an onco-logical disorder. In some embodiments, the condition is an infectious disease. In some embodiments, the condition is an immune disorder. In some embodiments, the condition is an inflammatory disorder. In some embodiments, the condition is a gastrointestinal disorder. In some embodiments, the condition is a dermatological disorder. In some embodi-ments, the condition is a wound healing disorder. In some embodiments, the condition is a musculoskeletal disorder. In some embodiments, the condition is a hematological disor-der. In some embodiments, the condition is a metabolic disorder. In some embodiments, the condition is an appetite disorder.

In some embodiments, the condition is selected from the list consisting of: diabetes mellitus, severe hypoglycemia, osteoporosis, Paget's disease, obesity, metabolic syndrome, vasodilatory shock, diabetes insipidus, postpartum hemor-rhage, labor induction, prostate cancer, breast cancer, endo-metriosis, precocious puberty, heart failure, hypertension, pulmonary arterial hypertension, acute pain, chronic pain, depression, mood disorders, nausea, vomiting, pain syn-dromes, schizophrenia, Parkinson's disease, neuroendocrine tumors, acromegaly, bacterial infections, viral infections, fungal infections, autoimmune diseases, immune deficien-cies, inflammatory disorders, gastroparesis, anorexia, cachexia, peptic ulcers, irritable bowel syndrome (IBS), functional dyspepsia, skin aging, psoriasis, eczema, chronic wounds, infected wounds, muscle wasting, fibrosis, muscu-lar dystrophy, sarcopenia, anemia, fertility regulation, repro-ductive hormone imbalance, appetite dysregulation, eating disorders, and cancer. In some embodiments, the condition is an imaging need.

In some embodiments, a fusion protein of the disclosure comprising an incretin agonist domain is employed in a method for the treatment or prevention of one or more metabolic, endocrine, or inflammatory conditions. In some embodiments, the condition is associated with obesity. In some embodiments, the condition is associated with a lack of or diminished production of insulin. In some embodi-ments, the condition is type 2 diabetes mellitus, hyperten-sion, obesity, metabolic syndrome, or non-alcoholic fatty liver disease (NAFLD), obesity-linked gallbladder disease, obesity-induced sleep apnea, excessive appetite, fatty liver disease, dyslipidemia, metabolic syndrome, insufficient sati-ety, hyperinsulinemia, insulin resistance syndrome, syn-drome X, and hypoglycemia. In some embodiments, the condition is diabetes. In some embodiments, the condition is type 1 diabetes, type 2 diabetes, or gestational diabetes.

In some embodiments, the disclosure provides a method of reducing the risk of or treating cardiovascular diseases, such as atherosclerosis, myocardial infarction, or stroke. In some embodiments, a composition of the disclosure is used in a method of treating or preventing neurodegenerative diseases (e.g., Alzheimer's disease). In some embodiments, a composition of the disclosure is used to treat or prevent polycystic ovary syndrome (PCOS). In some embodiments, the method is a method of treating addiction. In some embodiments, the method is a method of increasing longev-ity.

In some embodiments, the subject is experiencing or is at risk for a disease or condition associated with weight gain. In some embodiments, the disease or condition is selected from one or more of: diabetes, excessive weight gain, obesity, and poor cardiovascular health. In some embodi-ments, the weight gain associated condition is obesity. In some embodiments, the weight gain associated condition is excessive weight gain. In some embodiments, the weight gain associated condition is diabetes mellitus. In some embodiments, the weight gain associated condition is insulin insensitivity. In some embodiments, the weight gain asso-ciated condition is cardiovascular disease. In some embodi-ments, the condition is obesity-linked gallbladder disease. In some embodiments, the weight gain associated condition is obesity-induced sleep apnea. In some embodiments, the condition is diabetes. In some embodiments, the weight gain associated condition is excessive appetite. In some embodi-ments, the weight gain associated condition is fatty liver disease. In some embodiments, the weight gain associated condition is non-alcoholic fatty liver disease (NASH).

In some embodiments, the methods described herein lead to weight loss. In some embodiments, the methods lead to a weight loss of 0.5-20% of original body weight. In some embodiments, the methods herein lead to a weight loss of 1-10% of original body weight. In some embodiments, weight loss is observed over a period of 1, 2, 3, 4, 5, 6, 7, 8, 9, 10, 11, or 12 weeks. In some embodiments, weight loss is observed over a period of 1, 2, 3, or 4 weeks. In some embodiments, weight loss is observed over a period of 1, 2, 3, 4, 5, 6, 7, 8, 9, 10, 11, or 12 months.

In some embodiments, a treatment method of the disclo-sure comprises administering a therapeutically effective amount of a fusion protein of the disclosure. In some embodiments, an incretin agonist fusion protein of the disclosure is administered to a subject in need thereof in a therapeutically effective amount sufficient to achieve glyce-mic control.

In some embodiments, the condition is an endocrine disorder. In some embodiments, the endocrine disorder is selected from growth hormone deficiency, gigantism, Cush-ing's syndrome, Addison's disease, hypothyroidism, hyper-thyroidism, Graves' disease, or Hashimoto's thyroiditis.

In some embodiments, the condition is a reproductive hormone disorder. In some embodiments, the disorder is selected from hypogonadism, luteinizing hormone defi-ciency, follicle-stimulating hormone deficiency, menopause-related symptoms, or infertility.

In some embodiments, the condition is a neurological disorder. In some embodiments, the disorder is selected from multiple sclerosis (MS), amyotrophic lateral sclerosis (ALS), Huntington's disease, epilepsy, migraine, neuro-pathic pain, cognitive impairment, vascular dementia, nar-colepsy, insomnia, or circadian rhythm disorders.

In some embodiments, the condition is a cardiovascular or renal disorder. In some embodiments, the disorder is selected from arrhythmias, cardiomyopathy, peripheral arte-rial disease, chronic kidney disease, diabetic nephropathy, pulmonary fibrosis, or chronic obstructive pulmonary dis-ease (COPD).

In some embodiments, the condition is an oncological disorder. In some embodiments, the oncological disorder is selected from leukemia, lymphoma, multiple myeloma, col-orectal cancer, pancreatic cancer, gastric cancer, liver cancer, ovarian cancer, cervical cancer, uterine cancer, melanoma, or other skin cancers.

In some embodiments, the condition is an infectious disease. In some embodiments, the infectious disease is selected from malaria, leishmaniasis, schistosomiasis, HIV infection, hepatitis B, hepatitis C, influenza, respiratory syncytial virus (RSV), or COVID-19.

In some embodiments, the condition is an immune or inflammatory disorder. In some embodiments, the condition is selected from allergic rhinitis, asthma, food allergies, atopic dermatitis, myasthenia gravis, pemphigus vulgaris, systemic sclerosis, systemic lupus erythematosus, familial Mediterranean fever (FMF), or cryopyrin-associated periodic syndrome (CAPS).

In some embodiments, the condition is a gastrointestinal or hepatic disorder. In some embodiments, the disorder is selected from Crohn's disease, ulcerative colitis, celiac disease, hepatitis, cirrhosis, cholestatic liver disease, or primary biliary cholangitis.

In some embodiments, the condition is a musculoskeletal disorder. In some embodiments, the disorder is selected from osteoarthritis, rheumatoid arthritis, psoriatic arthritis, tendinopathy, impaired bone healing, or immobilization-induced bone loss.

In some embodiments, the condition is a dermatological disorder. In some embodiments, the disorder is selected from vitiligo, alopecia areata, blistering skin disorders, scleroderma, chronic pruritus, or keloid scarring.

In some embodiments, the condition is a hematological disorder. In some embodiments, the disorder is selected from hemophilia A, hemophilia B, von Willebrand disease, sickle cell disease, thalassemia, or lysosomal storage diseases including Gaucher disease, Fabry disease, Pompe disease, and mucopolysaccharidoses (MPS).

In some embodiments, the condition is an ophthalmological disorder. In some embodiments, the disorder is selected from age-related macular degeneration (AMD), diabetic retinopathy, or retinitis pigmentosa.

In some embodiments, the condition is a respiratory disorder. In some embodiments, the condition is cystic fibrosis or idiopathic pulmonary fibrosis.

In some embodiments, the condition is a nephrological disorder. In some embodiments, the disorder is polycystic kidney disease.

In some embodiments, the method is a method of promoting longevity. In some embodiments, the condition is associated with cellular senescence, frailty, or age-related decline.

In some embodiments, the method is a vaccination method. In some embodiments, the method comprises oral mucosal delivery of a vaccine selected from viral vaccines, bacterial vaccines, or cancer vaccines.

In some embodiments, the method is a method of treating, preventing, or reducing the risk of any disease, disorder, or condition that is amenable to treatment with a therapeutic protein, peptide, or fusion protein, wherein the therapeutic protein, peptide, or fusion protein is delivered by the oral bio-delivery platform of the disclosure.

Administration and Dosing

In some embodiments, a composition of the disclosure is formulated for administration to a subject in need thereof. In some embodiments, the composition is formulated as a liquid composition. In some embodiments, the composition is formulated as a solid composition. In some embodiments, the composition is formulated for oral delivery. In some embodiments, the composition is formulated for oral delivery in a solid dosage form. In some embodiments, the composition is formulated as a solid oral dosage form, including but not limited to tablets, caplets, capsules, granules, and powders. In some embodiments, the solid dosage form is enteric-coated to protect the fusion protein from degradation in the gastric environment.

In some embodiments, an incretin agonist composition of the disclosure is formulated as a liquid dosage form, including solutions, suspensions, emulsions, or syrups. In some embodiments, the liquid formulation is buffered to maintain protein stability. In some embodiments, the liquid formulation is packaged in single-use or multi-dose containers.

In some embodiments, the composition is lyophilized and reconstituted prior to administration. In some embodiments, the lyophilized powder is provided in a vial or pre-filled syringe with a suitable diluent.

In some embodiments, the composition is formulated for oral, subcutaneous, intravenous, intramuscular, or transdermal administration. In some embodiments, the composition is formulated for oral administration. In some embodiments, oral administration comprises per os, sublingual, buccal, oromucosal, oral transmucosal, lingual, or gingival administration. In some embodiments, oral administration comprises per os administration. In some embodiments, the composition is formulated for subcutaneous injection. In some embodiments, subcutaneous administration is performed using a pre-filled syringe, autoinjector, or pen device. In some embodiments, a composition of the disclosure is formulated for sublingual administration. In some embodiments, compositions for sublingual administration contain a polymeric carrier matrix suitable for sublingual delivery.

In some embodiments, the composition includes one or more pharmaceutically acceptable excipients and/or carriers. In some embodiments, the composition includes an excipient to enhance stability, bioavailability, or gastrointestinal transit. In some embodiments, the composition comprises an enteric coating or absorption enhancer to facilitate intestinal uptake of the incretin agonist composition. In some embodiments, the composition comprises one or more excipients selected from the group consisting of binders, fillers, disintegrants, lubricants, glidants, stabilizers, surfactants, antioxidants, preservatives, and solubilizers. In some embodiments, the composition comprises an absorption enhancer. In some embodiments, the composition comprises a buffering agent. In some embodiments, the composition comprises a cryoprotectant and/or lyoprotectant. In some embodiments, the composition comprises water, buffered solutions, glucose solutions, and/or culture fluids. In some embodiments, the composition comprises excipients such as stabilizers, preservatives, diluents, emulsifiers and lubricants. In some embodiments, a composition of the disclosure comprises a pharmaceutically acceptable carrier or diluent selected from the list consisting of: stabilizers such as carbohydrates (e.g., sorbitol, mannitol, starch, sucrose, glucose, dextran), proteins such as albumin or casein, protein-containing agents such as bovine serum or skimmed milk and buffers (e.g., phosphate buffer). In some embodiments, the composition is suitable for freeze-drying or spray-drying. In some embodiments, a composition of the disclosure contains a fusion protein of the disclosure in a suitable dosage form. In some embodiments, the dosage form is selected from the group consisting of injections, capsules, tablets, pills, nasal sprays, or aerosols. In some embodiments, the composition is prepared for a mode of administration selected from the list consisting of: oral administration, intravenous injection, intravenous drip, subcutaneous or intramuscular injection. In some embodiments, the mode of administration is oral.

In some embodiments, a composition of the disclosure comprises a filler selected from the list consisting of: rice flour, microcrystalline cellulose, lactose monohydrate, mannitol, dicalcium phosphate, starch, pregelatinized starch, calcium carbonate, and sorbitol. In some embodiments, the composition comprises rice flour. In some embodiments, the composition comprises an excipient to prevent clumping. In some embodiments, the composition comprises an excipient selected from the list consisting of: bamboo silica, colloidal silicon dioxide, fumed silica, magnesium stearate, talc, calcium silicate, microcrystalline cellulose, starch, and hydroxypropyl cellulose. In some embodiments, the composition comprises bamboo silica. In some embodiments, the composition comprises a lubricant and anti-sticking excipient. In some embodiments, the composition comprises an excipient selected from the list consisting of: calcium laurate, magnesium stearate, stearic acid, glyceryl behenate, sodium stearyl fumarate, and hydrogenated vegetable oil. In some embodiments, the composition comprises calcium laurate.

In some embodiments, an incretin agonist composition of the disclosure is administered 1, 2, 3, 4, 5, 6, 7, 8, 9, or 10 times each day. In some embodiments, an incretin agonist composition of the disclosure is administered 1, 2, or 3 times each day. In some embodiments, the composition is administered twice daily. In some embodiments, the composition is administered once daily. In some embodiments, the composition is administered every other day. In some embodiments, the composition is administered once per week. In some embodiments, the composition is administered once every 2, 3, 4, 5, 6, 7, 8, 9, 10, 11, 12, 13, or 14 days. In some embodiments, the composition is administered once every 2, 3, 4, 5, 6, or 7 days.

In some embodiments, the dosage is titrated, e.g., starting once a day and then increasing to twice or three times daily. In some embodiments, titration is implemented over a period of 1 to 20 weeks. In some embodiments, titration is implemented over a period of 1 to 12 months.

In some embodiments, the composition is administered in a fasted state. In some embodiments, the composition is administered prior to food and beverage intake. In some embodiments, the composition is administered at least about 5, 10, 20, 30, 40, 50, 60, 70, 80, 90, 100, 110, or 120 minutes before food or beverage intake. In some embodiments, the composition is administered about 5, 10, 20, 30, 40, 50, 60, 70, 80, 90, 100, 110, or 120 minutes before food or beverage intake. In some embodiments, the composition is administered at least about 30 minutes before food or beverage intake. In some embodiments, the composition is administered 1-3 times daily, before a meal.

In some embodiments, the composition is administered during or after food and/or beverage intake. In some embodiments, the composition is administered with food. In some embodiments, the composition is administered at least about 5, 10, 20, 30, 40, 50, 60, 70, 80, 90, 100, 110, or 120 minutes after food or beverage intake. In some embodiments, the composition is administered about 5, 10, 20, 30, 40, 50, 60, 70, 80, 90, 100, 110, or 120 minutes after food or beverage intake. In some embodiments, the composition is administered at least about 30 minutes after food or beverage intake. In some embodiments, the composition is administered 1-3 times daily, with or after a meal.

In some embodiments, a composition of the disclosure, e.g., a fusion protein of the disclosure, is administered in a dosage of between about 0.05 mg to about 200 mg per dose. In some embodiments, the composition is administered in a dosage of between about 0.1 mg and about 100 mg per dose. In some embodiments, the composition is administered in a dosage of between about 0.25 mg and about 50 mg per dose. In some embodiments, the composition is administered in a dosage of between about 0.5 mg and about 1 mg per dose. In some embodiments, the composition is administered in a dosage of between about 0.8 mg and about 0.9 mg per dose. In some embodiments, the composition is administered in a dosage of about 0.85 mg per dose.

In some embodiments, a composition of the disclosure is administered in a dose of about 0.1 to 500 mg/kg/day, including all ranges and subranges therebetween. In some embodiments, a composition of the disclosure is administered in a dose of about 0.1, 0.5, 0.75, 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 mg/kg/day, including all ranges and subranges therebetween.

In some embodiments, a fusion protein of the disclosure is comprised in a host cell of the disclosure, e.g., a dried, lyophilized, and powdered *Saccharomyces cerevisiae*. In some embodiments, a host cell composition of the disclosure is administered in a dose of between about 10 mg and about 2 g. In some embodiments, a host cell composition of the disclosure is administered in a dose of between about 50 mg and about 1000 mg. In some embodiments, a host cell composition of the disclosure is administered in a dose of between about 100 mg and about 500 mg. In some embodiments, a host cell composition of the disclosure is administered in a dose of about 200 mg.

In some embodiments, a fusion protein of the disclosure is administered in a solid oral dosage form comprising a therapeutically effective amount of a modified *Saccharomyces cerevisiae* strain expressing the fusion protein. In some embodiments, the dietary supplement is formulated for oral administration in a solid dosage form. Suitable oral dosage forms include, but are not limited to, tablets, caplets, capsules (hard or soft gelatin), granules, powders, and chewable or effervescent formulations. In some embodiments, the oral dosage form includes one or more pharmaceutically or nutraceutically acceptable excipients, such as binders, disintegrants, fillers, lubricants, glidants, and coatings. In some embodiments, the supplement is encapsulated or compressed into a tablet using conventional techniques. In some embodiments, the capsule comprises a hard gelatin or cellulose-based shell. In some embodiments, the tablet is coated for enteric protection, taste masking, delayed release, or controlled release. In some embodiments, the solid oral dosage form is a tablet, caplet, or capsule. In some embodiments, the solid oral dosage form is a caplet with a coating that provides enteric protection.

In some embodiments, an oral composition of the disclosure is administered in a total daily dose of 1-30 tablets, capsules, or caplets, including all ranges and subranges therebetween. In some embodiments, an oral composition of the disclosure is administered in a total daily dose of 1-8 tablets, capsules, or caplets, including all ranges and subranges therebetween. In some embodiments, the oral composition is administered once daily, e.g., before breakfast. In some embodiments, the oral composition is administered twice daily, e.g., before breakfast and before dinner. In some embodiments, the oral composition is administered three times daily. In some embodiments, the oral composition is administered once every other day. In some embodiments, the oral composition is administered once every 2, 3, 4, 5, 6, 7, 8, 9, 10, 11, 12, 13, or 14 days. In some embodiments, each dose comprises 1-10 tablets, capsules, or caplets, including all ranges and subranges therebetween.

In some embodiments, a composition of the disclosure comprising an incretin agonist mimetic molecular cargo is administered in a manner analogous to existing incretin-based therapies, including but not limited to semaglutide, liraglutide, dulaglutide, and tirzepatide. In some embodiments, the dosing frequency may be adjusted to twice daily, as is common with short-acting GLP-1 receptor agonists such as exenatide (Byetta®), or to once weekly, as with long-acting agents such as dulaglutide (Trulicity®) or tirzepatide (Mounjaro®), depending on the pharmacokinetic profile of the fusion protein. Sustained-release formulations or encapsulation technologies may be employed to extend the half-life and reduce dosing frequency. In some embodiments, a composition of the disclosure is co-formulated with absorption enhancers, enteric coatings, or protease inhibitors to improve bioavailability, consistent with strategies used in the development of oral semaglutide. In some embodiments, the composition is administered in a fixed-dose combination with other antidiabetic agents, such as metformin or SGLT2 inhibitors.

For enteral application, in some embodiments, the pharmaceutical composition is in the form of tablets, caplets, or capsules having talc and/or carbohydrate carrier binder or the like. In some embodiments, the carrier is lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

As used herein, the term "single unit" encompasses one entity such as a single tablet and a single capsule. As used herein, the term "single unit dosage form" defines a dosage form which consists only of one unit which contains the effective amount of incretin mimetics. As used herein, the term "multiple unit dosage form" defines a dosage form which consists of more than one unit which contains the effective amount of incretin mimetics.

In some embodiments, the multiple unit dosage forms are based on subunits such as granules, pellets or minitablets. They are usually delivered in hard gelatin capsules or transformed into tablets. In another embodiment, the unit dosage form comprises the composition of the present invention in a single unit dosage form. The unit dosage form can comprise the composition of the present invention in a single unit dosage form selected from capsules and reconstituted powder. When the composition is a reconstituted powder suitable for being diluted before use, the powder can be a lyophilized powder. Any method known in the state of the art for the preparation of lyophilized powder for reconstitution is appropriate for the present invention.

A solid oral composition in form of capsules is advantageous when the treatment and/or prevention comprises administering incretin mimetics in an amount from about

EXAMPLES

Figure 1B:
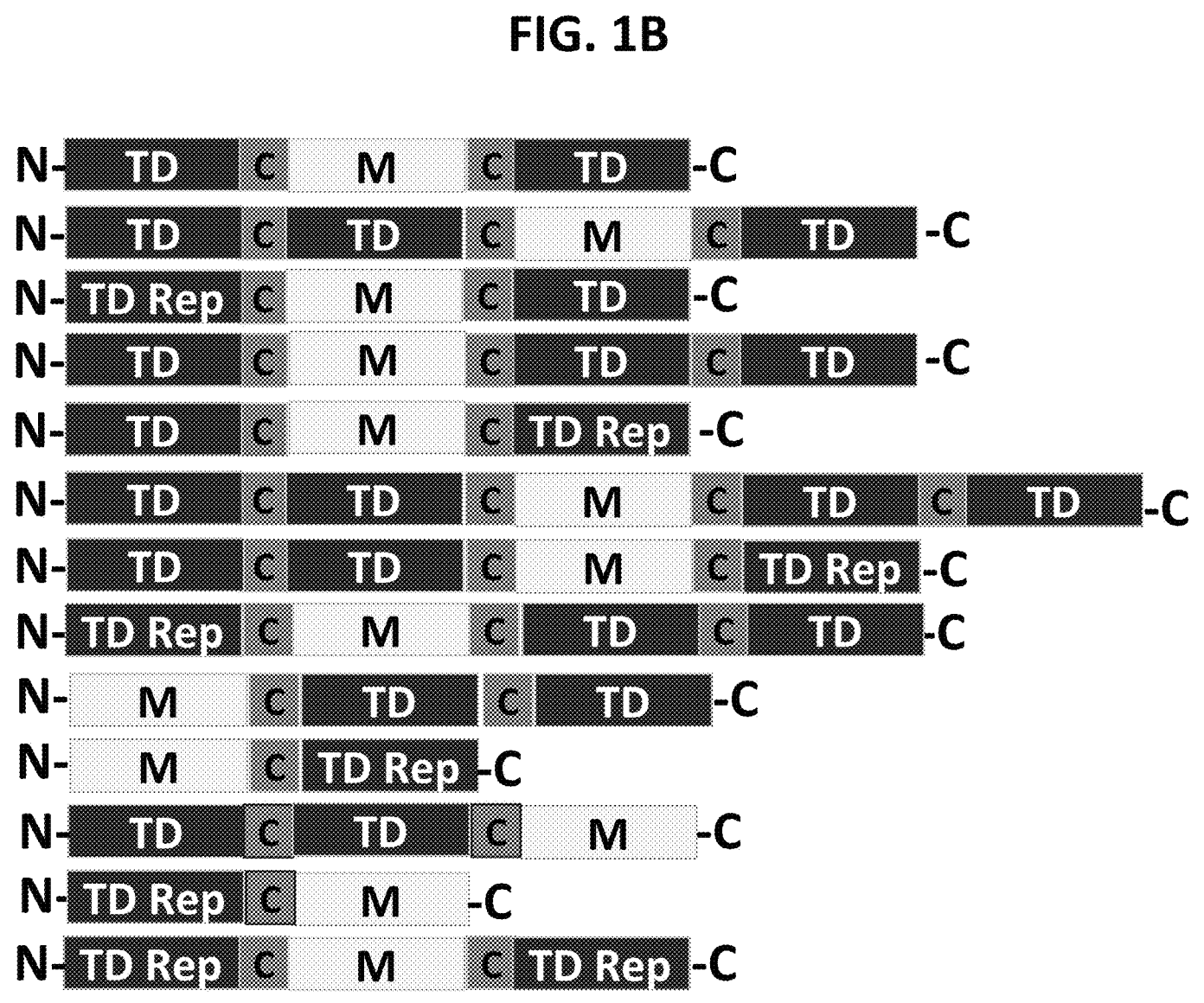
Figure 1D:
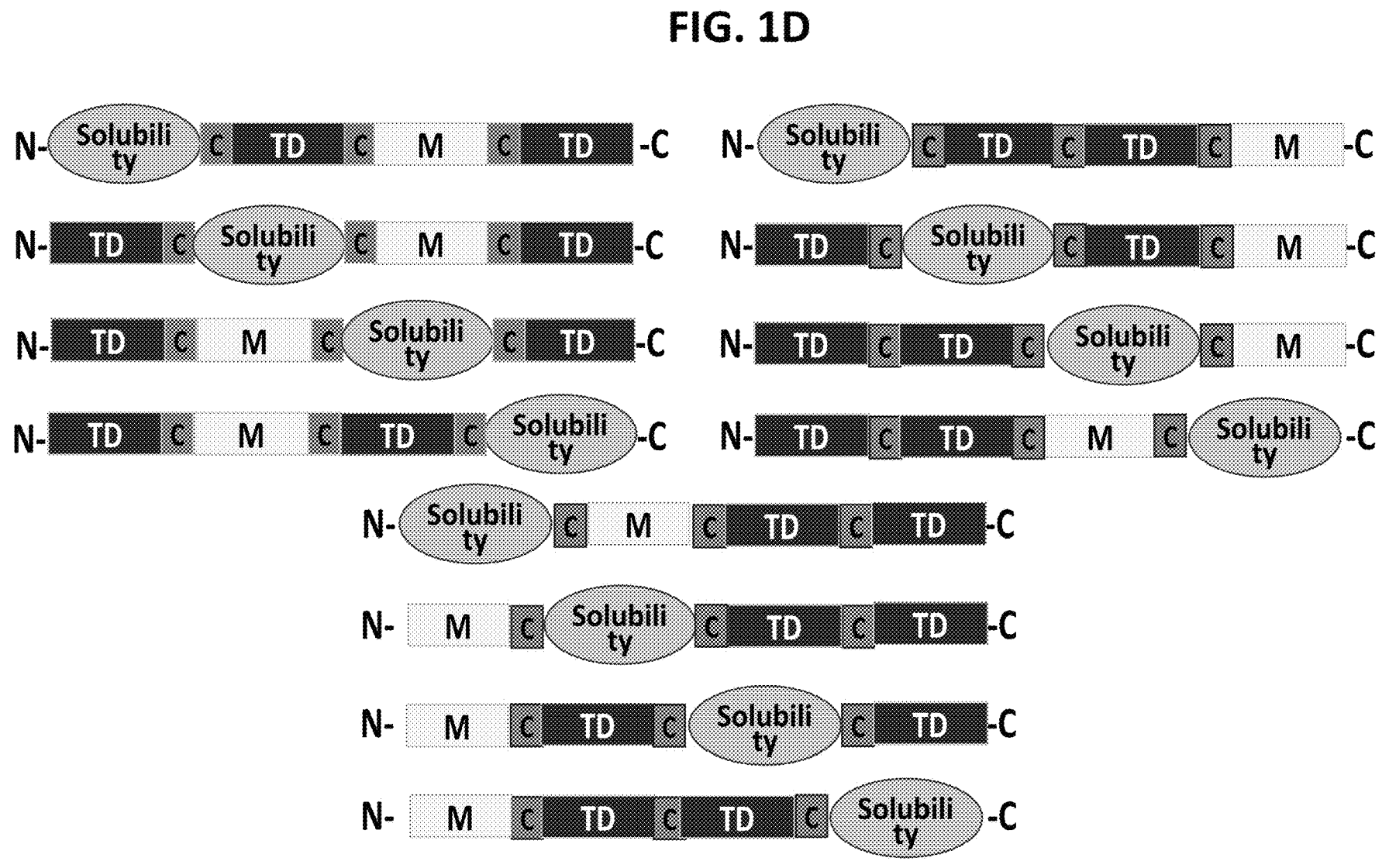

Example 1: Design of Exemplary Fusion Proteins and Biodelivery Platforms of the Disclosure The present inventors have developed novel fusion protein designs for delivery of molecular cargo. Numerous domain designs for embodiments of these fusion proteins are envisioned herein, e.g., in FIG. 1A-FIG. 1E. FIG. 1A, FIG. 1B, and FIG. 1C provide domain organization of the transduction domain ("TD"), molecular cargo domain ("M"), and protease cleavage sites ("C") comprised by fusion proteins of the disclosure in some embodiments. FIG. 1D provides domain organizations of fusion proteins of the disclosure comprising a solubility-enhancing domain ("Solubility") interspersed with TDs, Ms, and Cs.

C: The cleavage sites are sequences that can be cleaved by enzymes to process a full-length fusion protein into any biologically active sub-components or therapeutic moieties. In some embodiments, a fusion protein of the disclosure comprises any one of the domain architectures detailed herein without the annotated cleavage sites.

TD: The transduction domain can facilitate binding to intestinal epithelial cell or tissue or other specific organs to facilitate absorption across intestinal epithelium and/or localize the molecular cargo within the body. In some embodiments, each transduction domain in the complex is the same transduction domain. In some embodiments, each TD is a unique TD. In some embodiments, there are one or more TDs that are the same and one or more TDs that are unique. In some embodiments, any noted location of a TD in a domain organization provided herein contain one or more TDs in tandem with or without interspersed cleavage sites.

TD Rep: One or more transduction domains in tandem with or without interspersed cleavage sites.

M: The molecular cargo intended to be absorbed across the intestinal epithelium. In some embodiments, the molecular cargo is any molecular cargo, e.g., therapeutic peptide, disclosed herein. In some embodiments, multiple copies of a molecular cargo and/or different molecular cargos are integrated into the same complex in tandem with or without interspersed cleavage sites, or are placed interspaced between other defined domains.

[ ] Rep: Represents a sequence of domain elements that may be repeated in tandem.

Figure 1E:
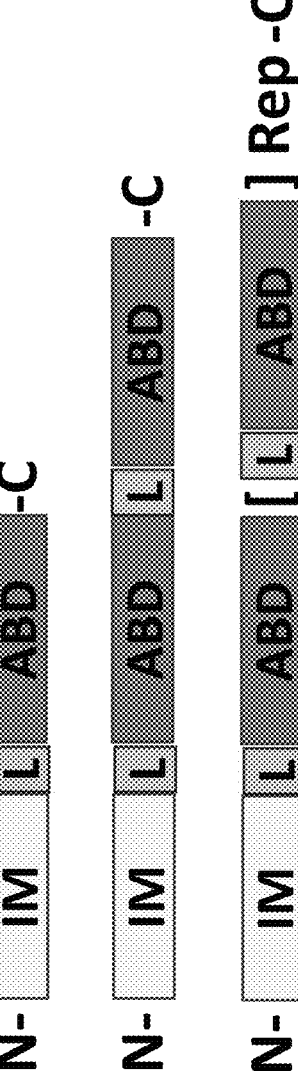
FIG. 1E provides some embodiments of incretin mimetic (IM) and albumin-binding domains (ABD) comprised by fusion proteins of the disclosure. Brackets and/or "Rep" represents a sequence of domain elements that may be repeated in tandem.

In the context of fusion proteins comprising incretin agonist mimetics herein, FIG. 1E provides some embodiments of incretin mimetic domains ("IM") and albumin-binding domains ("ABD") according to some embodiments of the disclosure. Also shown are linkers ("L"). In some embodiments, IM and ABD organization excludes one or more of the shown linkers.

ABD: Domain comprising an albumin-binding moiety. In some embodiments, an ABD extends the half-life of bound molecular cargo systemically.

Cleavage sites (C): Sites for cleavage by internal enzymes to process the full complex into any biologically active sub-components. May be either present or not present in any noted location.

Incretin Mimetic (IM): Any of the incretin agonists of the disclosure.

[ ] Rep: Represents a sequence of domain elements that may be repeated in tandem.

Figure 2C:
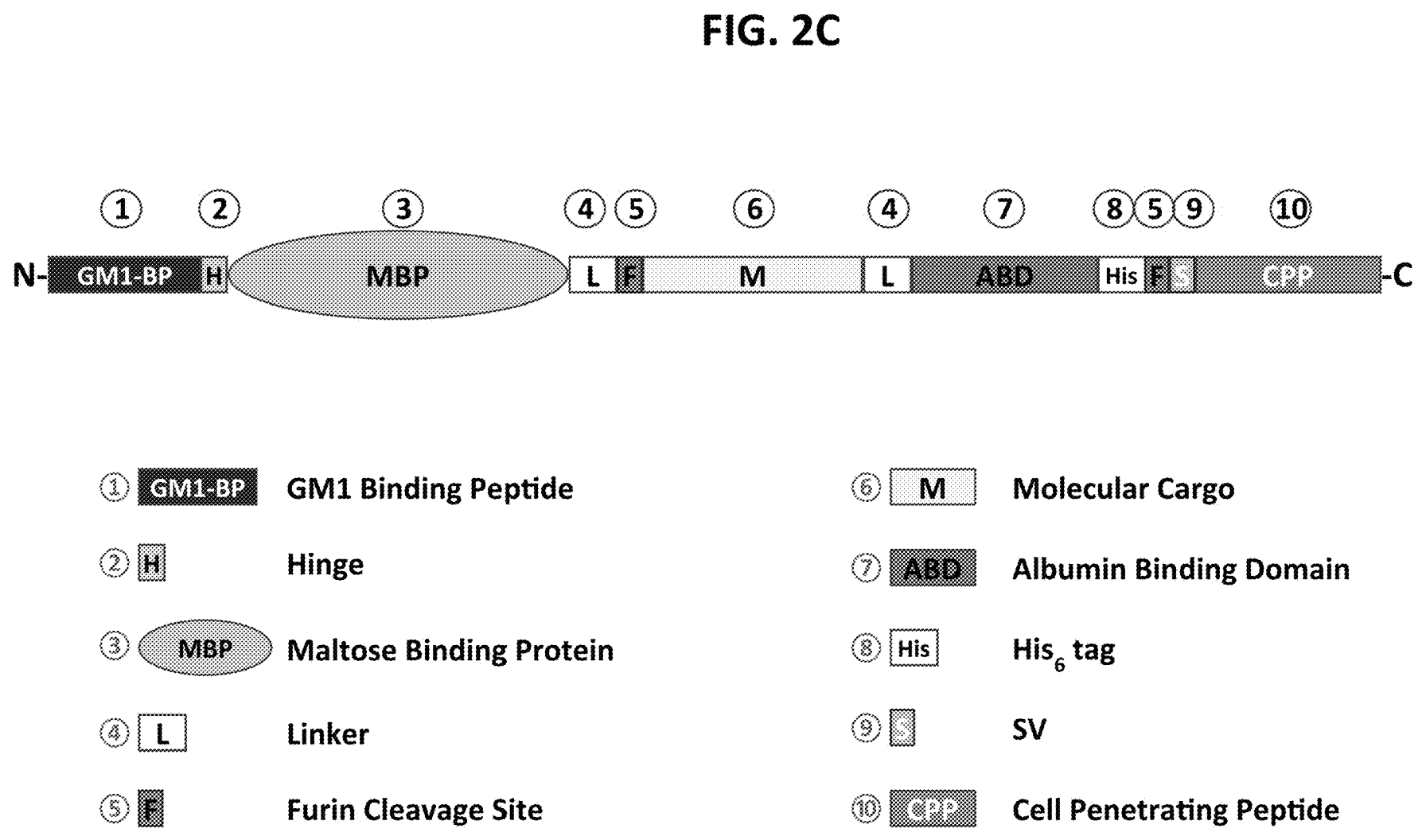
Figure 4A:
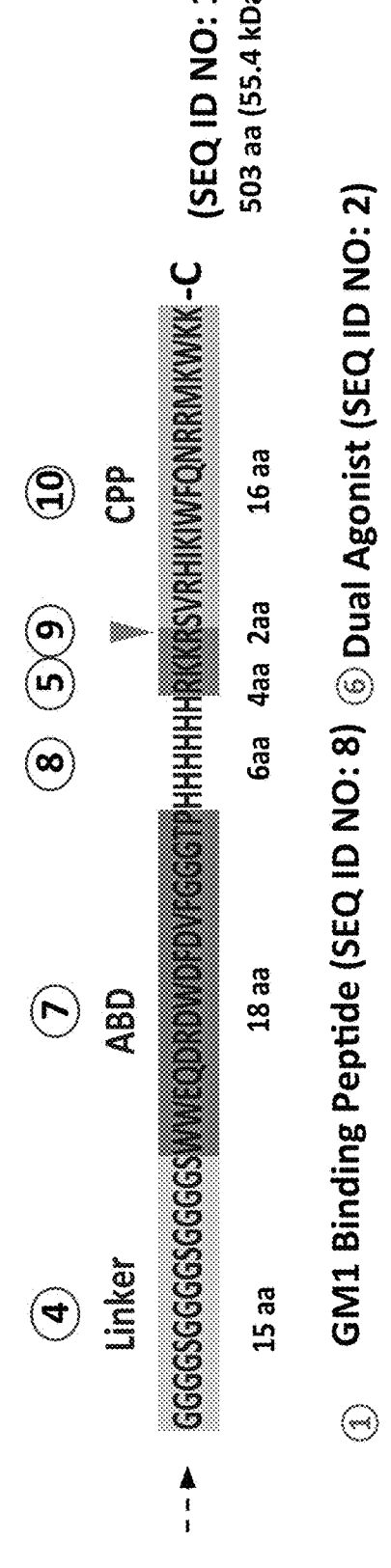
FIG. 4A provides a schematic of a fusion protein sequence (SEQ ID NO: 1) of the disclosure.

FIG. 2A-FIG. 2C provide schematics of exemplary fusion proteins of the disclosure. The fusion protein of FIG. 2A comprises from N to C terminus the following features: an "Absorption 1" domain (transduction domain) for promoting absorption by intestinal epithelial cells; a "Solubility" tag for promoting the solubility of the fusion protein; a first cleavage site, "C1"; a molecular cargo domain, "M"; a second cleavage site, "C2"; and an "Absorption 2" domain (transduction domain) that is a cell penetrating peptide for facilitating translocation of the fusion protein. FIG. 2B provides a fusion protein comprising the same features as the protein of FIG. 2A, but with an albumin binding domain, "ABD," for increasing fusion protein size, and reducing the rate of enzymatic degradation and renal clearance. FIG. 2C provides a fusion protein comprising from N to C terminus the following features: a GM1 binding peptide, a hinge, a maltose binding protein "MBP," a linker, a first furin cleavage site, a molecular cargo domain "M", an albumin binding domain, a 6×His tag, a second furin cleavage site, a serine and valine residue, and a cell penetrating peptide. FIG. 3 provides an overview of expression of an example fusion protein of the disclosure in two different host cell types. FIG. 4A provides a schematic overview of the fusion protein of SEQ ID NO: 1. Red triangles denote furin cut sites. FIG. 4B provides the full 503 amino acid length sequence of SEQ ID NO: 1. Residues 404-485 are the active, post-cleavage dual agonist protein excreted into the blood. FIG. 4C provides dual agonist sequences comprised by SEQ ID NO: 1.

Figure 5A:
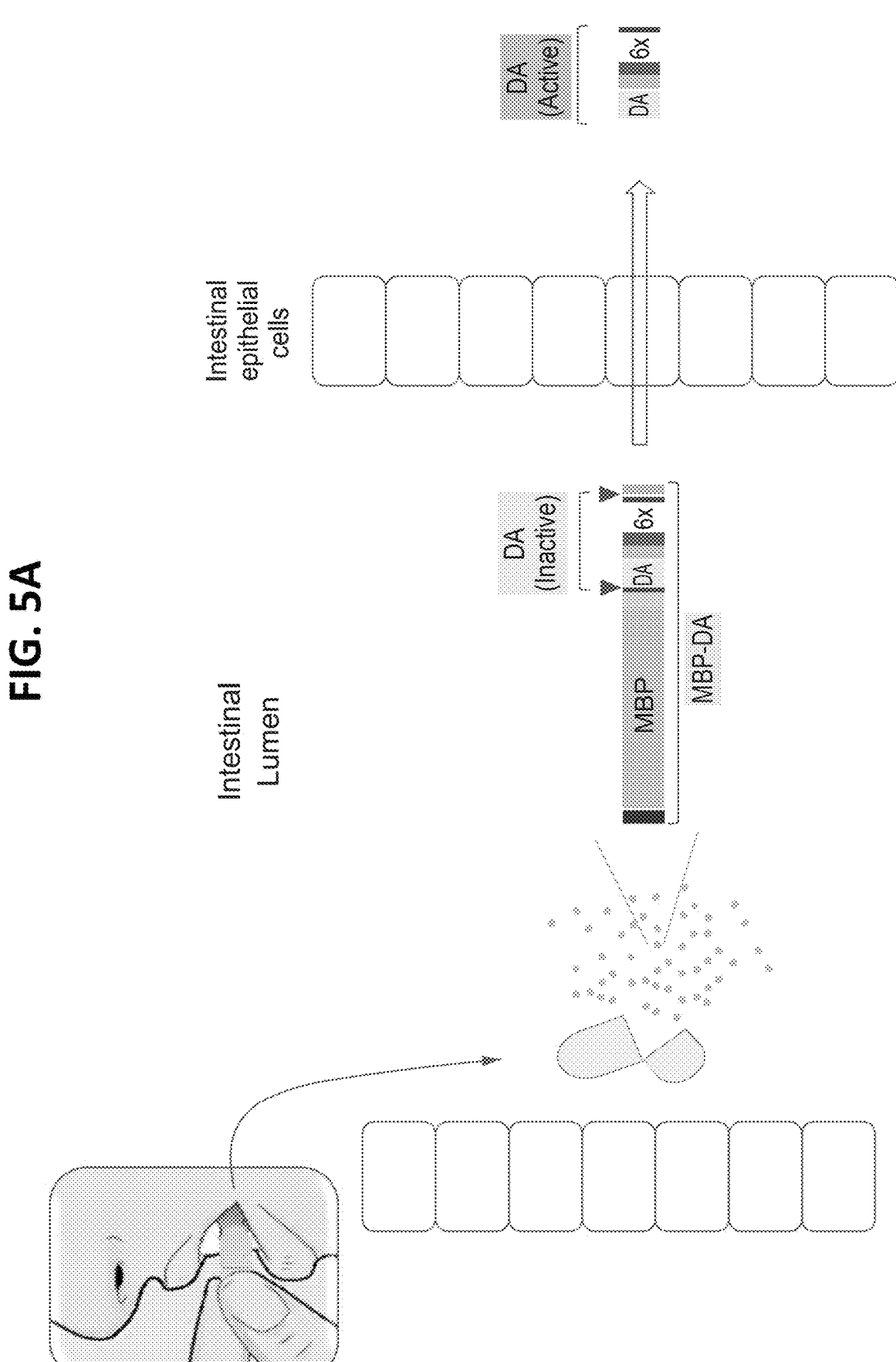
FIG. 5A provides a schematic of cleavage of a dual incretin agonist ("DA") into the blood stream after oral delivery using a fusion protein according to an embodiment of the present disclosure.
Figure 5B:
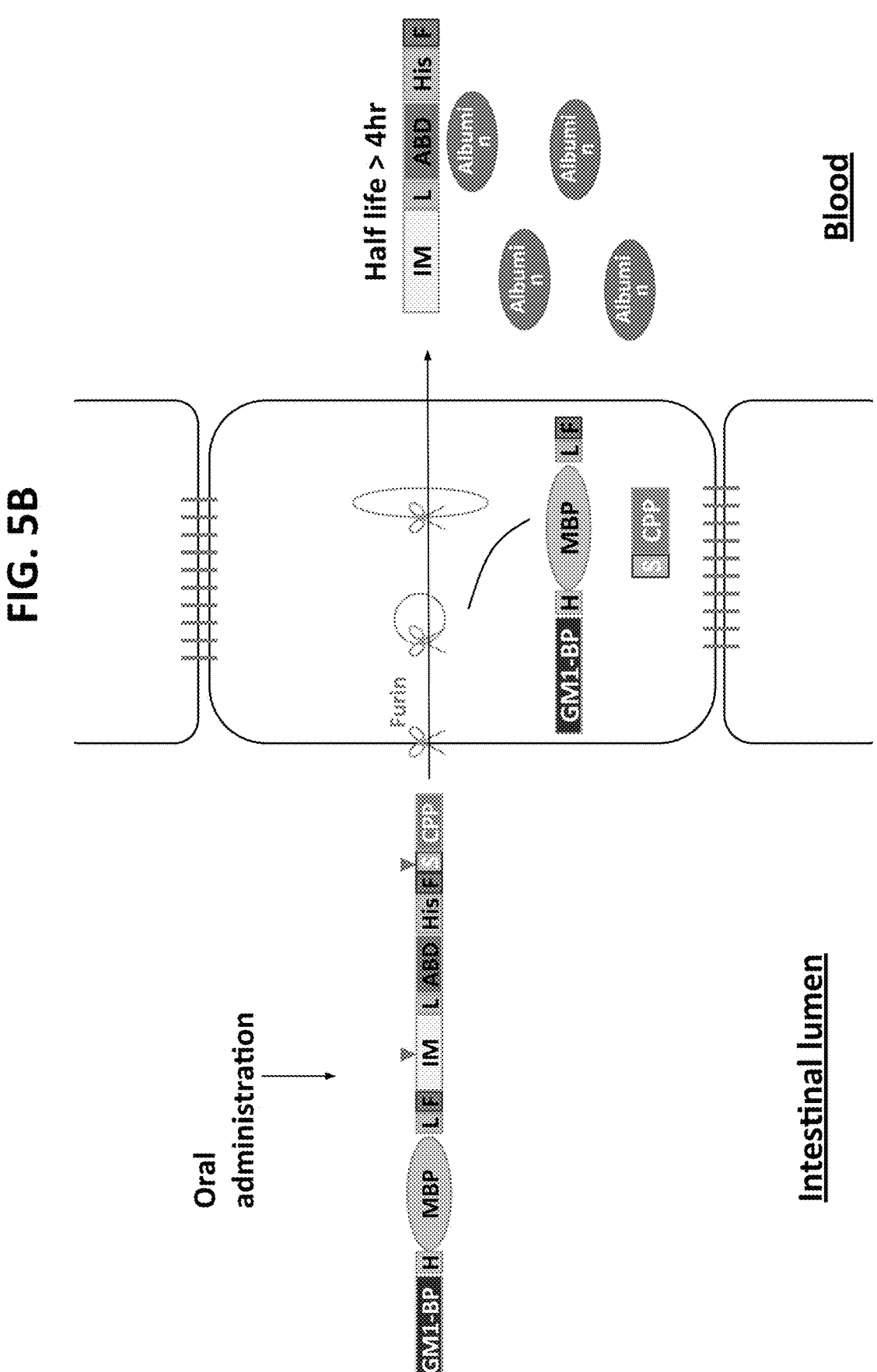
FIG. 5B shows furin cleavage of a fusion protein of the disclosure comprising an incretin mimetic ("IM") and the transfer from intestinal lumen to intestinal epithelial cell and onto the blood.
Figure 5C:
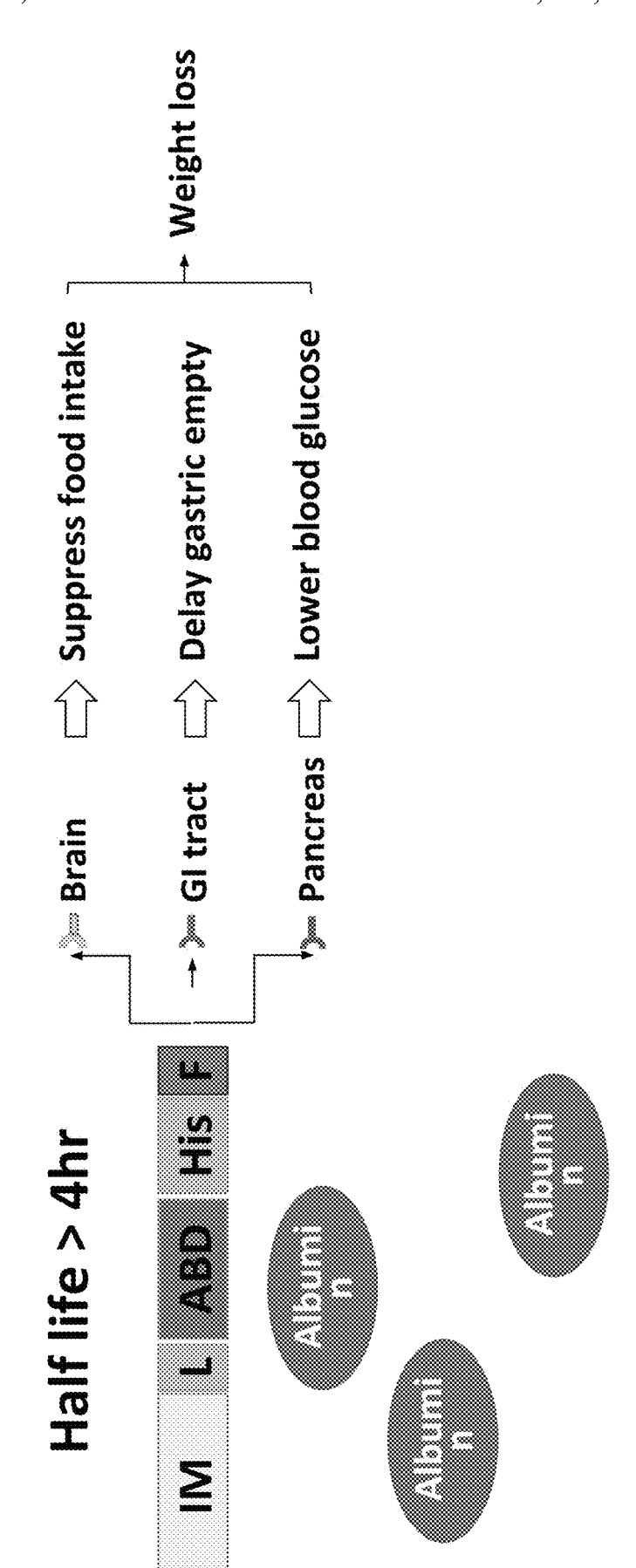
FIG. 5C shows downstream targets and effects of an incretin mimetic-comprising fusion protein post-cleavage.

FIG. 5A provides a non-limiting overview of a biodelivery platform of the disclosure, comprising a fusion protein ("MBP-DA") of the disclosure expressed in yeast. Yeast cells expressing the fusion protein are encapsulated into a tablet or pill (e.g., capsule), and ingested orally. Once ingested, the capsules break down and the fusion protein ("MBP-DA") expressed by the yeast cells is released into the intestinal lumen. Once the fusion protein crosses the intestinal epithelial cells, the fusion protein is cleaved and the active dual agonist therapeutic is released, "DA (Active)". FIG. 5B shows this biodelivery platform applied to a fusion protein having the domain architecture of FIG. 2C, demonstrating the action of furin, and the products of furin cleavage. The active DA therapeutic is released into the blood with a projected half life of over 4 hours. FIG. 5C outlines the downstream targets and functions of the active incretin agonist therapeutic. FIG. 6 provides an example manufacturing process for such a biodelivery platform.

Example 2: Multi-Incretin Agonists of the Disclosure Also Bind Glucagon and Albumin An in-vitro cAMP secondary messenger pathway binding assay was run to determine receptor activation and EC50 for a novel dual GLP-1/GIP receptor agonist (SEQ ID NO: 6) and to understand the impact of linking an albumin binding domain on the receptor engagement in the presence of human serum albumin. EC50 for GIP was found to be <0.00051 mM for the dual GLP-1/GIP receptor agonist in the absence of the albumin binding domain, and in the presence of the albumin binding domain EC50 was determined to be <0.00051 mM without human serum albumin and 0.0026 mM with human serum albumin, suggesting a decrease in GIP receptor binding affinity when the albumin binding domain is included and human serum albumin is in solution with the dual GLP-1/GIP receptor agonist. EC50 for GLP-1 was found to be 2.2 E-07 mM for the dual GLP-1/GIP receptor agonist in the absence of the albumin binding domain, and in the presence of the albumin binding domain EC50 was determined to be 3.7 E-07 mM without human serum albumin and 4.0 E-06 mM with human serum albumin, suggesting a decrease in GLP-1 receptor binding affinity when the albumin binding domain is included and human serum albumin is in solution with the dual GLP-1/GIP receptor agonist. Together these results demonstrate that the peptide has the ability to fully engage both GLP-1 and GIP at similar levels to native incretins even when bound to albumin and that the albumin binding domain does in fact enable binding to albumin in solution and as a result slightly decreases potency for GLP-1 and GIP when it is included.

Example 3: A Fusion Protein of the Disclosure Induces Weight Loss and Stabilizes Glucose Levels in a Preliminary Human Trial A preliminary experiment was performed on a human male adult (n=1) to demonstrate the effect of an active DA fusion protein on weight loss and glucose management. Oral capsules comprising yeast comprising the fusion protein of SEQ ID NO: 1 were manufactured according to FIG. 6. Each pill contained 320 mg of powdered dried yeast cells. This 320 mg included the following components: proteins (40-50%), carbohydrates (25-40%), lipids (5-8%), nucleic acids (5-10%), vitamins and minerals (5-8%), and other bioactives (1-2%), along with the MBP-DA (SEQ ID NO: 1). The dose of the active DA therapeutic (SEQ ID NO: 6) was 18.5 µg/capsule, and the dose of the full length, inactive MBP-DA was 120.3 µg/capsule.

An enteric capsule (~320 mg of yeast with ~18.5 µg of the DA active molecule per pill) was first taken on October 31st, followed by 1 capsule in the morning and evening on November 1st and November 2nd (2 capsules/day). Two capsules were taken in the morning and evening from November 3rd through November 18th (4 capsules/day).

Figure 7A:
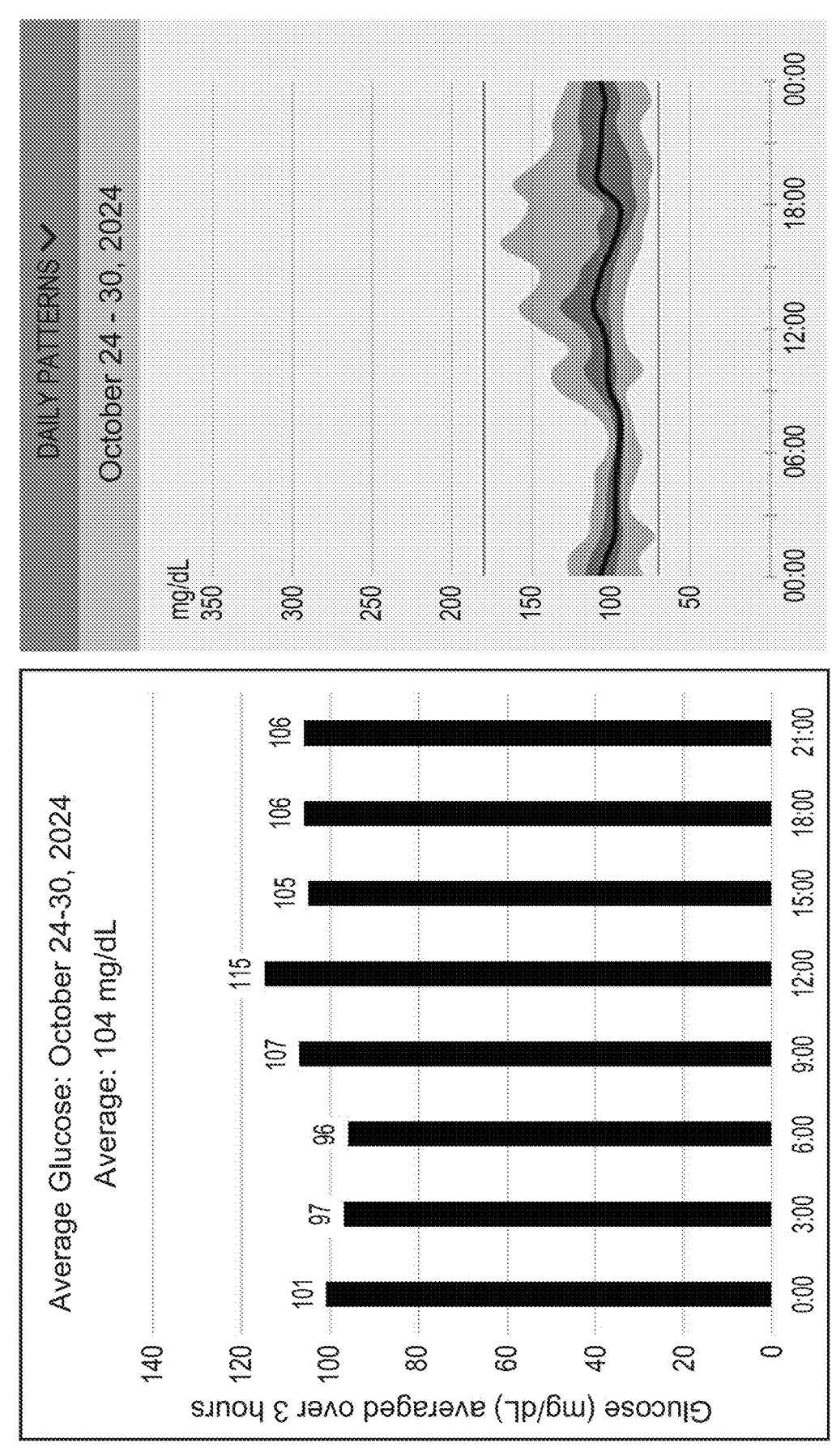
FIG. 7A-FIG. 7B show blood glucose levels measured with a CGM in the preliminary human experimental study of the Examples (n=1).
Figure 7B:
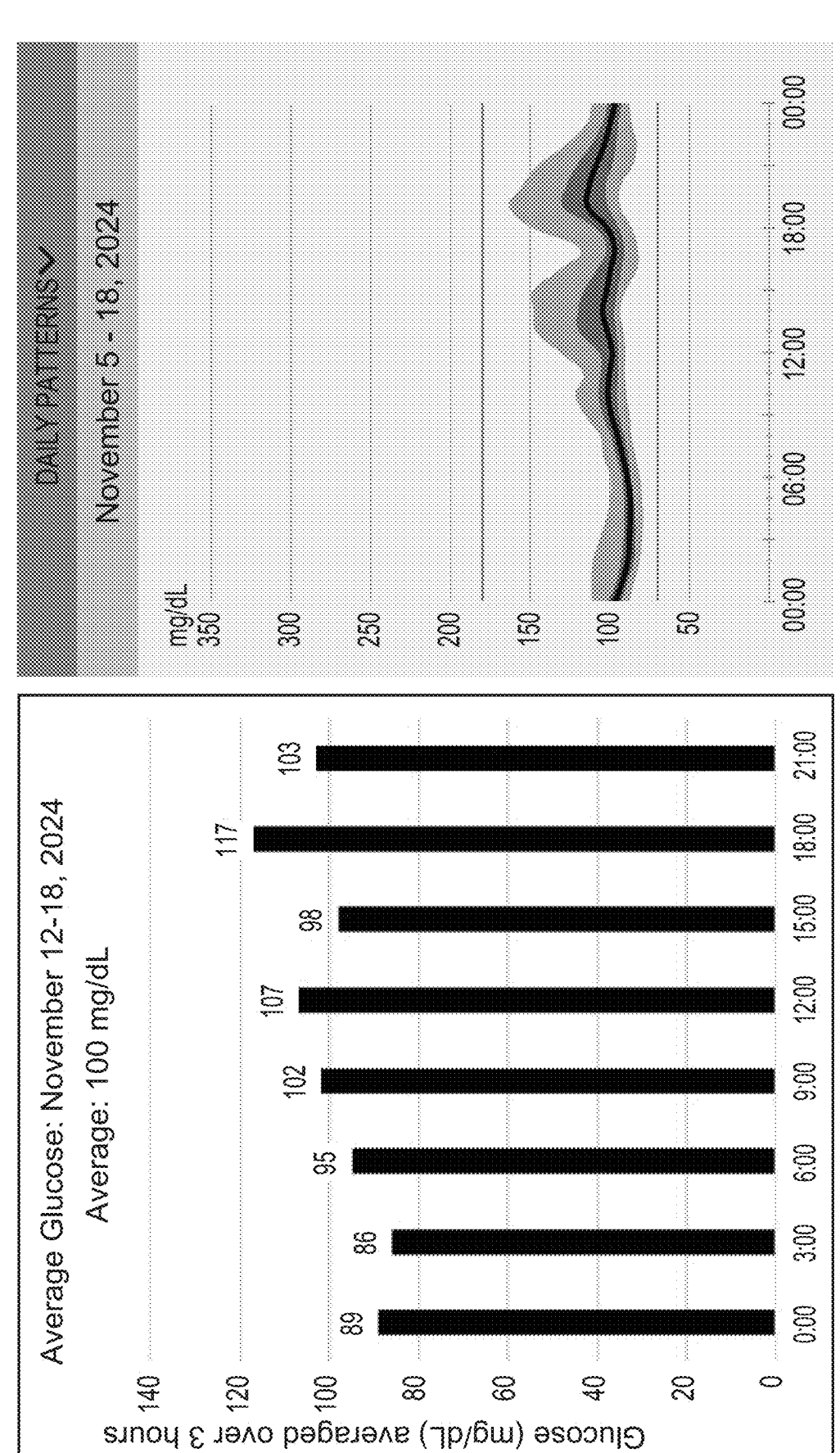

Blood glucose levels were measured via continuous glucose monitoring (CGM). Baseline glucose measurements are shown in FIG. 7A, while FIG. 7B shows glucose results at end of trial. At baseline, fasting blood glucose was between about 96 and 105 mg/dL; average glucose was 104 mg/dL; and GMI was 5.8% (~40 nmol/mol). Baseline measurements were consistent with a mildly pre-diabetic state. FIG. 7B shows reduced fluctuation in both average and daily glucose levels after two weeks of full dose treatment compared to baseline, as well as a decrease in fasting blood glucose levels. By the end of the trial, fasting blood glucose was between about 90 and 100 mg/dL; average glucose was between 99-100 mg/dL; and GMI was 5.7%. Measurements were no longer mildly pre-diabetic by the end of the two week trial.

Figure 8A:
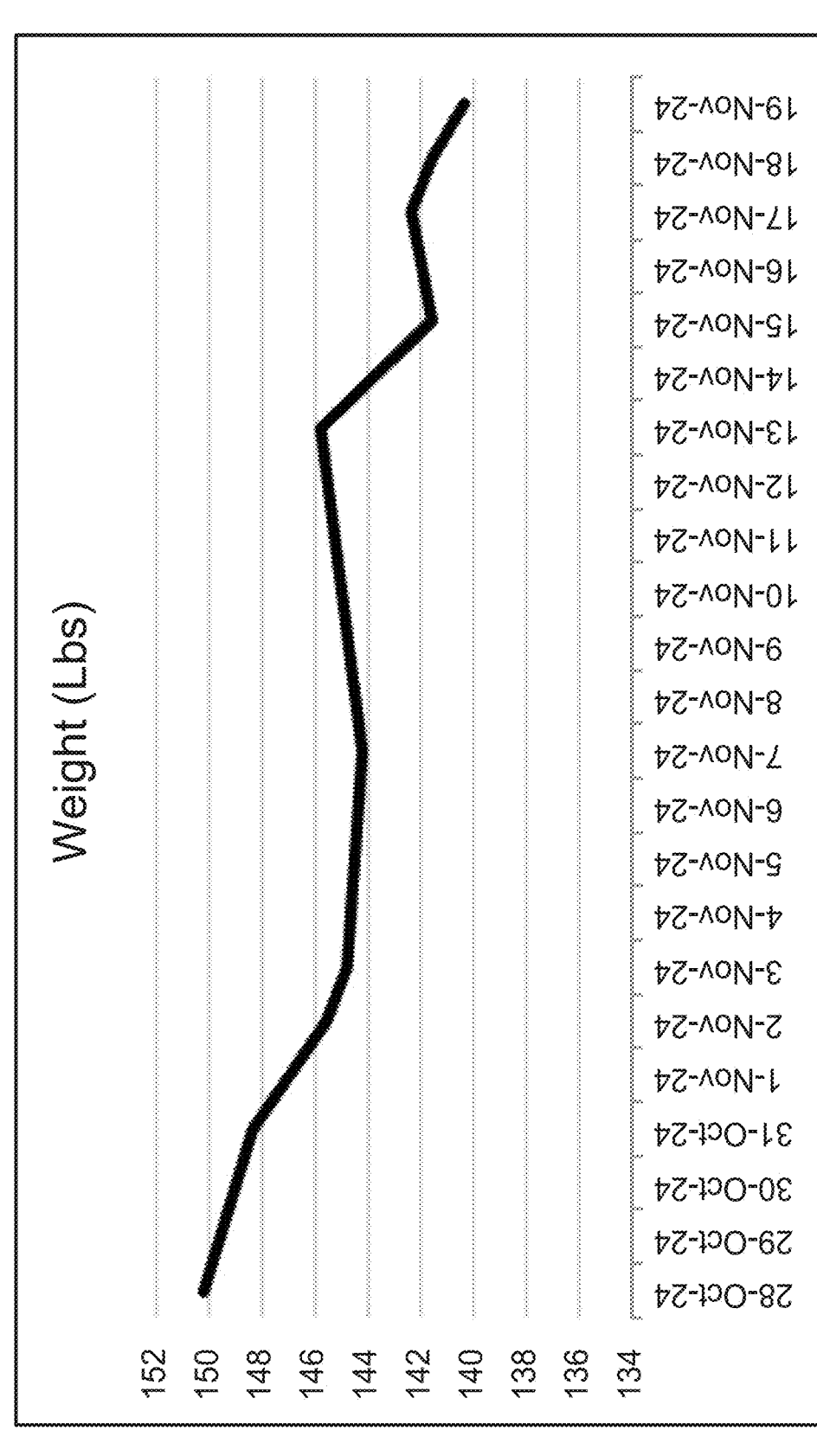
FIG. 8A shows weight measurements over the course of a preliminary human study of a fusion protein of the disclosure.
Figure 8B:
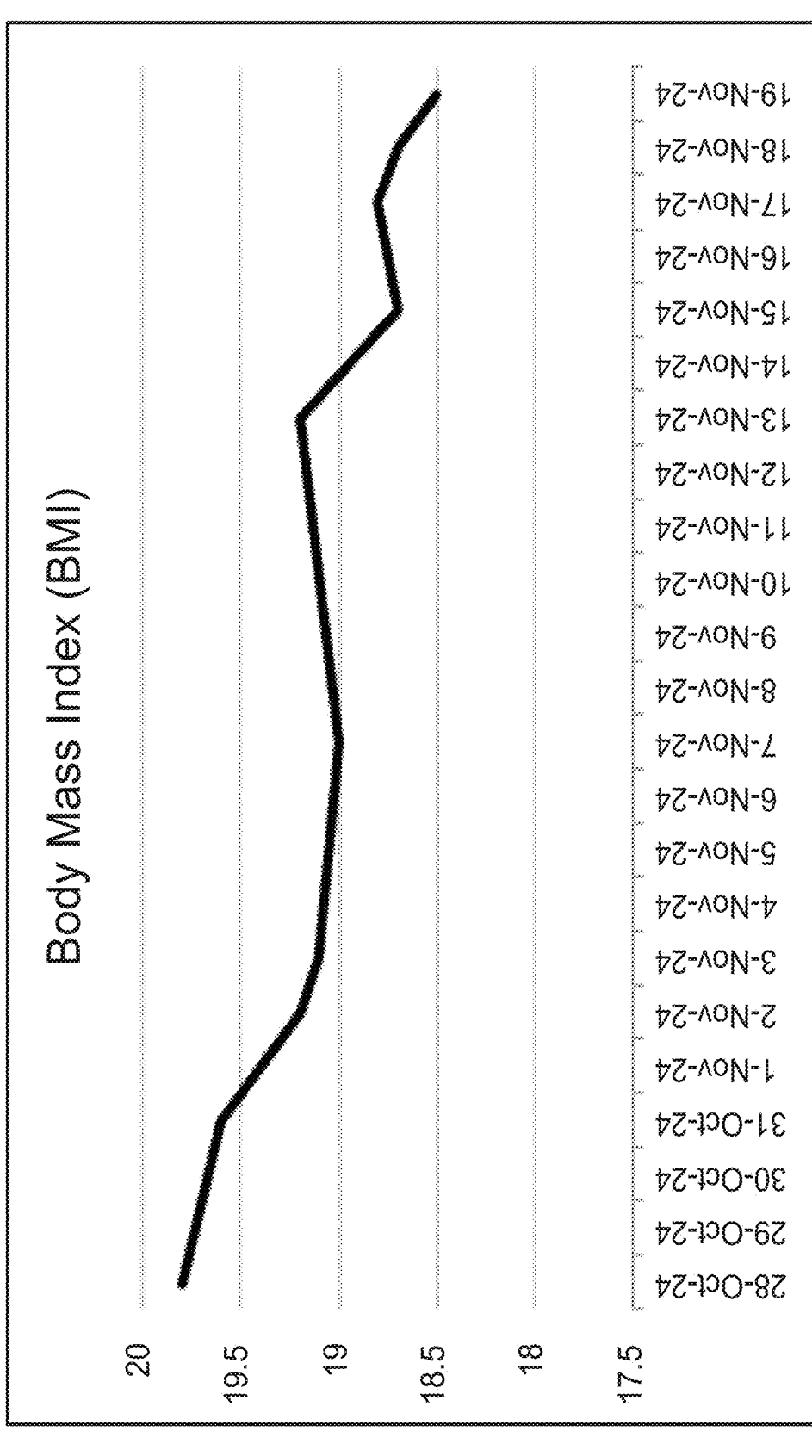
FIG. 8B shows BMI calculations over the course of the study.

Weight was also measured over the duration of the study (FIG. 8A), demonstrating a loss of about 10 lbs over the trial period from about 150 lbs to about 140 lbs. Calculation of BMI demonstrated a drop of over 1 pt, from about 19.7 to about 18.5 (FIG. 8B).

Example 4: New Dietary Ingredient *Saccharomyces cerevisiae* S288C EV1-Peptide Description of the New Dietary Ingredient This Example describes new dietary ingredient ("NDI") *Saccharomyces cerevisiae* S288C EV1-Peptide. *Saccharomyces cerevisiae* S288C EV1-Peptide has been formulated into a dietary supplement, to be marketed as "Evolv GLP-1 Biomimetic." Evolv GLP-1 Biomimetic is intended to help suppress appetite and maintain a healthy body weight. The proposed intake level is 200 mg (in the form of one capsule per day containing no more than 872 mcg of the novel metabolite).

This recombinant brewer's yeast strain produces a novel metabolite (EV1-Peptide) in the form of a peptide that is ultimately present in the dried yeast extract. The finished dietary ingredient is referred to herein as "*Saccharomyces cerevisiae* S288C EV1-Peptide," while the novel metabolite in isolation from the finished dietary ingredient is referred to as "EV1-Peptide," and the supplement containing the dietary ingredient is referred to as "Evolv GLP-1 Biomimetic." The prototype strain, having only one expression cassette for the EV1-Peptide, is referred to as "*Saccharomyces cerevisiae* S288C-I EV1-Peptide," in contrast to "*Saccharomyces cerevisiae* S288C EV1-Peptide," which is identical, except that it has three copies of the EV1-Peptide cassette for improved expression.

*Saccharomyces cerevisiae* S288C EV1-Peptide contains a novel chain of amino acids (protein), the protein is expressed in the yeast as a metabolite, and that metabolite is present in the dried yeast extract present at the end of the manufacturing process. That extract is intended to supplement the human diet.

Taxonomy

Table 3 shows the taxonomic classification of *Saccharomyces cerevisiae* S288C EV1-Peptide.

TABLE 3

Taxonomic Information on
*Saccharomyces cerevisiae* S288C EV1-Peptide.

| Taxonomic Level | Taxonomic Name |
| --- | --- |
| Domain | Eukarya |
| Kingdom | Fungi |
| Phylum | Ascomycota |
| Subphylum | Saccharomycotina |
| Class | Saccharomycetes |
| Order | Saccharomycetales |
| Family | Saccharomycetaceae |
| Genus | *Saccharomyces* |
| Species | *cerevisiae* |
| Strain | 288C |
| Variant | EV1-Peptide |

The *Saccharomyces cerevisiae* S288C EV1-Peptide is substantially equivalent to the host strain, with the sole difference being the insertion of triplicate copies of the gene expressing EV1-Peptide inserted in the *Saccharomyces cerevisiae* S288C, which enables the genetically modified organism to produce the novel EV1-Peptide. The resulting dried product contains non-viable lysed yeast cell extract and the novel EV1-Peptide.

Amino Acid Analysis

Table 4 demonstrates the number and relative percentage of each amino acid present in the EV1-Peptide. The EV1-Peptide includes only amino acids found in natural proteins and excludes any non-natural amino acids. The EV1-Peptide accumulates in the yeast strain as a metabolite, which is then released following cell lysis as a component of the yeast extract and dried to create the final NDI.

TABLE 4

Amino Acid Composition of EV1-Peptide.

| Amino Acid | Count | Percentage |
| --- | --- | --- |
| Ala (A) | 48 | 9.5% |
| Arg (R) | 14 | 2.8% |
| Asn (N) | 34 | 6.8% |
| Asp (D) | 30 | 6.0% |
| Cys (C) | 0 | 0.0% |
| Gln (Q) | 13 | 2.6% |
| Glu (E) | 29 | 5.8% |
| Gly (G) | 52 | 10.3% |
| His (H) | 11 | 2.2% |
| Ile (I) | 28 | 5.6% |
| Leu (L) | 36 | 7.2% |
| Lys (K) | 47 | 9.3% |
| Met (M) | 8 | 1.6% |
| Phe (F) | 20 | 4.0% |
| Pro (P) | 28 | 5.6% |
| Ser (S) | 25 | 5.0% |
| Thr (T) | 23 | 4.6% |
| Trp (W) | 15 | 3.0% |
| Tyr (Y) | 18 | 3.6% |
| Val (V) | 24 | 4.8% |
| Sum: | 503 | 100% |

*Saccharomyces cerevisiae* S288C EV1-Peptide Supplements the Diet

*Saccharomyces cerevisiae* S288C EV1-Peptide is derived from a modified *Saccharomyces cerevisiae*. *S. cerevisiae* acts as a source of amino acids, B vitamins and nutrients (Kour et al. 2023, Jach et al. 2022). Similarly, *Saccharomyces cerevisiae* S288C EV1-Peptide is a yeast extract, which is a substance that can be added to dietary supplements as a combination of amino acids and can be used as a dietary substance to supplement the diet by increasing the total dietary intake.

The new EV-1 peptide is intended to reduce appetite by activating incretin receptors when delivered orally. The amino acid sequence in FIG. 5B corresponds to the novel chain of amino acids. Positions 1-403 and positions 486-503 represent carrier amino acids that are cleaved off during digestion, whereas positions 404-485 describe the amino acids contained in *Saccharomyces cerevisiae* S288C EV1-Peptide that are functional in the finished dietary supplement, are not cleaved off or destroyed during digestion, and supplement the diet.

One capsule of the dietary supplement contains 200 mg dried yeast extract. Each mg of yeast extract contains a mean value of about 4.07 mcg and a general upper value of about 4.36 mcg EV1-Peptide. Thus, one capsule delivers an average of about 814 mcg and a general upper value of about 872 mcg EV1-Peptide.

Example 5: Manufacturing and Batch Testing of
*Saccharomyces cerevisiae* S288C EV1-Peptide Manufacturing Production of the dietary ingredient begins with a yeast strain. The yeast strain serves as the foundational raw material. The growth media contains the components listed in Table 5.

TABLE 5

| Media Composition | |
| --- | --- |
| Component | Composition (%) |
| Water | 97.18 |
| Cane sugar | 1.99 |
| Yeast extract | 0.63 |
| Magnesium sulfate | 0.07 |
| Calcium sulfate | 0.05 |
| Potassium chloride | 0.04 |
| Diammonium phosphate | 0.04 |
| Zinc sulfate | 0.002 |

Figure 9:
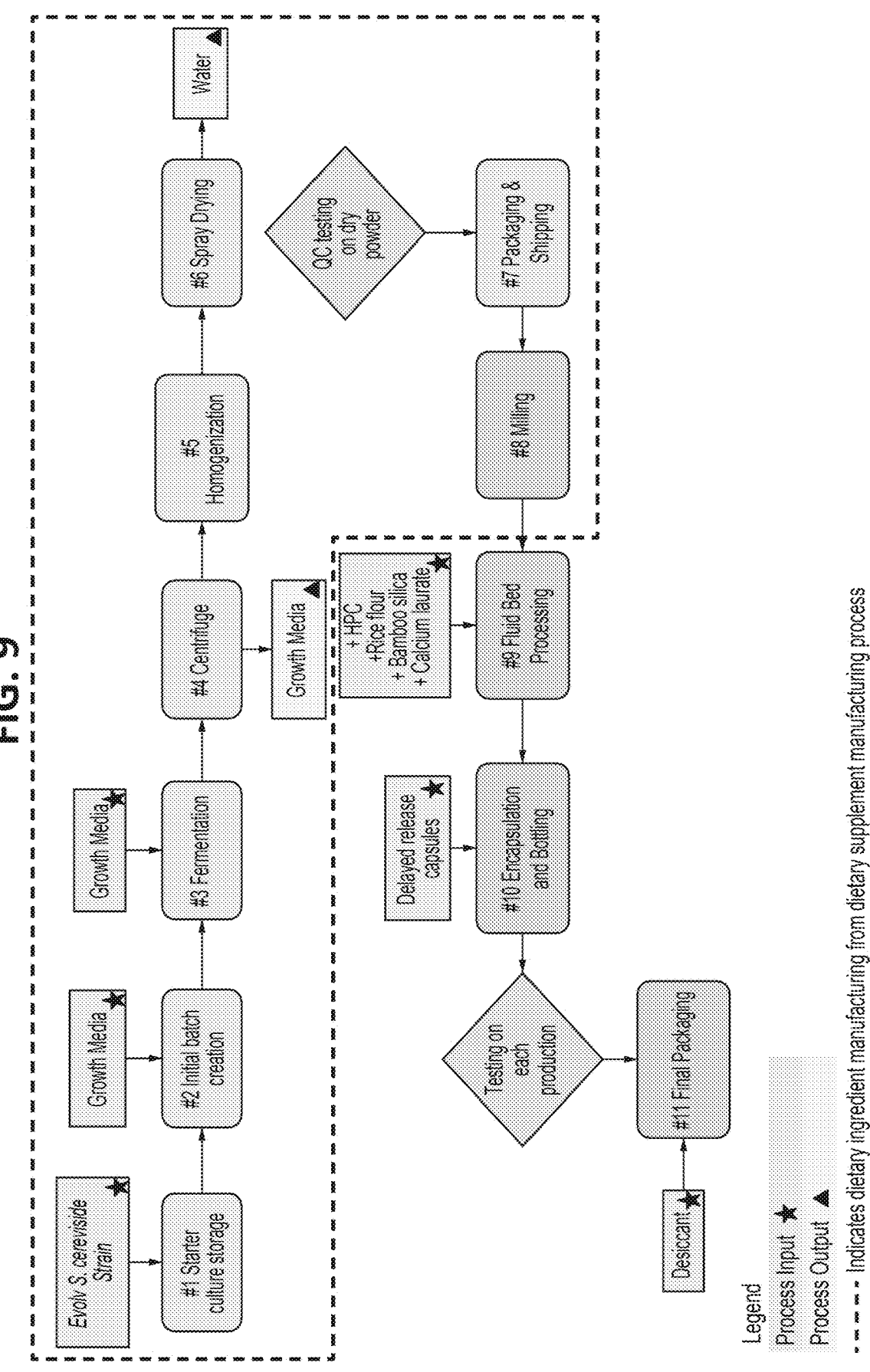
FIG. 9 shows a schematic for the manufacturing of *Saccharomyces cerevisiae* S288C EV1-Peptide.

A schematic for the manufacturing process is presented in FIG. 9. The dashed line encloses the production steps in the manufacture of the dietary ingredient from the manufacturing of the dietary supplement.

The manufacturing process was conducted as follows: The yeast was cultivated in a controlled environment as the inoculum for large-scale fermentation (step 1). During fermentation, the yeast strain was combined with a growth media primarily consisting of glucose and water (step 2, full composition listed in Table 5). This nutrient-rich mixture supported rapid yeast cell proliferation. Aeration was continuously applied to optimize oxygen availability, enhancing cellular metabolism and ensuring uniform growth. As the fermentation progresses, additional media was incrementally introduced until the yeast population reached a critical mass. At this stage, media supplementation ceased, leaving the yeast cells dormant. The result was a combination of a concentrated yeast slurry and the residual media mixture (step 3). The slurry was then separated from the residual media utilizing a centrifuge, yielding a yeast slurry composed of approximately 13-15% solids (step 4). Following centrifugation, the yeast slurry was subjected to multiple sequential passes through a high-pressure homogenization system, where it experienced controlled mechanical shear and pressure forces that enhance uniformity and achieve cell lysis (step 5). This process was a kill-step, as it effectively disrupted any remaining yeast cell aggregates, ensuring a consistent particle size distribution and releasing the metabolites present within the yeast as an extract.

The spray-drying process was conducted under controlled thermal conditions, with an inlet temperature of 180° C. and an outlet temperature of 80° C. (step 6). This dehydration step reduced moisture content while preserving the structural integrity and functional properties of the final powdered ingredient. Comprehensive quality control testing was then completed on the dietary ingredient, and a Certificate of Analysis (COA) was issued for each batch that successfully passed through rigorous testing standards. The ingredient was then shipped via sealed bags to a GMP-certified co-manufacturer (step 7), where it underwent milling (step 8) and blending (step 9).

Finally, the powder was encapsulated in vegan capsules designed for delayed release in the small intestines. Capsules were bottled along with a desiccant to maintain dryness (step 10). Bottles were heat-sealed for integrity and prepared for distribution. Prior to distribution, samples from each production lot underwent analytical testing, confirming the specifications outlined in Table 6 and maintaining the intended dosing. Upon verification, the finished goods were approved for final packaging and distribution (step 11).

Product Specifications for *Saccharomyces cerevisiae* S288C EV1-Peptide

The specifications for *Saccharomyces cerevisiae* S288C EV1-Peptide are listed in Table 6.

TABLE 6

| *Saccharomyces cerevisiae* S288C EV1-Peptide Specifications. | | |
|---|---|---|
| Tests | Specifications | Method |
| Principal Components | | |
| EV1-Peptide | <4.36 mg/g | Western blot and densitometry assay |
| Physical Characteristics | | |
| Appearance | Light tan powder | Visual inspection |
| Moisture content | <6% | Loss on Drying (LOD) |
| Microbial Testing | | |
| Total aerobic microbial count | ≤10,000 CFU/g | AOAC 966.23 |
| Total mold count | ≤1,000 CFU/g | FDA-BAM, 7th ed. |
| *E. coli* | <3/g | AOAC 966.24 |
| *Salmonella* species | Negative/25 g | AOAC RI 100201 |
| *S. aureus* | <10/g | AOAC 975.55 |

Notes:
cfu = colony forming units;
mg = milligrams;
g = grams

Batch Analysis

Batch data are presented below for three lots of *Saccharomyces cerevisiae* S288C EV1-Peptide (Table 7), which data are in accordance with the specifications provided in Table 6.

TABLE 7

| | | Production Batch | | | |
|---|---|---|---|---|---|
| Parameter | Specification | Batch #1 | Batch #2 | Batch #3 | Method |
| Principal Components | | | | | |
| EV1-Peptide | <4.36 mg/g | 4.14 | 4.27 | 3.79 | Western blot and densitometry assay |
| Physical Characteristics | | | | | |
| Appearance | Light tan powder | Light tan powder | Light tan powder | Light tan powder | Visual inspection |
| Moisture content | <6% | <6% | <6% | <6% | Loss on Drying (LOD) |
| Microbial Testing | | | | | |
| Total aerobic microbial count | ≤10,000 CFU/g | <LOQ | <LOQ | <LOQ | AOAC 966.23 |
| Total mold count | ≤1,000 CFU/g | <LOQ | <LOQ | <LOQ | FDA-BAM, 7th ed. |
| *E. coli* | <3/g | <LOQ | <LOQ | <LOQ | AOAC 966.24 |
| *Salmonella* species | Absent in 10 mg | Negative | Negative | Negative | AOAC RI 100201 |
| *S. aureus* | Absent in 10 mg | <LOQ | <LOQ | <LOQ | AOAC 975.55 |

Notes:
cfu = colony forming units;
mg = milligrams;
g = grams

Example 6: In Silico Assays do not Identify Allergenic/Toxigenic Attributes of EV1-Peptide To evaluate the allergenicity potential of the novel sequences present in *Saccharomyces cerevisiae* S288C EV1-Peptide, a FASTA search was run for EV1-Peptide's amino acid sequence against known allergenic sequences in the University of Nebraska Allergen Online Database (allergenonline.org/databasehelp.shtml). This comparison was performed to identify proteins that may share immunologic or allergic cross-reactivity with the novel protein. Matches with E-values larger than 1e-7 are not likely to be relevant, while matches with E-values smaller than 1e-30 are much more likely to be cross-reactive in at least some allergic individuals (Hileman, 2002). Using an E-value cutoff of 1e-7, no significant matches were found against the novel EV1-Peptide sequence.

Next, parameters utilized by the Codex *Alimentarius* Commission (2003) were applied to search for additional cross-reactive allergenic possibilities. Codex *Alimentarius* recommends a bioinformatics search using a FASTA or a BLASTP algorithm, and suggests that matches of at least 35% identity over segments of at least 80 amino acids may indicate the possibility of cross-reactivity. Leveraging these parameters in the Allergen Online Database also provides a result of no significant matches against the novel protein (Appendix 4.3.2). Neither computational assay identified toxic or allergenic proteins or cross-reactive potential within the novel EV1-Peptide sequence, nor proteins implicated in the formation of undesirable compounds.

Example 7: Subacute Toxicology Study of *Saccharomyces cerevisiae* S288C-I EV1-Peptide

Materials and Methods

The subacute 14-day oral toxicity of *Saccharomyces cerevisiae* S288C-I EV1-Peptide was examined in male Crl:CD Sprague Dawley rats in a research grade study, conducted following IACUC Animal Use Protocol authorization. Euthanasia and tissue/blood collections were split into 2 days to accommodate necropsy and collection time.

Animals were provided with chlorinated reverse-osmosis treated water and standard irradiated rodent diet (LabDiet, 5002) ad libitum. Animals were maintained in Allentown individually ventilated cage racks. Temperature and humidity were monitored daily throughout the facility. This includes animal housing rooms, inventory spaces, and support/operations rooms. Humidity was maintained throughout the facility between 30-70% relative humidity and followed the recommendations below from the Guide for the Care and Use of Laboratory Animals (National Research Council of the National Academies 2011). Lighting in animal housing rooms was controlled by an automatic timer which was set to a 12:12 hour light: dark schedule. Positive reinforcement training (PRT) was provided to animals for 3 weeks prior to dosing to acclimate them to staff and routine behaviors/tasks anticipated during the study. These behaviors were rewarded with food rewards such as certified treats or other interactions that the animal considered positive. Example behaviors include general handling, weight measurements, restraint, oral dosing, or blood collection.

Following PRT, four (4) groups of three (3) male rats were administered a fixed daily dose of the vehicle control Phosphate Buffer Solution (PBS), 0.3, 0.15, and 0.03 grams of dried yeast extract (*Saccharomyces cerevisiae* S288C-I EV1-Peptide, the prototype strain) per animal by oral gavage for 14 days. The highest dose was selected to be representative of dose levels that would deliver greater than 100× the amount of EV1-Peptide anticipated for use as a constituent of the dietary ingredient (dried yeast extract) for human use. Adjusting intake estimates by body weight, the approximate maximum dose levels of the dried yeast extract ranged from 1,000 mg/kg bw/day to 750 mg/kg bw/day, decreasing as the animals gained weight. The corresponding dose levels of EV1-Peptide were calculated to be 1290 mcg/kw bw/day to 968 mcg/kw bw/day, also decreasing slightly as the animals gained weight.

Animals were weighed on days −21, −14, −7, 1 (start of treatment), 8, and 15.

Results

All animals gained weight throughout the duration of the study. The body weights during the in-life phase of the study increased from ~300 g/animal to ~400 g/animal (see FIG. 10). There was no statistically significant difference in average weight between the different test groups and control group. No abnormal or adverse observations or unscheduled deaths were noted throughout the study, following daily observations. No blood or tissues were collected at the completion of the study.

Example 8: Subchronic Toxicology Study of *Saccharomyces cerevisiae* S288C-I EV1-Peptide

Materials and Methods

The subchronic 90-day oral toxicity of *Saccharomyces cerevisiae* S288C-I EV1-Peptide (prototype) was examined in male and female Crl:CD Sprague Dawley rats in a research grade study. The study design was selected to test the maximum tolerated dose (MTD) while assessing general tolerability and potential adverse effects. The selected dose levels and duration align with established guidelines for toxicity evaluation, to assess both acute and subchronic exposure.

Eight-week-old male and female Sprague Dawley (Charles River: 001) rats were obtained from Charles River, North Carolina. The rats were housed individually in ventilated care racks.

Animals were provided with chlorinated reverse-osmosis treated water and standard irradiated rodent diet (LabDiet, 5002) ad libitum. Positive reinforcement training (PRT) was provided to animals for 3 weeks prior to dosing to acclimate them to staff and routine behaviors/tasks anticipated during the study. These behaviors were rewarded with food rewards such as certified treats or other interactions that the animal considered positive. Example behaviors include general handling, weight measurements, restraint, oral dosing, or blood collection.

Following PRT, animals were assigned to treatment groups determined by body weight prior to dosing. Four (4) groups of three (3) male and three (3) female rats were administered a fixed daily dose of the vehicle control Phosphate Buffered Saline (PBS), 0.03, 0.15, or 0.3 grams of the dried yeast extract per day by oral gavage for 90 consecutive days.

Body weights of the rats were measured at intake and weekly throughout the study. Cage-side observations were conducted daily, and food consumption was measured weekly. Blood was collected via the tail vein on day 44 of the study and via cardiac puncture at euthanasia.

Terminal serum samples were assessed for the following clinical chemistry end-points: albumin (ALB), globulin (GLOB), alkaline phosphatase (ALP), alanine aminotransferase (ALT), aspartate aminotransferase (AST), total bilirubin, conjugated bilirubin, unconjugated bilirubin, calcium (Ca), sodium (Na), potassium (K), chloride (Cl), cholesterol, creatinine kinase (CK), glucose (GLU), phosphorous (PHOS) and total protein (TP). Following termination, standard necropsy was performed on all animals, measuring whole body weight, and gross observations and weights of the heart, lung, brain, liver, kidneys, spleen, gastrointestinal tract and genitourinary tract were documented. Any abnormalities were photographed and fixed in formalin.

The pancreas was specifically selected for histopathology evaluation for all 24 animals. Unstained slides were deparaffinized in xylene, hydrated through graded alcohols up to water, and put in Carazzi's hematoxylin. The slides were then washed in tap water, put in one change 95% ethanol, and then put in eosin-phloxine solution and run through graded alcohols to xylene. After xylene, the stained slides were cover slipped using permount as the mounting media. Slides were scored by a board-certified veterinary pathologist. Animals found dead or that required euthanasia were not further assessed.

One female in the mid-dose group (0.15 g) was found dead on day 39 of dosing, but no treatment-related clinical signs of toxicity were reported and the death was found to be due to the action of oral gavage, not due to the test substance.

Results

Figures 11A, 11B:
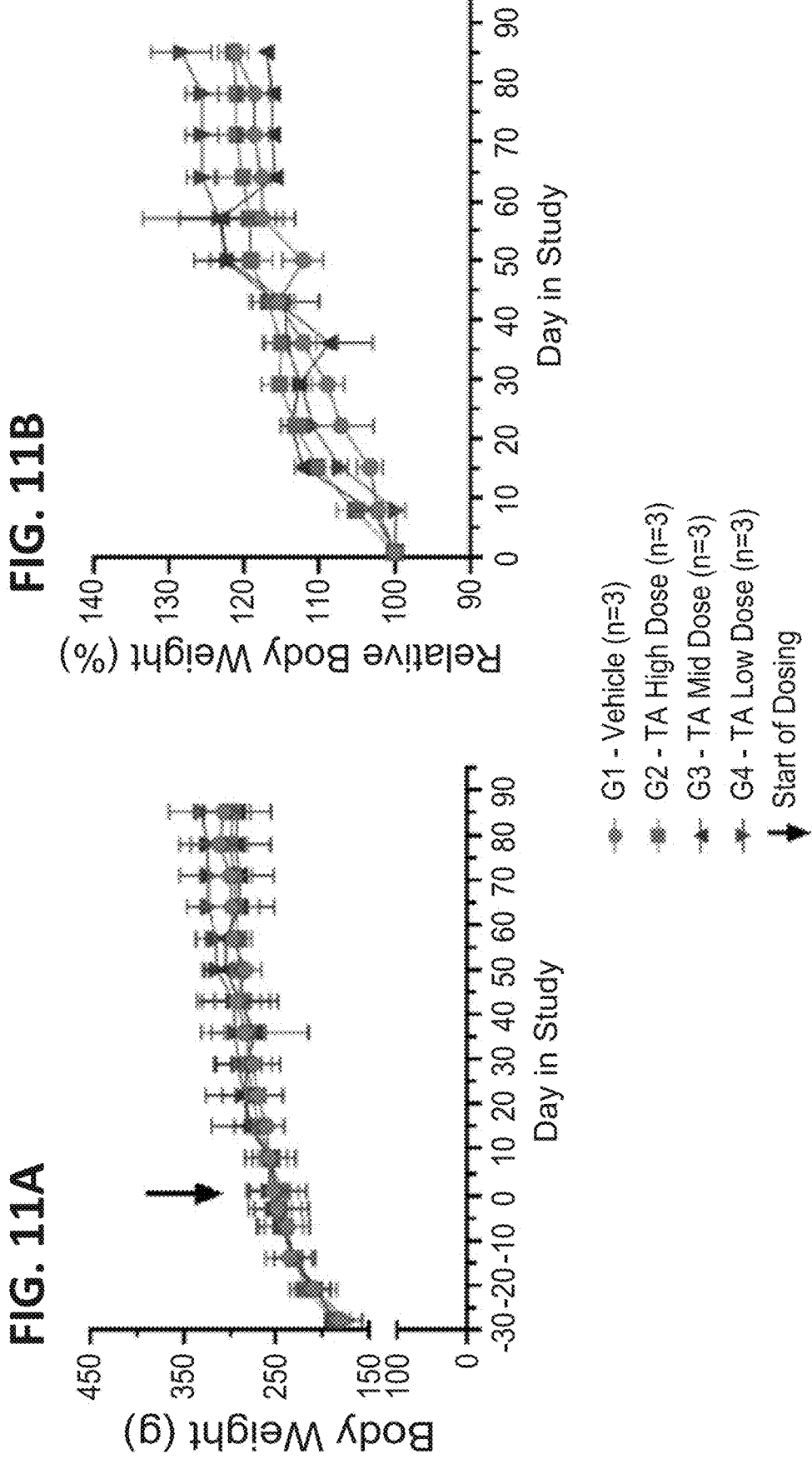
FIG. 11A shows average body weight (mean±SD) and FIG. 11B shows relative body weight (mean±SEM) of female Sprague Dawley rats throughout a subchronic toxicology study of *Saccharomyces cerevisiae* S288C-I EV1-Peptide. Relative body weight was calculated to the start of dosing on Day 1. No significance was found. (Two-way ANOVA with repeated measures Tukey's multiple comparison test *$p<0.05$).
Figure 13B:
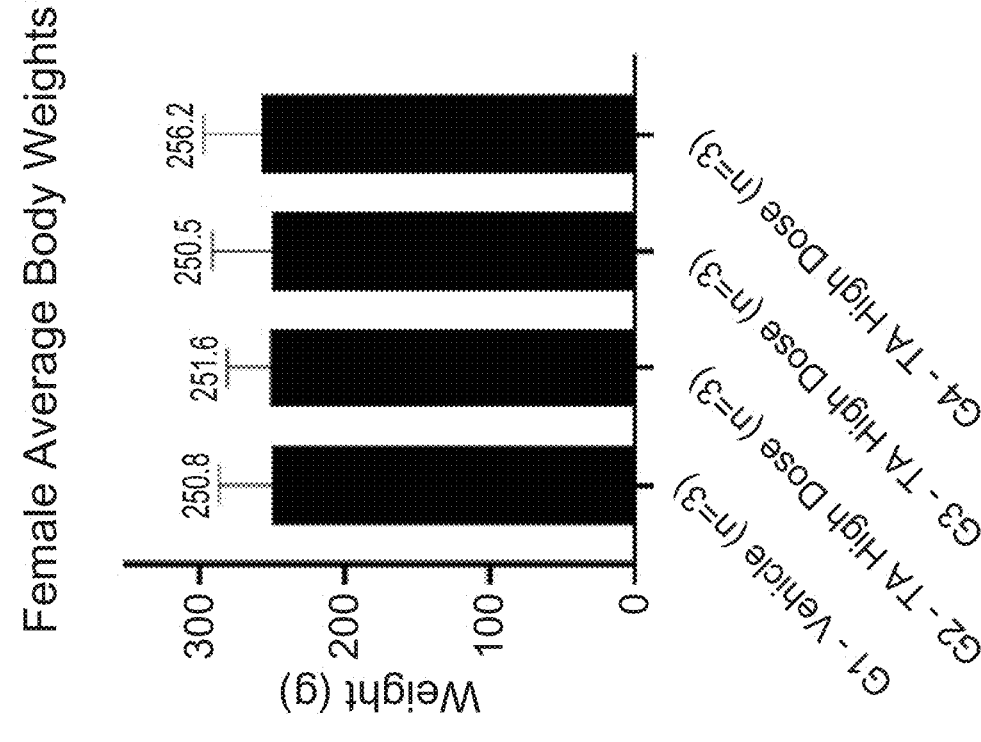
FIG. 13B shows average body weights of female Sprague Dawley rats throughout study (mean±SD), within treatment groups. The average body weight for all animals, both genders, over the entire study was 367.8 g
Figure 13A:
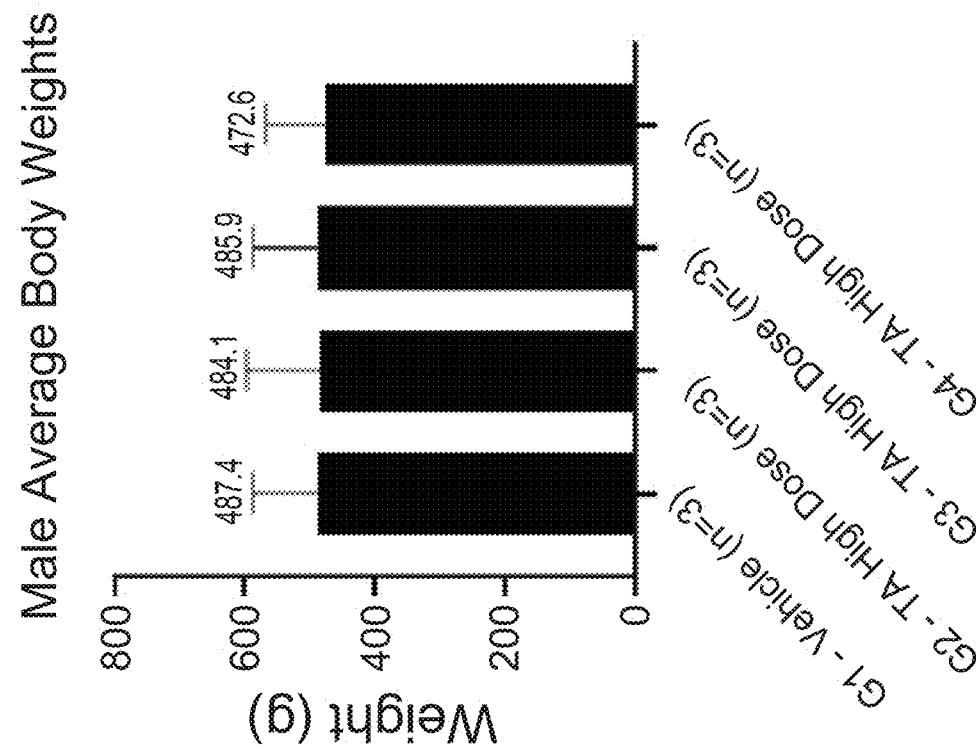
FIG. 13A shows average body weights of male Sprague Dawley rats throughout study (mean±SD)

There were no significant differences between the treated groups and controls in body weights. Overall, female body weights across every treatment group varied slightly more (FIG. 11A-FIG. 11B) when compared to male body weights (FIG. 12A-FIG. 12B) throughout the study. The average body weight for males and females per dose group is presented in FIG. 13A and FIG. 13B. The average body weight in males was 482.5 g and in females was 252.3 g. The average body weight for all animals over the entire study was 367.8 g.

FIG. 14 and FIG. 15 show average food consumption for male and female rats, respectively, across treatment conditions throughout the study. Among the female animals, there was a decrease in food consumption in animals treated with the mid dose (0.15 g) starting in week 6 that continued for the duration of the dosing period (FIG. 15).

No significant changes were observed following the analysis of blood samples. No significant differences in organ weights were noted in the treated animals compared to controls. Results of the gross necropsy performed on each animal indicated no abnormalities for any animals among any organs. Pancreatic tissue was sent for additional analysis and histology, and results of the histopathological analysis were unremarkable.

Example 9: a Randomized, Controlled Study to Evaluate the Effects of a Supplement on Weight Loss, Blood Sugar, and Appetite Suppression Study Rationale Obesity is a growing concern in the Western world. In the U.S.A. approximately 42% of adults are obese, with the number having increased substantially over the past decade. The prevalence of obesity changes depending on race and ethnicity. Non-Hispanic Black adults experience the highest prevalence (49.9%) followed by Hispanic (45.6%), non-Hispanic White (41.4%), and non-Hispanic Asian (16.1%) adults. (cdc.gov/obesity/php/data-research/adult-obesity-facts.html).

Many factors lead to an individual becoming obese. Genetics are thought to play a role through the disruption of genes involved in fat storage, energy expenditure, and appetite (Wu et al., *Eat Weight Disord* 2023; 28 (1): 84). However, the large rise in the number of people with obesity over the last 50 years is mainly due to aspects of the modern Western lifestyle including a lack of physical activity and overconsumption of hyperpalatable, calorie-dense food (Welsh et al., *Eur J Prev Cardiol* 2024; 31 (8): 1026-1035). Other obesity-contributing factors include microbiome composition (Tambo et al., *Int J Chronic Dis* 2016; 2016: 7030795), socioeconomic status (Watts et al., *Prev Med* 2016; 87:194-199), and side effects from medication (Sfera et al., *Front Endocrinol (Lausanne)* 2020; 11:488).

Obesity is a serious condition which can lead to other serious diseases. The risk of developing cardiovascular diseases (CVD), including coronary artery disease and heart failure, and CVD risk factors, including hypertension and insulin resistance, is increased by obesity (Jin et al., *Acta Pharm Sin B* 2023; 13 (6): 2403-2424). Obesity has been linked to 13 types of cancer, including breast, ovarian, stomach, liver, and pancreatic cancers (Jin et al., *Acta Pharm Sin B* 2023; 13 (6): 2403-2424). Obesity is also the main risk factor in the development of type 2 diabetes, a long-term condition that requires daily control measures to be put in place to prevent complications such as kidney damage (Liu et al., *J Diabetes Res* 2022; 2022:1531289).

For this clinical trial, the present inventors developed a novel baker's yeast extract from a strain modified to express a new protein (EV1-Peptide) to interact with GLP-1 and GIP receptors. This clinical trial is intended to determine effectiveness in reducing weight, controlling appetite, and improving glycemic control. In particular, recognizing the growing problem of obesity and the importance of weight loss and glucose control in individuals struggling with their weight, the inventors have developed a supplement using the appetite-suppressing and glucose-controlling actions of baker's yeast extract called *Saccharomyces cerevisiae* S288C EV1-Peptide, described in the Examples herein. This baker's yeast has been modified so that it expresses a novel protein (EV1-Peptide) that is thought to interact with incretin receptors in the body. Other than the expression of this single new protein, the ingredient is identical to wild-type baker's yeast (*S. cerevisiae*). This supplement has been produced to aid appetite suppression, weight loss, and blood sugar levels in addition to associated well-being variables.

Summary of Study

This is a hybrid, two-armed, randomized, controlled clinical trial that will last 12 weeks. Participants will be randomized into either a test product group that will take the Evolv GLP-1 product twice daily (in the morning and afternoon/evening) or a control group. The control group will be provided with a standardized recommendation for healthy eating from the American Diabetes Association.

All participants will attend their local laboratory testing facility to undergo blood testing at Baseline and Week 12 (Endline), and potentially at Week 6. Participants will complete study-specific questionnaires and submit weight measurements at Baseline, Week 4, Week 8, and Week 12, and potentially at Week 6.

Study Population

This study will recruit 120 female and male participants, aged 18+.

Arm 1: Intervention—60 participants

Arm 2: Control—60 participants

Inclusion Criteria

1. Be male or female.
2. Be aged 18+.
3. BMI of 25-29.9 kg/m2.
4. Anyone with concerns regarding all of the following for the past 12 weeks: a. Weight management; b. Food cravings and/or appetite management.
5. Must not be living with any uncontrolled chronic disease.
6. Not currently taking, and not planning to take for the duration of the test period, any products, prescription medications, herbal remedies, over-the-counter medications, or supplements that target blood sugar regulation, weight, or appetite.
7. Willing to maintain their current diet, sleep schedule, and activity level for the duration of the study.
8. Resides in the United States.
9. Not currently partaking in another research study and will not be partaking in any other research study for the next 12 weeks and at any point during this study's duration.

Exclusion Criteria

An individual who meets the following criteria will be excluded from participation in this study:

1. Diagnosed with Type 1 diabetes, any metabolic or endocrine disorder, or any disorder that affects blood sugars (e.g., hypothyroidism, Hashimoto's thyroiditis).
2. Diagnosed with Type 2 diabetes mellitus (T2DM) and have been prescribed metformin, insulin, Sulfonylureas, Meglitinides, SGLT2 inhibitors and/or GLP-1 medications including the following prescription medications: Wegovy (semaglutide), Ozempic (semaglutide), Rybelsus (semaglutide), Saxenda (liraglutide), Victoza (liraglutide), Zepbound (bimagrumab), Byetta (exenatide), Bydureon (exenatide ER), Trulicity (dulaglutide), Adlyxin (lixisenatide).
3. Current use or past history of use within the last 2 months (8 weeks) of the following prescription medications: a. Corticosteroids, including Deltasone (Prednisone), Orapred, Prelone (Prednisolone), Medrol (Methylprednisolone), Qvar (Beclomethasone), Celestone (Betamethasone), Decadron (Dexamethasone), Cortef (Hydrocortisone), Kenalog (Triamcinolone); b. Immunosuppressants, including Tacrolimus (Prograf), Cyclosporine (Neoral), Sirolimus (Rapamune).
4. Anyone who has been treated with any antibiotic or antifungal prescription medication in the last 2 months (8 weeks).
5. Anyone with pre-existing chronic conditions that would prevent participants from adhering to the protocol, including cancer, liver, and psychiatric disorders.
6. Is currently undergoing or planning to undergo any significant medical procedures in the next six months
7. Anyone who has undergone any surgeries or invasive treatments in the last six months, or has any planned during the study period.
8. Has had any major illness in the last three months.
9. Anyone with known severe allergic reactions, including those requiring the use of an Epi-pen.
10. Anyone with any allergies or sensitivities to any of the study product ingredients.
11. Any women who are pregnant, breastfeeding, or trying to conceive (or who will be at any point during the study period).
12. Heavy drinkers or drug users. A heavy drinker is considered to be a woman who drinks 8 or more alcoholic drinks per week or a man who drinks 15 or more alcoholic drinks per week.

13. Anyone unwilling to follow the study protocol.
14. Anyone with a history of substance abuse.
15. Anyone who is currently a smoker or has been a smoker in the past 3 months.

Note on Weight Measurements:

At Baseline and Week 12, participants will provide body weight measurements daily for three consecutive days. If the first two measurements are similar, then the average of these two values will be used for their body mass for that time point. If the two values vary considerably then the third measurement will be used with the average of the two values that are most similar used for analysis.

Additional Study Details

Study Duration: 12 weeks

Participant Duration: 12 weeks

Product Instructions: Participants in the intervention group will take 8 capsules daily—4 capsules in the AM and 4 capsules in the PM. The product should be taken before a meal.

Ingredients: One capsule contains 200 mg *Saccharomyces cerevisiae* S288C EV1-Peptide, 200 mg rice flour, 20 mg bamboo silica, and 2 mg calcium laurate.

Devices: Weight measurement scale

Biomarkers: Participants will undergo blood testing at the following time points: Baseline; Mid-point (Week 6); Endline (Week 12).

Blood testing will include the following: Hemoglobin A1c with eAG (HgbA1c) measurement.

Objectives & Endpoints

Primary Objectives & Endpoints

The primary objective is to examine the product's effects on weight loss and blood sugar control. Primary endpoints are 1) blood sugar, which will be evaluated via bloodwork measuring Hemoglobin A1c with eAG (HgbA1c) at baseline, Week 6, and Week 12; and 2) weight, which will be evaluated via at home testing at baseline, Week 4, Week 6, Week 8, and Week 12. These endpoints are selected to provide an objective overview of the effect of the product on blood sugar and weight.

Secondary Objectives & Endpoints

The secondary objectives are to examine the participants' perceptions of the effects of the test product on weight loss, appetite suppression (including curbing cravings), blood sugar, and other outcomes related to well-being. The secondary endpoints are participant perception of the product's effect on weight loss, appetite suppression, blood sugar, and other outcomes related to well-being, which will be evaluated at Baseline, Week 4, Week 6, Week 8, and Week 12 via self-reported questionnaire. These endpoints are selected to evaluate participant perception of the product.

Overall Study Design

This study is a randomized, two-group trial of 120 participants with the Evolv GLP-1 supplement of the present disclosure.

Participants will be randomized into one of two arms. Arm 1 will take the Evolv GLP-1 supplement throughout the trial. Arm 2 will be allocated to the control condition for the duration of the trial. Participants in the control condition will not be provided with any product and instead will be provided with a standardized recommendation for healthy eating from the American Diabetes Association (diabetesfoodhub.org/blog/what-diabetes-plate).

At Baseline, Week 4, Week 6, Week 8, and Week 12, participants will complete questionnaires and submit weight measurements. Participants will attend a Quest Diagnostic center for Baseline bloodwork and complete further bloodwork at the center in Weeks 6 and 12. The final questionnaire, weight measurement, and bloodwork at Week 12 will mark the end of the study.

At Baseline, Week 4, Week 6, Week 8, and Week 12, participants will provide body mass measurements daily for three consecutive days. If the first two measurements are similar, then the average of these two values will be used for their body mass for that time point. If the two values vary considerably, then the third measurement will be used with the average of the two values that are most similar to those used for analysis.

The trial will be a hybrid study consisting of virtual questionnaires, at-home body weight measurements, and in-person bloodwork. The participants will follow the instructions provided by the research team.

Trial Design and Dosing Justification

This trial will be a hybrid trial. Participants will complete questionnaires and body weight measurements at home and will attend their local laboratory testing facility to undergo blood testing.

To best understand the benefits of the test product, a randomized, controlled, study design is the gold-standard method. A 12-week study duration provides sufficient time for the test product to provide statistically significant effects that may lead to weight loss, appetite suppression, and improved blood sugar regulation.

The data collection intervals for this trial were chosen to minimize the participant burden while still collecting valuable data about the efficacy of the test product. In addition to subjective data collected from questionnaires, objective quantitative data will be obtained from weight measurements and bloodwork. The 12-week duration also enables sufficient time to observe changes in Hemoglobin Alc with eAG (HgbAlc).

120 participants, 60 each in the intervention and control arms, is sufficient to establish differences between the two study conditions. This will allow for meaningful between-group comparisons to adequately test the efficacy of the test product versus control.

The test product examined in this study will be taken in dosages higher than those intended for the eventual commercially available products. This will be done to help establish the efficacy, tolerability, and safety of the test product.

Study Intervention

Potential participants who meet the initial inclusion and exclusion criteria will have the option of participating in this trial. After signing the informed consent, participants will begin the trial by taking the initial Baseline survey, submitting a weight measurement, and attending a local laboratory testing facility for a Baseline blood draw. For the weight measurements, participants will provide body mass measurements daily for three consecutive days. If the first two measurements are similar, then the average of these two values will be used for their body mass for that time point. If the two values vary considerably, then the third measurement will be used with the average of the two values that are most similar used for analysis.

After the Baseline data collection, participants will be randomly allocated into the intervention or control study group. At this point, participants in the intervention group will receive their product and begin using it as directed.

Participants in the intervention group will take 4 capsules daily-2 capsules in the am and 2 capsules in the pm. The product should be taken before a meal.

Participants in the control group will be provided with a standardized recommendation for healthy eating (e.g. diabetesfoodhub.org/blog/what-diabetes-plate).

At Week 4, Week 6, Week 8, and Week 12, participants will complete further questionnaires and submit weight measurements. Participants will return to their local laboratory testing facility for blood draws at Week 12.

Completion of questionnaires, blood draws and weight measurements at the end of Week 12 will mark the conclusion of the trial.

Intervention Formulation

Intervention Product Ingredients: Modified baker's yeast 300 mg, Hydroxypropylcellulose, 90 mg, Microcrystalline cellulose NF, 75 mg, Bamboo silica, 25 mg.

Participant Discontinuation/Withdrawal from the Study

Participants are free to withdraw from participation in the study at any time upon request.

An investigator may discontinue or withdraw a participant from the study for the following reasons: Pregnancy; Significant study intervention non-compliance; If any clinical adverse event (AE), laboratory abnormality, or other medical condition or situation occurs such that continued participation in the study would not be in the best interest of the participant; Disease progression which requires discontinuation of the study intervention; If the participant meets an exclusion criterion (either newly developed or not previously recognized) that precludes further study participation; Participant should be withdrawn from the study if they start on a new drug or receive antibiotics.

The reason for participant discontinuation or withdrawal from the study will be recorded on a Case Report Form (CRF). Participants who sign the informed consent form but do not receive the study intervention may be replaced. Participants who sign the informed consent form, receive the study intervention, and subsequently withdraw, or are withdrawn or discontinued from the study, will not be replaced.

Blood Testing

Participants will undergo blood testing at the following time points: Baseline, Week 6, and Endline (Week 12). Blood testing will include the following: Hemoglobin Alc with eAG (HgbAlc).

End Of Study Definition

A participant is considered to have completed the trial if they have completed all study phases, including the last scheduled assessments at endline (Week 12 questionnaire, bloodwork, and weight measurements).

Statistical Considerations

Following data collection and the completion of the trial, the data will be analyzed by Citruslabs to determine the effect of the intervention over 12 weeks. Differences between the control group and test product group will be evaluated statistically. Where appropriate, within-group analysis will also be performed comparing specific time point data to Baseline. Data will be analyzed using an Intention-to-treat analysis (ITT).

Figure 16:
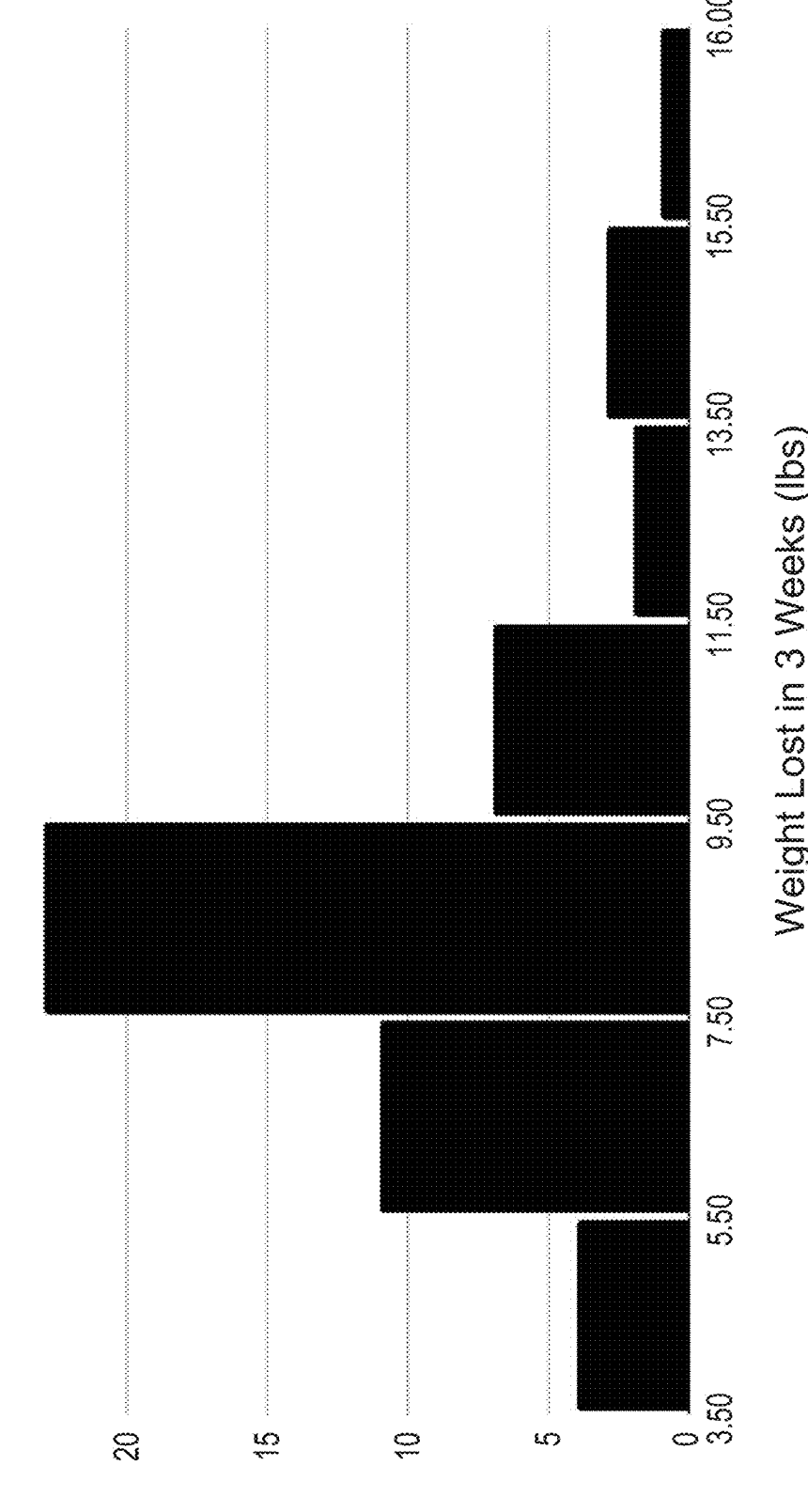
FIG. 16 shows the distribution of weight loss extrapolated to 3 weeks for 51 subjects taking oral Evolv GLP-1 Biomimetic. Average weight loss for these subjects in this extrapolated time period was about 9 lbs.

Example 10: Significant Weight Loss Observed after 3 Weeks of Daily Consumption of Evolv GLP-1 Biomimetic Weight loss results from 51 subjects who consumed the Evolv GLP-1 Biomimetic supplement product were recorded. The supplement contained 500-800 mcg of EV1 Peptide per capsule and subjects consumed 1-2 capsules by mouth per day. Weight loss results were self-reported for a range of 6-42 days. The data is presented as a bar graph extrapolated to 3 weeks (21 days) for ease of comparison (FIG. 16). The raw anonymized tabulated data was also collected and is disclosed herein in Table 8 below. The average reported weight loss when extrapolated to 3 weeks of consuming the supplement product was 8.7 pounds, with reports ranging from 3.75 to 15.75 pounds lost over the 3-week interval. During this period, subjects also self-reported no significant muscle loss with a healthy diet and fitness regimen, and an intake reduction of about 1000 calories per day without restrictive dieting.

TABLE 8

Weight Loss Results for 51
Subjects Consuming Evolv GLP-1 Biomimetic.

| Participant No. | Weight Lost (lbs) | Time Period (days) | Weight Lost in 3 Weeks (lbs) |
|---|---|---|---|
| 1 | 10 | 21 | 10 |
| 2 | 9 | 28 | 6.8 |
| 3 | 12 | 28 | 9 |
| 4 | 11 | 28 | 8.3 |
| 5 | 10 | 21 | 10 |
| 6 | 5 | 28 | 3.8 |
| 7 | 5 | 14 | 7.5 |
| 8 | 12 | 42 | 6 |
| 9 | 6 | 28 | 4.5 |
| 10 | 5 | 14 | 7.5 |
| 11 | 7 | 14 | 10.5 |
| 12 | 11 | 35 | 6.6 |
| 13 | 5 | 21 | 5 |
| 14 | 13 | 28 | 9.8 |
| 15 | 6 | 14 | 9 |
| 16 | 8 | 14 | 12 |
| 17 | 2 | 6 | 7 |
| 18 | 2 | 7 | 6 |
| 19 | 2 | 8 | 5.3 |
| 20 | 2 | 6 | 7 |
| 21 | 4 | 8 | 10.5 |
| 22 | 6 | 15 | 8.4 |
| 23 | 6 | 14 | 9 |
| 24 | 3 | 6 | 10.5 |
| 25 | 5 | 14 | 7.5 |
| 26 | 6 | 8 | 15.8 |
| 27 | 2 | 6 | 7 |
| 28 | 5 | 13 | 8.1 |
| 29 | 3 | 7 | 9 |
| 30 | 2 | 6 | 7 |
| 31 | 3 | 8 | 7.9 |
| 32 | 6 | 14 | 9 |
| 33 | 2 | 6 | 7 |
| 34 | 3 | 8 | 7.9 |
| 35 | 3 | 8 | 7.9 |
| 36 | 3 | 7 | 9 |
| 37 | 3 | 7 | 9 |
| 38 | 3 | 8 | 7.9 |
| 39 | 3 | 7 | 9 |
| 40 | 3 | 8 | 7.9 |
| 41 | 4 | 8 | 10.5 |
| 42 | 10 | 14 | 15 |
| 43 | 4 | 7 | 12 |
| 44 | 3 | 7 | 9 |
| 45 | 5 | 7 | 15 |
| 46 | 2 | 6 | 7 |
| 47 | 3 | 7 | 9 |
| 48 | 3 | 7 | 9 |
| 49 | 5 | 7 | 15 |
| 50 | 2 | 6 | 7 |
| 51 | 3 | 7 | 9 |
| Average Weight Lost in 3 Weeks: | | | 8.7 |

REFERENCES

Bahijiri S M, Mira S A, Mufti A M, Ajabnoor M A. The effects of inorganic chromium and brewer's yeast supplementation on glucose tolerance, serum lipids and drug dosage in individuals with type 2 diabetes. Saudi Med J. 2000 September; 21 (9): 831-7. PMID: 11376359.

Botstein D, Fink G. Yeast: An Experimental Organism for 21st Century Biology. Genetics Society of America. 2011. DOI: 10.1534/genetics.111.130765.

Briskey D, Skinner R A, Zhang H, Chen Z, Rao A. Effect of Yeast Protein on Muscle Mass and Performance in an Adult Population. Journal of Food and Nutrition Research. 2024. DOI: 10.12691/jfnr-12-5-9

CDC. Obesity is a Common, Serious, and Costly Disease. Centers for Disease Control and Prevention. Published May 28, 2024. Accessed Oct. 15, 2024. www.cdc.gov/obesity/php/data-research/adult-obesity-facts.html Codex *Alimentarius* Commission, Joint FAO/WHO Food Standard Programme. Appendix III, Guideline for the conduct of food safety assessment of foods derived from recombinant-DNA plants and Appendix IV, Annex on the assessment of possible allergenicity. 2003.

EFSA (European Food Safety Authority). Scientific Opinion on the maintenance of the list of QPS biological agents intentionally added to food and feed. EFSA J 8 (12): 1-56. 2010. DOI: 10.2903/j.efsa.2010.1944.

EPA (U.S. Environmental Protection Agency). 1997. Final risk assessment of *Saccharomyces cerevisiae:* 13.

FAO/WHO. 1971. Joint FAO/WHO Expert Committe on Food and Additives.

FDA (U.S. Food and Drug Administration). 2001. Partial list of microorganisms and microbial-derived ingredients that are used in foods. Available: www.fda.gov/food/generally-recognized-safe-gras/microorganisms-microbial-derived-ingredients-used-food-partial-list.

Goffeau A, Barrell B G, Bussey H, et al. Life with 6000 genes. Science. 1996; 274:563-547. doi: 10.1126/science.274.5287.546.

GRAS Notice (GRN) No. 1096 with Amendments www.fda.gov/food/generally-recognized-safe-gras/gras-notice-inventory Hileman R, Silvanovich A, Goodman R, Rice E, Holleschak G, Astwood J, Hefle S. Bioinformatic Methods for Allergenicity Assessment Using a Comprehensive Allergen Database. International Archives of Allergy and Immunology. 2002. DOI: 10.1159/000063861.

Jach M, Serefko A, Ziaja m, Kieliszek M. Yeast Protein as an Easily Accessible Food Source. Metabolites. 2022. DOI: 10.3390/metabo12010063

Jin X, Qiu T, Li L, Yu R, Chen X, Li C, Proud C G, Jiang T. Pathophysiology of obesity and its associated diseases. Acta Pharm Sin B. 2023 June; 13 (6): 2403-2424. doi: 10.1016/j.apsb.2023.01.012

Jung E Y, Cho M K, Hong Y H, Kim J H, Park Y, Chang U J, Suh H J. Yeast hydrolysate can reduce body weight and abdominal fat accumulation in obese adults. Nutrition. 2014 January; 30 (1): 25-32. doi: 10.1016/j.nut.2013.02.009

Jung E Y, Lee J W, Hong Y H, Chang U J, Suh H J. Low Dose Yeast Hydrolysate in Treatment of Obesity and Weight Loss. Prev Nutr Food Sci. 2017 March; 22 (1): 45-49. doi: 10.3746/pnf.2017.22.1.45

Kour D, Sood M, Gupta N, Singh J, Bhat A, Bandral J, Reshi M, Gupta S, Choudhary A. Yeast Protein: Novel and Alternative Protein in Food Applications. Chemical Science Review and Letters. 2023. DOI: 10.37273/chesci.cs205407607

Liu R, Li L, Shao C, Cai H, Wang Z. The Impact of Diabetes on Vascular Disease: Progress from the Perspective of Epidemics and Treatments. J Diabetes Res. 2022 Apr. 8; 2022:1531289. doi: 10.1155/2022/1531289

Lopez M, Mohiuddin S. Biochemistry, Essential Amino Acids. NCBI Bookshelf. 2024. PMID: 32496725.

National Research Council of the National Academies. Guide for the Care and Use of Laboratory Animals, Eighth Edition. Institute for Laboratory Animal Research. Division on Earth hand Life Sciences. 2011. DOI: 10.17226/12910

New Dietary Ingredient Notification (NDIN) No. 1071 with Amendments www.regulations.gov/document/FDA-2018-S-0023-0078

New Dietary Ingredient Notification (NDIN) No. 1241 with Amendments www.regulations.gov/document/FDA-2022-S-0023-0015

New Dietary Ingredient Notification (NDIN) No. 1303 with Amendments www.regulations.gov/search?filter=ndi % 201303

Parapouli M, Vasileiadis A, Afendra A S, Hatziloukas E. *Saccharomyces cerevisiae* and its industrial applications. AIMS Microbiol. 2020 Feb. 11; 6 (1): 1-31. doi: 10.3934/microbiol.2020001. PMID: 32226912; PMCID: PMC7099199.

Racek J, Trefil L, Rajdl D, Mudrová V, Hunter D, Senft V. Influence of chromium-enriched yeast on blood glucose and insulin variables, blood lipids, and markers of oxidative stress in subjects with type 2 diabetes mellitus. Biol Trace Elem Res. 2006 March; 109 (3): 215-30. doi: 10.1385/BTER: 109:3:215

Sfera A, Osorio C, Diaz E L, Maguire G, Cummings M. The Other Obesity Epidemic—Of Drugs and Bugs. Front Endocrinol (Lausanne). 2020 Jul. 31; 11:488. doi: 10.3389/fendo.2020.00488

Tambo A, Roshan M H, Pace N P. The Microbial Hypothesis: Contributions of Adenovirus Infection and Metabolic Endotoxaemia to the Pathogenesis of Obesity. Int J Chronic Dis. 2016; 2016:7030795. doi: 10.1155/2016/7030795

Watts A W, Mason S M, Loth K, Larson N, Neumark-Sztainer D. Socioeconomic differences in overweight and weight-related behaviors across adolescence and young adulthood: 10-year longitudinal findings from Project EAT. Prev Med. 2016 June; 87:194-199. doi: 10.1016/j.ypmed.2016.03.007

Welsh A, Hammad M, Piña IL, Kulinski J. Obesity and cardiovascular health. Eur J Prev Cardiol. 2024 Jun. 3; 31 (8): 1026-1035. doi: 10.1093/eurjpc/zwae025

Wu W, Chen Z, Han J, Qian L, Wang W, Lei J, Wang H. Endocrine, genetic, and microbiome nexus of obesity and potential role of postbiotics: a narrative review. Eat Weight Disord. 2023 Oct. 20; 28 (1): 84. doi: 10.1007/s40519-023-01593-w

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as an acknowledgment or any form of suggestion that they constitute valid prior art or form part of the common general knowledge in any country in the world.

Numbered Embodiments

Notwithstanding the appended claims, the disclosure sets forth the following numbered embodiments:

Embodiment 1. A fusion protein comprising: a) a molecular cargo domain; and b) at least one transduction domain.

Embodiment 2. The fusion protein of embodiment 1, wherein the fusion protein comprises a transduction domain at the N-terminus and/or C-terminus of the fusion protein.

Embodiment 3. The fusion protein of embodiment 1 or 2, wherein the fusion protein comprises a transduction domain at each of the N-terminus and the C-terminus of the fusion protein.

Embodiment 4. The fusion protein of any one of embodiments 1-3, wherein the fusion protein comprises a transduction domain comprising a GM-1 binding peptide at one terminus and a transduction domain comprising a CPP at the other terminus.

Embodiment 5. The fusion protein of any one of embodiments 1-4, wherein at least one transduction domain comprises a GM1 receptor binding protein (GM1-BP), transferrin, antibody fragment crystallizable region (Fc region), a dendritic cell peptide (DCpep), or a cell penetrating peptide (CPP).

Embodiment 6. The fusion protein of any one of embodiments 1-5, wherein at least one transduction domain comprises a GM1-BP selected from: Cholera Toxin B subunit (CTB), Heat-labile Enterotoxin B subunit (LTB), and an anti-GM1 antibody.

Embodiment 7. The fusion protein of any one of embodiments 1-6, wherein at least one transduction domain comprises an amino acid sequence having at least 85% sequence identity to the amino acid sequence of SEQ ID NO: 8 (HLNILSTLWKYR).

Embodiment 8. The fusion protein of any one of embodiments 1-7, wherein at least one transduction domain comprises the amino acid sequence of SEQ ID NO: 8 (HLNILSTLWKYR).

Embodiment 9. The fusion protein of any one of embodiments 1-8, wherein at least one transduction domain comprises a CPP.

Embodiment 10. The fusion protein of any one of embodiments 1-9, wherein at least one transduction domain comprises a CPP selected from the list consisting of: TAT, ATX-101, AM-111, P28, ALRN-6924, R7, (R-Ahx-R) 4, TransMTS, MTS, AVB-620 (ACPP), Pepducin, BT1718, PEP-010, ATP128, PTD4, and a charged oligo peptide.

Embodiment 11. The fusion protein of any one of embodiments 1-10, wherein at least one transduction domain comprises a CPP that binds to PDX-1.

Embodiment 12. The fusion protein of any one of embodiments 1-11, wherein at least one transduction domain comprises an amino acid sequence having at least 85% sequence identity to the amino acid sequence of SEQ ID NO: 10 (RHIKIWFQNRRMKWKK).

Embodiment 13. The fusion protein of any one of embodiments 1-12, wherein at least one transduction domain comprises the amino acid sequence of SEQ ID NO: 10 (RHIKIWFQNRRMKWKK).

Embodiment 14. The fusion protein of any one of embodiments 1-13, wherein the fusion protein comprises a solubility-enhancing domain.

Embodiment 15. The fusion protein of embodiment 14, wherein the solubility-enhancing domain comprises a domain selected from the list consisting of: maltose-binding protein (MBP), cross-linked amylose/maltose, glutathione S-transferase (GST), SlyD, thioredoxin (Trx), galactose, ubiquitin, N-utilization substance A (NusA), small ubiquitin-like modifier (SUMO), and green fluorescent protein (GFP).

Embodiment 16. The fusion protein of embodiment 14 or embodiment 15, wherein the solubility-enhancing domain comprises MBP.

Embodiment 17. The fusion protein of any one of embodiments 14-16, wherein the solubility-enhancing domain comprises a sequence having at least 85% sequence identity to the amino acid sequence of SEQ ID NO: 9.

Embodiment 18. The fusion protein of any one of embodiments 14-17, wherein the solubility-enhancing domain comprises the amino acid sequence of SEQ ID NO: 9.

Embodiment 19. The fusion protein of any one of embodiments 1-18, wherein the fusion protein comprises an albumin binding domain.

Embodiment 20. The fusion protein of embodiment 19, wherein the albumin binding domain binds to an albumin serum protein or at least a fragment, epitope, or domain thereof.

Embodiment 21. The fusion protein of embodiment 19 or 20, wherein the albumin binding domain comprises an amino acid sequence having at least 85% sequence identity to the amino acid sequence of SEQ ID NO: 7 (WWEQDRDWDFDVFGGGTP).

Embodiment 22. The fusion protein of any one of embodiments 19-21, wherein the albumin binding domain comprises the amino acid sequence of SEQ ID NO: 7 (WWEQDRDWDFDVFGGGTP).

Embodiment 23. The fusion protein of any one of embodiments 1-22, wherein the fusion protein comprises at least one protease cleavage site.

Embodiment 24. The fusion protein of embodiment 23, wherein the fusion protein comprises two protease cleavage sites.

Embodiment 25. The fusion protein of embodiment 24, wherein the fusion protein comprises a protease cleavage site N-terminally and C-terminally from the molecular cargo domain.

Embodiment 26. The fusion protein of any one of embodiments 23-25, wherein the fusion protein comprises a protease cleavage site between the molecular cargo domain and a transduction domain.

Embodiment 27. The fusion protein of any one of embodiments 23-26, wherein the protease cleavage site(s) are selected from: furin, BACE1, BACE2, Cathepsin D, Cathepsin E, Chymosin (or "rennin"), Napsin-A, Nepenthesin, Pepsin, Presenilin, Renin, Papain, bromelain, cathepsin K and, calpain, Caspase-1, separase, Adenain, Pyroglutamyl-peptidase I, Hepatitis C virus peptidase 2, Sindbis virus-type nsP2 peptidase, Dipeptidyl-peptidase VI, DeSI-1 peptidase, TEV protease, Amidophosphoribosyltransferase precursor, Gamma-glutamyl hydrolase, Hedgehog protein, DmpA aminopeptidase, Subtilisin, Prolyl oligopeptidase, D-Ala-D-Ala peptidase C, Signal peptidase I, Cytomegalovirus assembling, Lon-A peptidase, Clp protease, Phage KIF endosialidase CIMCD self-cleaving protein, Nucleoporin 145, Lactoferrin, Murein tetrapeptidase LD-carboxypeptidase, Rhomboid-1, Chymotrypsin A, Penicillin G acylase precursor, Dipeptidase E, DmpA aminopeptidase, MMP 1 to MMP 28, Interstitial collagenase, Gelatinase-A, 72 kDa gelatinase, Stromelysin 1, Matrilysin, PUMP 1, Neutrophil collagenase, Gelatinase-B, 92 kDa gelatinase, Stromelysin 2, Stromelysin 3, Macrophage metalloelastase, Collagenase 3, MT1-MMP, MT2-MMP, MT3-MMP, MT4-MMP, Collagenase 4, RASI-1, stromelysin-4, Enamelysin, X-MMP, CA-MMP, MT5-MMP, MT6-MMP, Matrilysin-2, endometase, MMP-22, C-MMP, and Epilysin cleavage sites.

Embodiment 28. The fusion protein of any one of embodiments 23-27, wherein at least one protease cleavage site is a furin cleavage site.

Embodiment 29. The fusion protein of any one of embodiments 23-28, wherein at least one protease cleavage site comprises the amino acid sequence of SEQ ID NO: 14 (RKKR).

Embodiment 30. The fusion protein of any one of embodiments 23-39, wherein the fusion protein comprises two protease cleavage sites comprising the amino acid sequence of SEQ ID NO: 14 (RKKR).

Embodiment 31. The fusion protein of any one of embodiments 1-30, further comprising an affinity tag.

Embodiment 32. The fusion protein of embodiment 31, wherein the affinity tag comprises a histidine tag.

Embodiment 33. The fusion protein of embodiment 32, wherein the histidine tag comprises the amino acid sequence of (HHH)n (SEQ ID NO: 74), wherein n is selected from 1, 2, 3, 4, 5, and 6.

Embodiment 34. The fusion protein of any one of embodiments 1-33, wherein the molecular cargo domain comprises a therapeutic peptide selected from the list consisting of: hormonal peptides, cardiovascular peptides, neurological peptides, pain-modulating peptides, antimicrobial peptides, anti-infective peptides, immunomodulatory peptides, oncological peptides, gastrointestinal peptides, dermatological peptides, wound-healing peptides, musculoskeletal peptides, growth-modulating peptides, metabolic peptides, appetite-regulating peptides, diagnostic peptides, an structural peptides.

Embodiment 35. The fusion protein of any one of embodiments 1-34, wherein the molecular cargo domain comprises an incretin agonist.

Embodiment 36. The fusion protein of embodiment 35, wherein the incretin agonist is selected from the list consisting of: a glucagon-like peptide 1 (GLP-1) receptor (GLP-1R) agonist, a gastric inhibitory polypeptide (GIP) receptor (GIP-R) agonist, a dual GLP-1R and GIP-1R incretin agonist, and a triple incretin agonist.

Embodiment 37. The fusion protein of embodiment 35 or 36, wherein the incretin agonist mimetic comprises the sequence of: X1-X2-X3-Gly-Thr-Phe-X7-Ser-X9-X10-X11-Ile-X13-X14-X15-X16-X17-Ala-X19-X20-X21-X22-X23-X24-Trp-Leu-X27-X28-X29-X30-X31-X32-X33-X34-X35-X36-X37-X38-X39-X40-X41-X42 (SEQ ID NO: 16), wherein X1 is His or Tyr; X2 is Ala, Gly, or aminoisobutyric acid (Aib); X3 is Glu or Asp; X7 is Thr, Ser, or Ile; X9 is Asp or Glu; X10 is Tyr, Leu, or Ser; X11 is Ser or Leu; X13 is Ala, Tyr, Aib, or alpha-methyl-L-leucine (αMeL); X14 is Met, Leu, or Ser; X15 is Asp or Glu; X16 is Lys, Gly, Ser, or Glu; X17 is Ile, Lys, Gln, Arg, or Glu; X19 is Gln, Ala, Glu, or Lys; X20 is Gln, Lys, or Arg; X21 is Asp, Ala, or Glu; X22 is Phe; X23 is Val, Ile, or Leu; X24 is Gln, Asn, Glu, Arg or Lys; X27 is Leu, Val, Ile, Lys, Glu, or Ser; X28 is Ala, Ser, Arg, or Aib; X29 is Gln, Glu, Lys, Gly, Tyr, or Aib; X30 is Lys, Gly, Pro, or absent; X31 is Gly, Pro, Ser, Glu, or absent; X32 is Lys, Ser, or absent; X33 is Lys, Ser, Glu, or absent; X34 is Asn, Gly, Ala, Lys, or absent; X35 is Asp, Ala, Pro, Glu, or absent; X36 is Trp, Pro, Lys, or absent; X37 is Lys, Pro, Glu, or absent; X38 is His, Pro, Ser, Lys, or absent; X39 is Asn, Ser, or absent; X40 is Ile or absent; X41 is Thr or absent; and X42 is Gln or absent.

Embodiment 38. The fusion protein of embodiment 35 or 36, wherein the incretin agonist comprises an amino acid sequence having at least 85% sequence identity to the amino acid sequence of SEQ ID NO: 2 (YGEGTFTSDY SIALD-KIAQK AFVQWLIAGG PSSGAPPPS).

Embodiment 39. The fusion protein of any one of embodiments 35 or 36, wherein the incretin agonist comprises the amino acid sequence of SEQ ID NO: 2 (YGEGTFTSDY SIALDKIAQK AFVQWLIAGG PSSGAPPPS).

Embodiment 40. The fusion protein of embodiment 35 or 36, wherein the incretin agonist comprises an amino acid sequence having at least 85% sequence identity to the amino acid sequence of SEQ ID NO: 17 (YGQGTFTSDY SIYLDKQAQQ AFIEYLLEGG PSSGAPPPS).

Embodiment 41. The fusion protein of embodiment 35 or 36, wherein the incretin agonist comprises the amino acid sequence of SEQ ID NO: 17 (YGQGTFTSDY SIYLDKQAQQ AFIEYLLEGG PSSGAPPPS).

Embodiment 42. The fusion protein of any one of embodiments 1-41, wherein the fusion protein comprises, from N-terminus to C-terminus, a first transduction domain, a first protease cleavage site, a molecular cargo domain, a second protease cleavage site, and a second transduction domain.

Embodiment 43. The fusion protein of any one of embodiments 1-42, wherein the fusion protein comprises, from N-terminus to C-terminus, a first transduction domain, a solubility domain, a first protease cleavage site, a molecular cargo domain, a second protease cleavage site, and a second transduction domain.

Embodiment 44. The fusion protein of any one of embodiments 1-42, wherein the fusion protein comprises, from N-terminus to C-terminus, a first transduction domain comprising a GM1-BP or a CPP, a first protease cleavage site, a molecular cargo domain, a second protease cleavage site, and a second transduction domain comprising a GM1-BP or a CPP.

Embodiment 45. The fusion protein of any one of embodiments 1-44, wherein the fusion protein comprises a therapeutic moiety comprising the molecular cargo domain, wherein the fusion protein comprises a non-therapeutic moiety comprising a transduction domain, and wherein the therapeutic moiety and the non-therapeutic moiety are separated by a protease cleavage site.

Embodiment 46. The fusion protein of any one of embodiments 1-45, wherein the fusion protein comprises an amino acid sequence having at least 85% sequence identity to the amino acid sequence of SEQ ID NO: 1.

Embodiment 47. The fusion protein of any one of embodiments 1-46, wherein the fusion protein comprises the amino acid sequence of SEQ ID NO: 1.

Embodiment 48. A nucleic acid encoding the fusion protein of any one of embodiments 1-47.

Embodiment 49. A vector encoding the fusion protein of any one of embodiments 1-47 or comprising the nucleic acid of embodiment 107.

Embodiment 50. A host cell comprising the fusion protein of any one of embodiments 1-47, the nucleic acid of embodiment 48, or the vector of embodiment 49.

Embodiment 51. The host cell of embodiment 50, wherein the host cell is an algal, plant, or yeast cell.

Embodiment 52. The host cell of embodiment 50 or 51, wherein the host cell is a *Saccharomyces cerevisiae* cell.

Embodiment 53. The host cell of any one of embodiments 50-52, wherein the host cell has been dried, lyophilized, and/or ground into a powder.

Embodiment 54. A pharmaceutical composition comprising: the fusion protein of any one of embodiments 1-47 or the host cell of any one of embodiments 50-53; and a pharmaceutically acceptable excipient.

Embodiment 55. A method of making a fusion protein, the method comprising: transfecting a host cell with one or more vectors comprising a nucleic acid encoding the fusion protein of any one of embodiments 1-47; and recombinantly expressing the fusion protein in the host cell.

Embodiment 56. The method of embodiment 55, wherein the method comprises purifying the fusion protein.

Embodiment 57. The method of embodiment 55 or 56, wherein the method comprises lyophilizing the host cell and/or the purified fusion protein.

Embodiment 58. A method of inducing weight loss in a subject in need thereof, the method comprising: orally administering to the subject in need thereof an effective amount of the fusion protein of any one of embodiments 1-47, the host cell of any one of embodiments 50-53, or the pharmaceutical composition of embodiment 54.

Embodiment 59. A method of increasing insulin sensitivity in a subject in need thereof, the method comprising: orally administering to the subject in need thereof an effective amount of the fusion protein of any one of embodiments 1-47, the host cell of any one of embodiments 50-53, or the pharmaceutical composition of embodiment 54.

Embodiment 60. A method of treating diabetes in a subject who has, or is at risk of having, diabetes, the method comprising: orally administering to the subject in need thereof an effective amount of the fusion protein of any one of embodiments 1-47, the host cell of any one of embodiments 50-53, or the pharmaceutical composition of embodiment 54.

Embodiment 61. A method of treating a metabolic disorder in a subject in need thereof, the method comprising: orally administering to the subject in need thereof an effective amount of the fusion protein of any one of embodiments 1-47, the host cell of any one of embodiments 50-53, or the pharmaceutical composition of embodiment 54.

Embodiment 62. The method of embodiment 61, wherein the subject has a disease or condition associated with weight gain.

Embodiment 63. The method of embodiment 62, wherein the disease or condition associated with weight gain is selected from obesity, obesity-linked gallbladder disease, obesity-induced sleep apnea, diabetes, excessive appetite, fatty liver disease, non-alcoholic fatty liver disease (NASH), dyslipidemia, metabolic syndrome, insufficient satiety, hyperinsulinemia, and hypoglycemia.

Embodiment 64. The method of embodiment 61, wherein the subject has insulin resistance syndrome or syndrome X.

Embodiment 65. The method of embodiment 61, wherein the subject has, or is at risk of developing a condition in which there is a lack of or diminished insulin production.

Embodiment 66. The method of any one of embodiment 58-65, wherein the subject has, or is at risk of developing diabetic obesity.

Embodiment 67. The method of any one of embodiment 58-66, wherein the subject has, or is at risk of developing type 1 diabetes, type 2 diabetes, or gestational diabetes.

Embodiment 68. The method of any one of embodiments 58-67, wherein the subject has, or is at risk of developing one or more of hypertension, dyslipidemia, obstructive sleep apnea, and cardiovascular disease.

Embodiment 69. The method of any one of embodiments 58-68, wherein the pharmaceutical composition, the fusion protein, or the host cell is administered at least once or twice daily.

Embodiment 70. The method of any one of embodiments 58-69, wherein the method comprises administration in the form of a tablet or pill.

Embodiment 71. The method of any one of embodiments 58-70, wherein the method leads to a loss of weight.

Embodiment 72. The method of any one of embodiments 58-71, wherein the method leads to a loss of 1-50 lbs.

Embodiment 73. The method of any one of embodiments 58-72, wherein the method leads to a loss of 2-15 lbs.

Embodiment 74. The method of any one of embodiments 58-73, wherein the method leads to a loss of 0.5-20% of original bodyweight.

Embodiment 75. The method of any one of embodiments 58-74, wherein the method leads to a loss of 1-10% of original bodyweight.

Embodiment 76. The method of any one of embodiments 58-75, wherein the method leads to a loss of weight in a period of 1-52 weeks.

Embodiment 77. The method of any one of embodiments 58-76, wherein the method leads to a loss of weight in a period of 1-4 weeks.

Embodiment 78. The method of any one of embodiments 58-77, wherein the method leads to a loss of weight in a period of 3 weeks.

Embodiment 79. A method of treating a condition in a subject in need thereof, wherein the method comprises orally administering to the subject in need thereof an effective amount of the fusion protein of any one of embodiments 1-47, the host cell of any one of embodiments 50-53, or the pharmaceutical composition of embodiment 54. II. EV1-Peptide Specific Claims EV1-Peptide Embodiments Embodiment 1. A dietary supplement, comprising: *Saccharomyces cerevisiae* S288C EV1-Peptide.

Embodiment 2. The dietary supplement of embodiment 1, wherein the *Saccharomyces cerevisiae* S288C EV1-Peptide comprises SEQ ID NO: 1.

Embodiment 3. The dietary supplement of embodiment 1, wherein the EV1-Peptide comprises SEQ ID NO: 6.

Embodiment 4. The dietary supplement of embodiment 1, wherein the *Saccharomyces cerevisiae* S288C EV1-Peptide is encapsulated.

Embodiment 5. The dietary supplement of embodiment 1, wherein the *Saccharomyces cerevisiae* S288C EV1-Peptide is encapsulated in a capsule and present in a dosage form including from about 50 mg to about 1000 mg of *Saccharomyces cerevisiae* S288C EV1-Peptide.

Embodiment 6. The dietary supplement of embodiment 1, wherein the *Saccharomyces cerevisiae* S288C EV1-Peptide is encapsulated in a capsule and present in a dosage form comprising from about 100 mg to about 300 mg of *Saccharomyces cerevisiae* S288C EV1-Peptide.

Embodiment 7. The dietary supplement of embodiment 1, wherein the *Saccharomyces cerevisiae* S288C EV1-Peptide is encapsulated in a capsule and present in a dosage form of about 200 mg of *Saccharomyces cerevisiae* S288C EV1-Peptide.

Embodiment 8. The dietary supplement of embodiment 6, wherein the EV1-Peptide is present from about 100 mcg to about 3000 mcg.

Embodiment 9. The dietary supplement of embodiment 6, wherein the EV1-Peptide is present from about 500 mcg to about 2000 mcg.

Embodiment 10. The dietary supplement of embodiment 7, wherein the EV1-Peptide is present at about 814 mcg.

Embodiment 11. The dietary supplement of embodiment 7, wherein the EV1-Peptide is present at about 1600 mcg.

Embodiment 12. The dietary supplement of embodiment 1, wherein the *Saccharomyces cerevisiae* S288C EV1-Peptide is encapsulated in a vegan capsule.

Embodiment 13. The dietary supplement of embodiment 1, wherein the *Saccharomyces cerevisiae* S288C EV1-Peptide is encapsulated in a vegan capsule engineered for delayed release in the small intestine.

Embodiment 14. The dietary supplement of embodiment 1, wherein the *Saccharomyces cerevisiae* S288C EV1-Peptide is present in a dry powder form.

Embodiment 15. A method of reducing appetite in a human subject, comprising: administering the dietary supplement of embodiment 1 to a human in need thereof.

Embodiment 16. A method of reducing appetite in a human subject, comprising: administering the dietary supplement of embodiment 1 to a human in need thereof in an amount containing about 100 mg to about 300 mg of *Saccharomyces cerevisiae* S288C EV1-Peptide.

Embodiment 17. A method of reducing appetite in a human subject, comprising: administering the dietary supplement of embodiment 1 to a human in need thereof in an amount containing about 200 mg of *Saccharomyces cerevisiae* S288C EV1-Peptide.

Embodiment 18. A method of reducing appetite in a human subject, comprising: administering the dietary supplement of embodiment 1 to a human in need thereof in an amount containing about 500 mcg to about 2000 mcg of EV1-Peptide.

Embodiment 19. A method of reducing appetite in a human subject, comprising: administering the dietary supplement of embodiment 1 to a human in need thereof in an amount containing about 800 to about 1600 mcg of EV1-Peptide.

Embodiment 20. The method of any one of embodiments 15-19, wherein the method leads to weight loss.

Embodiment 21. The method of any one of embodiments 15-20, wherein the method leads to an overall weight loss of 3-20 lbs in a period of 1-4 weeks.

The invention claimed is:

1. A composition comprising: *Saccharomyces cerevisiae* S288C EV1-Peptide, wherein the *Saccharomyces cerevisiae* S288C EV1-Peptide comprises EV1-Peptide comprising SEQ ID NO: 6.

2. The composition of claim 1, wherein the *Saccharomyces cerevisiae* S288C EV1-Peptide comprises SEQ ID NO: 1.

3. The composition of claim 1, wherein the *Saccharomyces cerevisiae* S288C EV1-Peptide is encapsulated.

4. The composition of claim 1, wherein the *Saccharomyces cerevisiae* S288C EV1-Peptide is encapsulated in a capsule and present in a dosage form comprising from about 50 mg to about 1000 mg of *Saccharomyces cerevisiae* S288C EV1-Peptide.

5. The composition of claim 1, wherein the *Saccharomyces cerevisiae* S288C EV1-Peptide is encapsulated in a capsule and present in a dosage form comprising from about 100 mg to about 600 mg of *Saccharomyces cerevisiae* S288C EV1-Peptide.

6. The composition of claim 1, wherein the *Saccharomyces cerevisiae* S288C EV1-Peptide is encapsulated in a capsule and present in a dosage form comprising about 300 mg of *Saccharomyces cerevisiae* S288C EV1-Peptide.

7. The composition of claim 5, wherein the dosage form comprises from about 100 mcg to about 5000 mcg EV1-peptide.

8. The composition of claim 5, wherein the dosage form comprises about 500 mcg to about 3000 mcg EV1-peptide.

9. The composition of claim 6, wherein the dosage form comprises about 900 mcg EV1-peptide.

10. The composition of claim 6, wherein the dosage form comprises about 1800 mcg EV1-peptide.

11. The composition of claim 1, wherein the *Saccharomyces cerevisiae* S288C EV1-Peptide is encapsulated in a vegan capsule.

12. The composition of claim 1, wherein the *Saccharomyces cerevisiae* S288C EV1-Peptide is encapsulated in a vegan capsule engineered for delayed release in the small intestine.

13. The composition of claim 1, wherein the *Saccharomyces cerevisiae* S288C EV1-Peptide is present in a dry powder form.

14. The composition of claim 1, wherein the composition is a dietary supplement.

15. A method of reducing appetite in a human subject, comprising: administering the composition of claim 1 to a human in need thereof.

16. A method of reducing appetite in a human subject, comprising: administering the composition of claim 1 to a human in need thereof in an amount containing about 100 mg to about 600 mg of *Saccharomyces cerevisiae* S288C EV1-Peptide.

17. A method of reducing appetite in a human subject, comprising: administering the composition of claim 1 to a human in need thereof in an amount containing about 300 mg of *Saccharomyces cerevisiae* S288C EV1-Peptide.

18. A method of reducing appetite in a human subject, comprising: administering the composition of claim 1 to a human in need thereof in an amount containing about 500 mcg to about 3000 mcg of EV1-Peptide.

19. A method of reducing appetite in a human subject, comprising: administering the composition of claim 1 to a human in need thereof in an amount containing about 800 to about 2000 mcg of EV1-Peptide.

* * * * *